(12) United States Patent
Garde et al.

(10) Patent No.: US 7,053,058 B2
(45) Date of Patent: May 30, 2006

(54) PHARMACEUTICAL PREPARATIONS AND METHODS FOR INHIBITING TUMORS

(75) Inventors: Seema Garde, Montreal (CA); Chandra Panchal, London (CA); Madhulika Baijal-Gupta, London (CA); Jennifer Fraser, London (CA); Salam Kadhim, Kirkland (CA)

(73) Assignee: Procyon Biopharma Inc., Quebec (CA)

( * ) Notice: Subject to any disclaimer, the term of this patent is extended or adjusted under 35 U.S.C. 154(b) by 566 days.

(21) Appl. No.: 09/977,406

(22) Filed: Oct. 15, 2001

(65) Prior Publication Data

US 2003/0170220 A1 Sep. 11, 2003

(30) Foreign Application Priority Data

Oct. 16, 2000 (CA) ..................................... 2321256
Aug. 20, 2001 (CA) ..................................... 2355334

(51) Int. Cl.
*A61K 38/18* (2006.01)
*A61K 38/16* (2006.01)
*C07K 14/475* (2006.01)

(52) U.S. Cl. .............................. 514/19; 514/2; 514/12; 514/14; 514/17; 514/18; 514/15; 530/300; 530/324; 530/326; 530/330; 530/350

(58) Field of Classification Search ............... 514/2, 514/19, 18, 17, 15, 14, 12; 530/300, 350, 530/330, 326, 324
See application file for complete search history.

(56) References Cited

U.S. PATENT DOCUMENTS 5,428,011 A  6/1995 Seth et al.
5,994,298 A * 11/1999 Tsai et al. ....................... 514/8
6,319,894 B1 * 11/2001 Tracey et al. ................... 514/8

OTHER PUBLICATIONS

Bowie et al, Science, 247: 1306-1310, 1990.*
Burgess et al, J. Cell Biology, 111: 2129-2138, 1990.*
Lazar et al, Molecular and Cellular Biology, 8: 1247-1252, 1988.*
Nolet, S. et al., Biochimica et Biohysica Acta, 1089: 247-249, 1991.*
Xuan, J.W. et al., DNA & Cell Biology, 16: 627-638, 1997.*
Xuan, J.W. et al, Journal of Cellular Biochemistry 65: 172-185, 1997.*
Xuan, J.W., et al., J. Cell. Biochem., vol. 63, pp. 61-73, 1996.
Linard, C.G., et al., vol. 73, pp. 479-488, 1988.
Baijal-Gupta, M., et al., J. Endocrinology, vol. 165, pp. 425-433, 2000.
Garde, S.V., et al., Prostate, vol. 38, pp. 118-125, 1999.
Kele, P., et al., 26th European Peptide Symposium, J. Pept. Sci., vol. 6, Abstract S172, 2000.
Mbikay, M., et al. (DNA 6(1):23-29, 1987 (Gene Bank Accession No. AAA36635).
Makinen, M., et al. (Eur. J. Biochem. 264(2):407-414, 1999 (Gene Bank Accession No. CAB39325).
Akiyama, K., et al., Nippon Hoigaku Zasshi 39(2), pp. 181-186, 1985 (Gene Bank Accession No. 1209281A).

* cited by examiner

*Primary Examiner*—Alana M. Harris
*Assistant Examiner*—Anne L. Holleran
(74) *Attorney, Agent, or Firm*—Fay, Sharpe, Fagan, Minnich & McKee, LLP

(57) ABSTRACT

The invention provides pharmaceutical compositions and method for inhibiting growth of prostatic adenocarcinoma, stomach cancer, breast cancer, endometrial, ovarian or other cancers of epithelial secretion, or benign prostate hyperplasia (BPH). In one embodiment the pharmaceutical composition includes human rHuPSP94, antigenic portions thereof, and functionally equivalent polypeptides thereof. In another embodiment, the pharmaceutical composition includes a mixture of human rHuPSP94, antigenic portions thereof, and functionally equivalent polypeptides thereof and an anticancer drug which may be administered in an appropriate dosage form, dosage quantity and dosage regimen to a patient suffering from, for example of prostatic adenocarcinoma, stomach cancer, breast cancer, endometrial, ovarian or other cancers of epithelial secretion, benign prostate hyperplasia, or (BPH) gastrointestinal cancer. The anticancer drug of the latter mixture may be one selected from the group of drugs including mitomycin, idarubicin, cisplatin, 5-fluoro-uracil, methotrexate, adriamycin, daunomycin, taxol, taxol derivative, and mixtures thereof.

35 Claims, 30 Drawing Sheets

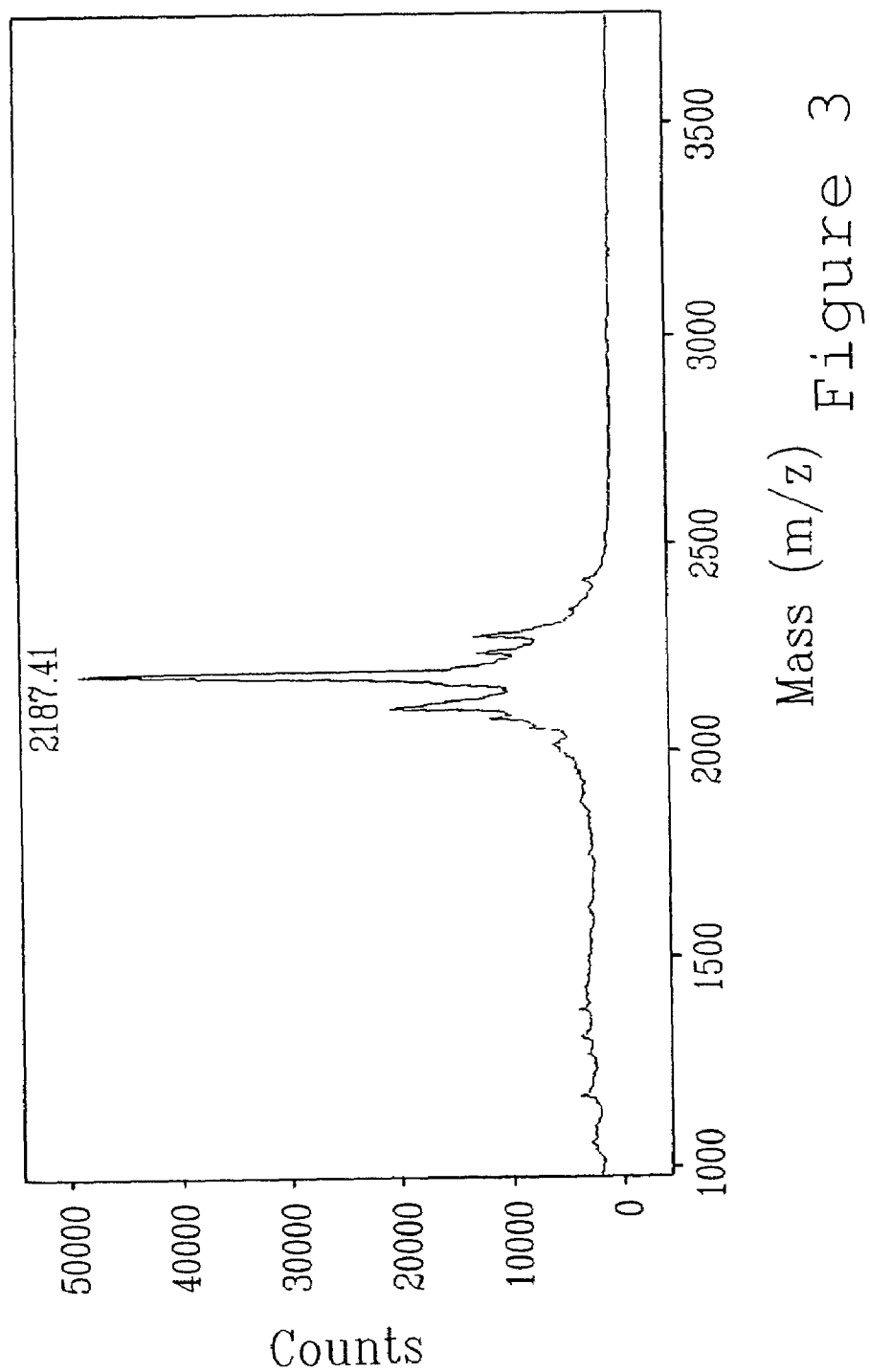

PHARMACEUTICAL PREPARATIONS AND METHODS FOR INHIBITING TUMORS

FIELD OF THE INVENTION

The present invention relates to pharmaceutical preparations (i.e., composition) for use as tumor suppressive agents for tumors arising from cancers such as prostatic adenocarcinoma, stomach cancer, breast cancer, endometrial and ovarian cancers, and benign prostate hyperplasia (BPH).

BACKGROUND OF THE INVENTION

The prostate gland, which is found exclusively in male mammals, produces several components of semen and blood and several regulatory peptides. The prostate gland comprises stroma and epithelium cells, the latter group consisting of columnar secretory cells and basal nonsecretory cells. A proliferation of these basal cells as well as stroma cells gives rise to benign prostatic hyperplasia (BPH), which is one common prostate disease. Another common prostate disease is prostatic adenocarcinoma (CaP), which is the most common of the fatal pathophysiological prostate cancers, and involves a malignant transformation of epithelial cells in the peripheral region of the prostate gland. Prostatic adenocarcinoma and benign prostatic hyperplasia are two common prostate diseases, which have a high rate of incidence in the aging human male population. Approximately one out of every four males above the age of 55 suffers from a prostate disease of some form or another. Prostate cancer is the second most common cause of cancer related death in elderly men, with approximately 96,000 cases diagnosed and about 26,000 deaths reported annually in the United States.

Studies of the various substances synthesized and secreted by normal, benign and cancerous prostates carried out in order to gain an understanding of the pathogenesis of the various prostate diseases reveal that certain of these substances may be used as immunohistochemical tumor markers in the diagnosis of prostate disease. The three predominant proteins or polypeptides secreted by a normal prostate gland are: (1) Prostatic Acid Phosphatase (PAP); (2) Prostate Specific Antigen (PSA); and, (3) Prostate Secretory Protein of 94 amino acids (PSP94), which is also known as Prostatic Inhibin Peptide (PIP), Human Seminal Plasma Inhibin (HSPI), or β-microseminoprotein (β-MSP), and which is hereinafter referred to as PSP94.

PSP94 is a simple non-glycosylated cysteine-rich protein, and constitutes one of three predominant proteins found in human seminal fluid along with Prostate Specific Antigen (PSA) and Prostate Acid Phosphatase (PAP). PSP94 has a molecular weight of 10.7 kiloDaltaon (kDa), and the complete amino acid sequence of this protein has already been determined (SEQ ID NO:1). The cDNA and gene for PSP94 have been cloned and characterized (Ulvsback, et al., Biochem. Biophys. Res. Comm., 164:1310, 1989; Green, et al., Biochem. Biophys. Res. Comm., 167:1184, 1990). Immunochemical and in situ hybridization techniques have shown that PSP94 is located predominantly in prostate epithelial cells. It is also present, however, in a variety of other secretory epithelial cells (Weiber, et al., Am. J. Pathol., 137:593, 1990). PSP94 has been shown to be expressed in prostate adenocarcinoma cell line, LNCap (Yang, et al., J. Urol., 160:2240, 1998). As well, an inhibitory effect of exogenous PSP94 on tumor cell growth has been observed both in vivo and in vitro (Garde, et al., Prostate, 22:225, 1993; Lokeshwar, et al., Cancer Res., 53:4855, 1993), suggesting that PSP94 could be a negative regulator for prostate carcinoma growth via interaction with cognate receptors on tumor cells.

Native PSP94 has been shown to have a therapeutic modality in treating hormone refractory prostate cancer (and potentially other prostate indications).

Metabolic and immunohistochemical studies have shown that the prostate is a major source of PSP94. PSP94 is involved in the feedback control of, and acts to suppress secretion of, circulating follicle-stimulating hormone (FSH) both in-vitro and in-vivo in adult male rats. PSP94 acts both at the pituitary as well as at the prostate site since both are provided with receptor sites for PSP94. It has been demonstrated to suppress the biosynthesis and release of FSH from the rat pituitary as well as to possibly affect the synthesis/secretion of an FSH-like peptide by the prostate. These findings suggest that the effects of PSP-94 on tumor growth in vivo, could be attributed to the reduction in serum FSH levels.

Both PSA and PAP have been studied as tumor markers in the detection of prostate disease, but since both exhibit elevated levels in prostates having benign prostatic hyperplasia (BPH), neither marker is specific and therefore they are of limited utility.

Recently, it has been shown that PSP94 concentrations in serum of patients with BPH or CaP are significantly higher than normal. The highest serum concentration of PSP94 observed in normal men is approximately 40 ng/ml, while in men with either BPH or CaP, serum concentrations of PSP94 have been observed in the range from 300–400 ng/ml. Because there exists some overlap in the concentrations of PSP94 in subjects having normal prostates and patients exhibiting either BPH or CaP, serum levels in and of themselves are of little value.

A major therapy in the treatment of prostate cancer is androgen-ablation. While most patients respond initially to this treatment, its effectiveness decreases over time, possibly because of the presence of a heterogenous population of androgen-dependant and androgen-independent cells to the androgen treatment, while any androgen insensitive cells present would continue to proliferate unabated.

Other forms of cancer, which are currently exacting a heavy toll on population are breast cancer in women and cancer of the gastrointestinal tract. Currently, the use of various cancer drugs such as mitomycin, idarubicin, cisplatin, 5-fluoro-uracil, methotrexate, adriamycin and daunomycin form part of the therapy for treating such cancers. One drawback to such a therapeutic treatment is the presence of adverse side effects due to the drugs in the concentration ranges required for effective treatment.

Accordingly, it would be advantageous to find a more effective means of arresting the growth of prostate, breast and gastrointestinal cancer cells and tumors, which may be used effectively against both androgen sensitive and androgen insensitive cells.

In previous work, described in U.S. Pat. No. 5,428,011, we provided pharmaceutical preparations (i.e., compositions) of native human seminal plasma PSP94 for inhibiting in-vitro and in-vivo cancerous prostate, gastrointestinal and breast tumors. The pharmaceutical preparations included native human seminal plasma PSP94 which could be administered in an appropriate dosage form, dosage quantity and dosage regimen to a patient suffering from prostate cancer. In another embodiment, the pharmaceutical preparation included a mixture of human seminal plasma PSP94 and an anticancer drug which may be administered in an appropriate dosage form, dosage quantity and dosage regimen to a patient suffering from, for example gastrointestinal cancer.

PSP94 sourced from human seminal fluid carries with it significant risk of contamination with infectious agents (e.g., HIV, hepatitis (a, b, or c), and other viruses and/or prions). Even with the use of harsh chemical treatment, total eradication of such agents cannot be guaranteed. Additionally, human seminal fluid is found in limited supply, thus making bulk production of PSP94 very difficult. Therefore, the acceptability of human or even xenogeneic sourced PSP94 may be very difficult for both the regulatory authorities and the marketplace.

Therefore, the use of recombinant technology for producing PSP94 would represent a significant advancement, as recombinant PSP94 could be produced both free of pathogens and in an unlimited supply. Furthermore, the material would be homogeneous from a single lot source, avoiding batch variation.

SUMMARY OF THE INVENTION

In its first aspect the present invention relates to a polypeptide or a polypeptide analog selected from the group consisting of the polypeptide as set forth in SEQ ID NO: 3, the polypeptide as set forth in SEQ ID NO: 4, the polypeptide as set forth in SEQ ID NO: 5, and the polypeptide as set forth in SEQ ID NO: 6, a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5. The polypeptide analog mentioned herein may be capable of inhibiting the growth of a tumor or more precisely may be capable of inhibiting the growth of prostatic adenocarcinoma, stomach cancer, breast cancer, endometrial, ovarian or other cancers of epithelial secretion, or benign prostate hyperplasia (BPH).

In a second aspect, the present invention relates to the use of a polypeptide or a polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), and the polypeptide as set forth in SEQ ID NO: 6 (polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5 and mixture(s) thereof, for inhibiting the growth of a tumor or more precisely for inhibiting the growth of prostatic adenocarcinoma, stomach cancer, breast cancer, endometrial, ovarian or other cancers of epithelial secretion, or benign prostate hyperplasia (BPH).

In one embodiment of the second aspect of the present invention, the polypeptide or polypeptide analog may be used with an anticancer drug, such as, for example, mitomycin, idarubicin, cisplatin, 5-fluoro-uracil, methotrexate, adriamycin, daunomycin, taxol (i.e., paclitaxel), taxol derivative (e.g.,docetaxel, taxane), and mixtures thereof.

In an additional embodiment of the second aspect of the present invention, the polypeptide or polypeptide analog may be used with a pharmaceutically acceptable carrier.

In a further embodiment of the second aspect of the present invention the polypeptide or polypeptide analog may be used with a time-release means such as, for example, liposomes and polysaccharides for effecting continual dosing of said polypeptide or polypeptide analog.

It other embodiments of the second aspect of the present invention, the polypeptide or polypeptide analog may be used with an anticancer drug and a pharmaceutically acceptable carrier, with an anticancer drug and a time-release means, with a pharmaceutically acceptable carrier and a time-release means, or with an anticancer drug, a pharmaceutically acceptable and a time-release means. Some examples of an anticancer drug, a pharmaceutically acceptable carrier and a time-release means are described herein.

In a third aspect, the present invention relates to a method for treating a patient with a tumor or more precisely with prostatic adenocarcinoma, stomach cancer, breast cancer, endometrial, ovarian or other cancers of epithelial secretion, or benign prostate hyperplasia (BPH), the method comprising administering to the patient a pharmaceutical composition comprising a polypeptide or polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), and the polypeptide as set forth in SEQ ID NO: 6 (polypeptide 76–94), a polypeptide analog selected from the group consisting of a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5 and mixtures thereof. The polypeptide analog mentioned herein may be capable of inhibiting the growth of a tumor or more precisely may be capable of inhibiting the growth of prostatic adenocarcinoma, stomach cancer, breast cancer, endometrial, ovarian or other cancers of epithelial secretion, or benign prostate hyperplasia (BPH).

The method for treating a patient as described above may result, for example, in the inhibition (e.g., reduction, control, atenuation, prohibition) of the growth of a tumor(s) in a patient suffering for example from prostatic adenocarcinoma, stomach cancer, breast cancer, endometrial, ovarian or other cancers of epithelial secretion, or benign prostate hyperplasia (BPH). The method described above may be performed, for example, by administering to the patient a pharmaceutical composition comprising a polypeptide, a polypeptide analog, or mixtures thereof of the present invention.

In one embodiment of the third aspect of the present invention, the polypeptide or polypeptide analog may be used with an anticancer drug, such as, for example, mitomycin, idarubicin, cisplatin, 5-fluoro-uracil, methotrexate, adriamycin, daunomycin, taxol (i.e., paclitaxel), taxol derivative (e.g.,docetaxel, taxane), and mixtures thereof.

In an additional embodiment of the third aspect of the present invention, the polypeptide or polypeptide analog may be used with a pharmaceutically acceptable carrier.

In a further embodiment of the third aspect of the present invention the polypeptide or polypeptide analog may be used with a time-release means such as for example, liposomes and polysaccharides for effecting continual dosing of said polypeptide or polypeptide analog.

It other embodiments of the third aspect of the present invention, the polypeptide or polypeptide analog may be used with an anticancer drug and a pharmaceutically acceptable carrier, with an anticancer drug and a time-release means, with a pharmaceutically acceptable carrier and a time-release means, or with an anticancer drug, a pharmaceutically acceptable and a time-release means. Some examples of an anticancer drug, a pharmaceutically acceptable carrier and a time-release means are described herein.

In a fourth aspect, the present invention relates to a method for treating a patient with a tumor or more precisely with prostatic adenocarcinoma, stomach cancer, breast cancer, endometrial, ovarian or other cancers of epithelial secretion, or benign prostate hyperplasia (BPH), the method comprising administering to the patient a pharmaceutical composition including a vector comprising the nucleotide sequence of SEQ ID NO: 9 and a pharmaceutically acceptable carrier or a pharmaceutical composition comprising a polynucleotide selected from the group consisting of a polynucleotide having at least 10 to 285 contiguous residues of SEQ ID NO: 9, and a polynucleotide having at least 10 to 50 contiguous residues of SEQ ID NO: 9, and a pharmaceutically acceptable carrier.

In one embodiment of the fourth aspect of the present invention, the vector or the polynucleotide may be used with an anticancer drug such as, for example, mitomycin, idarubicin, cisplatin, 5-fluoro-uracil, methotrexate, adriamycin, daunomycin, taxol (i.e., paclitaxel), taxol derivative (e.g., docetaxel, taxane), and mixtures thereof.

In an additional embodiment of the fourth aspect of the present invention, the vector or the polynucleotide may be used with a time-release means such as, for example, liposomes and polysaccharides for effecting continual dosing of said vector.

In further embodiment of the fourth aspect of the present invention, the vector or the polynucleotide may be used with an anticancer drug such as, for example, mitomycin, idarubicin, cisplatin, 5-fluoro-uracil, methotrexate, adriamycin, daunomycin, taxol (i.e., paclitaxel), taxol derivative (e.g., docetaxel, taxane), and mixtures thereof and with a time-release means such as, for example, liposomes and polysaccharides for effecting continual dosing of said vector or polynucleotide.

In a fifth aspect, the present invention relates to a pharmaceutical composition for inhibiting (e.g., recuding, controling, atenuating, prohibiting) the growth of a tumor in a patient suffering from prostatic adenocarcinoma, stomach cancer, breast cancer, endometrial, ovarian or other cancers of epithelial secretion, or benign prostate hyperplasia (BPH), comprising:

a) a polypeptide or a polypeptide analog selected from the group consisting of rHuPSP94 as set forth in SEQ ID NO: 2, the decapeptide as set forth in SEQ ID NO: 3, the polypeptide as set forth in SEQ ID NO: 4 (Polypeptide 7–21), the polypeptide as set forth in SEQ ID NO: 5 (PCK3145), the polypeptide as set forth in SEQ ID NO: 6 (Polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5, and mixture(s) thereof, and;
  b) an anticancer drug such as, for example, mitomycin, idarubicin, cisplatin, 5-fluoro-uracil, methotrexate, adriamycin, daunomycin, taxol, taxol derivative, and mixtures thereof.

In one embodiment of the fifth aspect of the present invention the pharmaceutical composition may further comprise a time-release means such as, for example, liposomes and polysaccharides for effecting continual dosing of the composition.

In a sixth aspect, the present invention relates to a pharmaceutical composition for inhibiting the growth of a tumor in a patient suffering from prostatic adenocarcinoma, stomach cancer, breast cancer, endometrial, ovarian or other cancers of epithelial secretion, or benign prostate hyperplasia (BPH), comprising:
  a) a polypeptide or polypeptide analog selected from the group consisting of rHuPSP94 as set forth in SEQ ID NO: 2, the decapeptide as set forth in SEQ ID NO: 3, the polypeptide as set forth in SEQ ID NO: 4 (Polypeptide 7–21), the polypeptide as set forth in SEQ ID NO: 5 (PCK3145), the polypeptide as set forth in SEQ ID NO: 6 (Polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5, and mixture(s) thereof, and;
  b) a pharmaceutically acceptable carrier.

In one embodiment of the sixth aspect of the present invention the pharmaceutical composition may further comprise a time-release means such as, for example, liposomes and polysaccharides for effecting continual dosing of the composition.

In a second embodiment of the sixth aspect of the present invention the pharmaceutical composition may further comprise an anticancer drug such as, for example, mitomycin, idarubicin, cisplatin, 5-fluoro-uracil, methotrexate, adriamycin, daunomycin, taxol, taxol derivative, and mixtures thereof.

In a third embodiment of the sixth aspect of the present invention, the pharmaceutical composition may further comprise a time-release means and an anticancer drug. Examples of time-release means and anticancer drug are described herein.

In a seventh aspect, the present invention relates to a pharmaceutical composition comprising:
  a) A polypeptide or polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), the polypeptide as set forth in SEQ ID NO: 6 (polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5; and a polypeptide analog having at least 50% of its amino acid sequence identical to the amino acid sequence set forth in SEQ ID NO: 5, and mixture(s) thereof, in a therapeutically effective amount, and;

b) an anticancer drug such as, for example, mitomycin, idarubicin, cisplatin, 5-fluoro-uracil, methotrexate, adriamycin, daunomycin, taxol, taxol derivative, and mixtures thereof in a therapeutically effective amount.

In one embodiment of the seventh aspect of the present invention the pharmaceutical composition may further comprise a time-release means such as, for example, liposomes and polysaccharides for effecting continual dosing of the composition.

In an eighth aspect, the present invention relates to a pharmaceutical composition comprising:

a) a polypeptide or polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), the polypeptide as set forth in SEQ ID NO: 6 (polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5, and mixture(s) thereof, in a therapeutically effective amount, and;

b) a pharmaceutically acceptable carrier.

In one embodiment of the eighth aspect of the present invention the pharmaceutical composition may further comprise a time-release means such as, for example, liposomes and polysaccharides for effecting continual dosing of the composition.

In a second embodiment of the eight aspect of the present invention, the pharmaceutical composition may further comprise an anticancer drug such as, for example, mitomycin, idarubicin, cisplatin, 5-fluoro-uracil, methotrexate, adriamycin, daunomycin, taxol, taxol derivative, and mixtures thereof.

In a third embodiment of the eight aspect of the present invention, the pharmaceutical composition may further comprise a time-release means and an anticancer drug. Examples of time-release means and anticancer drug are described herein.

In a ninth aspect, the present invention relates to a pharmaceutical composition for inhibiting (reducing, controling, atenuating, prohibiting) the growth of a tumor in a patient suffering from prostatic adenocarcinoma, stomach cancer, breast cancer, endometrial, ovarian or other cancers of epithelial secretion, or benign prostate hyperplasia (BPH), comprising a vector comprising the nucleotide sequence of SEQ ID NO: 9 and a pharmaceutically acceptable carrier, or a polynucleotide selected from the group consisting of a polynucleotide having at least 10 to 285 contiguous residues of SEQ ID NO: 9 and a polynucleotide having at least 10 to 50 contiguous residues of SEQ ID NO: 9, and a pharmaceutically acceptable carrier.

In one embodiment of the ninth aspect of the present invention, the pharmaceutical composition may further comprise an anticancer drug such as, for example, mitomycin, idarubicin, cisplatin, 5-fluoro-uracil, methotrexate, adriamycin, daunomycin, taxol (i.e., paclitaxel), taxol derivative (e.g.,docetaxel, taxane), and mixtures thereof.

In an tenth aspect, the present invention relates to a pharmaceutical composition for inhibiting the growth of a tumor in a patient, comprising a vector comprising the nucleotide sequence of SEQ ID NO: 9 and a pharmaceutically acceptable carrier, or a polynucleotide selected from the group consisting of a polynucleotide having at least 10 to 285 contiguous residues of SEQ ID NO: 9 and a polynucleotide having at least 10 to 50 contiguous residues of SEQ ID NO: 9, and a pharmaceutically acceptable carrier.

In one embodiment of the tenth aspect of the present invention, the pharmaceutical composition may further comprise an anticancer drug such as, for example, mitomycin, idarubicin, cisplatin, 5-fluoro-uracil, methotrexate, adriamycin, daunomycin, taxol (i.e., paclitaxel), taxol derivative (e.g.,docetaxel, taxane), and mixtures thereof.

In an eleventh aspect, the present invention relates to a method for treating patients with a disease characterized by elevated levels of FSH comprising administering a pharmaceutical composition in an appropriate dosage form, the pharmaceutical composition comprising a polypeptide or polypeptide analog selected from the group consisting of rHuPSP94 as set forth SEQ ID NO: 2, the decapeptide as set forth in SEQ ID NO: 3, the polypeptide as set forth in SEQ ID NO: 4, the polypeptide as set forth in SEQ ID NO: 5, and the polypeptide as set forth in SEQ ID NO: 6, a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ asset forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5, and mixtures thereof, and a pharmaceutically acceptable carrier in a human dose.

In a twelfth aspect, the present invention relates to the use of a polypeptide or a polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), and the polypeptide as set forth in SEQ ID NO: 6 (polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5 and mixture(s) thereof, for treating patients with a disease characterized by elevated levels of FSH.

The use of a polypeptide or a polypeptide analog selected from the group consisting of rHuPSP94 as set forth in SEQ ID NO: 2, the decapeptide as set forth in SEQ ID NO: 3, the polypeptide as set forth in SEQ ID NO: 4 (polypeptide 7–21), the polypeptide as set forth in SEQ ID NO: 5 (PCK3145), the polypeptide as set forth in SEQ ID NO: 6 (polypeptide 76–94), a polypeptide analog of at least five contiguous amino acids of SEQ ID NO: 2, of SEQ ID NO: 3, of SEQ ID NO: 4, of SEQ ID NO: 5, or of SEQ ID NO: 6, a polypeptide analog consisting of the amino acid sequence $X_1$ W Q $X_2$ D $X_1$ C $X_1$ $X_2$ C $X_2$ C $X_3$ $X_1$ $X_2$ as set forth in SEQ ID NO: 89, wherein $X_1$ is either glutamic acid (Glu), asparagine (Asn) or aspartic acid (Asp), $X_2$ is either threonine (Thr) or serine (Ser), and $X_3$ is either tyrosine (Tyr) or phenylalanine (Phe), a polypeptide analog comprising SEQ ID NO: 5 and having an addition of at least one amino acid to its amino-terminus, wherein said polypeptide analog comprising SEQ ID NO:5 is selected from the group consisting of SEQ ID NO: 59 to SEQ ID NO: 88, a polypeptide analog comprising SEQ ID NO: 5 and having an addition of at least one amino acid to its carboxy-terminus, wherein said polypeptide analog comprising SEQ ID NO:5 is selected from the group consisting of SEQ ID NO: 10 to SEQ ID NO: 58, a polypeptide analog comprising two to fifty units (or repeats) of SEQ ID NO: 5, a polypeptide analog comprising two to ten units (or repeats) of SEQ ID NO: 5, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), a polypeptide analog having at least 90% of its amino acid sequence identical to the amino acid sequence set forth in SEQ ID NO: 5, a polypeptide analog having at least 70% of its amino acid sequence identical to the amino acid sequence set forth in SEQ ID NO: 5, and a polypeptide analog having at least 50% of its amino acid sequence identical to the amino acid sequence set forth in SEQ ID NO: 5 and mixtures thereof for the manufacture of a medicament for the therapeutic treatment of prostatic adenocarcinoma, stomach cancer, breast cancer, endometrial, ovarian or other cancers of epithelial secretion, benign prostate hyperplasia (BPH) or a disease characterized by elevated levels of FSH.

In accordance with the present invention, rHuPSP94 may be used in a dosage range from about 10 micrograms/kg/day to about 4 milligrams/kg/day, in a dosage range from about 500 picograms/kg/day to about 1 milligram/kg/day, in a dosage range from about 5 nanograms/kg/day to about 10 micrograms/kg/day or in a dosage range from about 5 nanograms/kg/day to about 500 nanograms/kg/day.

In accordance with the present invention, the decapeptide as set forth in SEQ ID NO: 3, the polypeptide as set forth in SEQ ID NO: 4, the polypeptide as set forth in SEQ ID NO: 5, the polypeptide as set forth in SEQ ID NO: 6, and mixtures thereof may be used in a dosage range from about 100 nanograms/kg/day to about 4 milligrams/kg/day.

In accordance with the present invention, the anticancer drug may be mixed or not with a polypeptide or polypeptide analog or mixtures thereof or it may be given separately, by a different route, or even in a different administration schedule (e.g., a different time or day).

In accordance with the present invention administration of the composition may be performed by any suitable routes including administration by injection via the intra-muscular (IM), subcutaneous (SC), intra-dermal (ID), intra-venous (IV) or intra-peritoneal (IP) routes or administration at the mucosal membranes including the oral and nasal cavity membranes using any suitable means.

In accordance with the present invention, the composition may be used to treat gastrointestinal cancer.

It is known in the art that the proteins or polypeptides of the present invention may be made according to methods present in the art. The polypeptides of the present invention may be prepared for example, from bacterial cell extracts, or through the use of recombinant techniques. Polypeptides of the present invention may, for example, be produced by transformation (transfection, transduction, or infection) of a host cell with all or part of a rHuPSP94 (SEQ ID NO: 2), the decapeptide as set forth in SEQ ID NO: 3, the polypeptide as set forth in SEQ ID NO: 4 (polypeptide 7–21), the polypeptide as set forth in SEQ ID NO: 5 (PCK3145), and the polypeptide as set forth in SEQ ID NO: 6 (polypeptide 76–94) encoding DNA sequence in a suitable expression vehicle. Examples of suitable expression vehicles comprise for example, plasmids, viral particles, artificial chromosomes and phages. The entire expression vehicle, or a part thereof, may be integrated into the host cell genome. In some circumstances, it is desirable to employ an inducible expression vector.

Any of a wide variety of expression systems may be used to provide the recombinant protein. The precise host cell used is not critical to the invention. Polypeptides of the present invention may be produced in a prokaryotic host (e.g., *E. coli* or *B. subtilis*) or in a eukaryotic host (yeast e.g., *Saccharomyces* or *Pichia Pastoris*; mammalian cells, e.g., monkey COS cells, mouse 3T3 cells (Todaro G J and Green H., J. Cell Biol. 17: 299–313, 1963), Chinese Hamster Ovary cells (CHO) (Puck T T et al., J. Exp. Med. 108: 945–956, 1958), BHK, human kidney 293 cells (ATCC: CRL-1573), or human HeLa cells (ATCC:CCL-2); or insect cells).

In a yeast cell expression system such as *Pichia Pastoris* (*P. Pastoris*), DNA sequence encoding polypeptides of the present invention may be cloned into a suitable expression vector such as the pPIC9 vector (Invitrogen). Upon introduction of a vector containing the DNA sequence encoding all or part of the polypetides of the present invention into the *P. Pastoris* host cells, recombination event may occur for example in the AOX1 locus. Such recombination event may place the DNA sequence of the various polypetides of the present invention under the dependency of the AOX1 gene promoter. Successful insertion of a gene (DNA sequence) encoding polypeptides of the present invention may result in an expression of such polypeptides that is regulated and/or induced by methanol added in the growth media of the host cell (for reference see Buckholz, R. G. and Gleeson, M. A. G., Biotechnology, 9:1067–1072,1991; Cregg, J. M., et al., Biotechnology, 11:905–910, 1993; Sreekrishna, K., et al., J. Basic Microbiol., 28:265–278, 1988; Wegner, G. H., FEMS Microbiology Reviews, 87:279–284, 1990).

In mammalian host cells, a number of viral-based expression systems may be utilized. For example, in the event where an adenovirus is used as an expression vector for the polypeptides of the present invention, nucleic acid sequence may be ligated to an adenovirus transcription/translation control complex (e.g., the late promoter and tripartite leader sequence). This chimeric gene may be inserted into the adenovirus genome, for example, by in vitro or in vivo recombination. Insertion into a non-essential region of the viral genome (e.g., region E1 or E3) may result in a recombinant virus that is viable and capable of expressing polypeptides of the present invention in infected hosts.

Proteins and polypeptides of the present invention may also be produced by plant cells. Expression vectors such as cauliflower mosaic virus and tobacco mosaic virus and plasmid expression vectors (e.g., Ti plasmid) may be used for the expression of polypeptides in plant cells. Such cells are available from a wide range of sources (e.g., the American Type Culture Collection, Rockland, Md.). The methods of transformation or transfection and the choice of expression vehicle are of course to be chosen accordingly to the host cell selected.

In an insect cell expression system such as *Autographa californica* nuclear polyhedrosis virus (AcNPV), which grows in *Spodoptera frugiperda* cells, AcNPV may be used as a vector to express foreign genes. For example, DNA sequence coding for all or part of the polypeptides of the present invention may be cloned into non-essential regions of the virus (for example the polyhedrin gene) and placed under control of an AcNPV promoter, (e.g., the polyhedrin promoter). Successful insertion of a gene (i.e., DNA sequence) encoding polypeptides of the present invention may result in inactivation of the polyhedrin gene and production of non-occluded recombinant virus (i.e., virus lacking the proteinaceous coat encoded by the polyhedrin gene). These recombinant viruses may be used to infect *spodoptera frugiperda* cells in which the inserted gene is expressed.

In addition, a host cell may be chosen for its ability to modulate the expression of the inserted sequences, or to modify or process the gene product in a specific, desired fashion. Such modifications (e.g., glycosylation) and processing (e.g., cleavage) of protein products may be important for the function of the protein. Different host cells have characteristics and specific mechanisms for posttranslational processing and modification of proteins and gene products. Of course, cell lines or host systems may be chosen to ensure desired modification and processing of the foreign protein expressed. To this end, eukaryotic host cells that possess the cellular machinery for proper processing of the primary transcript, glycosylation, and phosphorylation of the gene product may be used. Such mammalian host cells comprise for example, but are not limited to, CHO, VERO, BHK, HeLa, COS, MDCK, 293, and 3T3.

Alternatively, polypeptides of the present invention may be produced by a stably transfected mammalian cell line. A number of vectors suitable for stable transfection of mammalian cells are available to the public; methods for constructing such cell lines are also publicly available. In one example, cDNA encoding the rHuPSP94 protein may be cloned into an expression vector that includes the dihydrofolate reductase (DHFR) gene. Integration of the plasmid and, therefore, DNA sequence of polypeptides of the present invention, into the host cell chromosome may be selected for by including methotrexate in the cell culture media. This selection may be accomplished in most cell types.

Specific initiation signals may also be required for the efficient translation of DNA sequences inserted in a suitable expression vehicle as described above. These signals may include the ATG initiation codon and adjacent sequences. For example, in the event where gene or cDNA encoding polypeptides of the present invention, would not have their own initiation codon and adjacent sequences, additional translational control signals may be needed. For example, exogenous translational control signals, including, perhaps, the ATG initiation codon, may be needed. It is known in the art that the initiation codon must be in phase with the reading frame of the polypeptide sequence to ensure proper translation of the desired polypeptide. Exogenous translational control signals and initiation codons may be of a variety of origins, including both natural and synthetic. The efficiency of expression may be enhanced by the inclusion of appropriate transcription enhancer elements, transcription terminators.

As may be appreciated, a number of modifications may be made to the polypeptides and fragments of the present invention without deleteriously affecting the biological activity of the polypeptides or fragments. Polypeptides of the present invention comprises for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular proterties, $2^{nd}$ Ed., T. E. Creighton, W. H. Freeman and Company, New-York, 1993).

Other type of polypeptide modification may comprises for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide. Polypeptides of the present invention comprise for example, biologically active mutants, variants, fragments, chimeras, and analogs; fragments encompass amino acid sequences having truncations of one or more amino acids, wherein the truncation may originate from the amino terminus (N-terminus), carboxy terminus (C-terminus), or from the interior of the protein. Analogs of the invention involve an insertion or a substitution of one or more amino acids. Variants, mutants, fragments, chimeras and analogs may have the biological property of polypeptides of the present invention which is to inhibit growth of prostatic adenocarcinoma, stomach cancer, breast cancer, endometrial, ovarian or other cancers of epithelial secretion, or benign prostate hyperplasia (BPH).

Example of substitutions may be those, which are conservative (i.e., wherein a residue is replaced by another of the same general type). As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same group as that of the amino acid be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA may also be made. For example, alternative residues include the omega amino acids of the formula $NH_2(CH_2)_nCOOH$ wherein n is 2–6. These are neutral nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that mutants or variants may be generated by substitutional mutagenesis and retain the biological activity of the polypeptides of the present invention. These variants have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as"conservative substitutions" are shown in table 1. If such substitutions result in a change not desired, then other type of substitutions, denominated "exemplary substitutions" in table 1, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:
(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and
(6) aromatic: Tryptophan (Trp), Tyrosine (Tyr), Phenylalanine (Phe)

Non-conservative substitutions will entail exchanging a member of one of these classes for another.

TABLE 1

Preferred amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Example of analogs of PCK3145 (SEQ ID NO: 5) exemplified by amino acid substitutions has been illustrated below.

```
                                              SEQ ID NO: 89
Position 1          5              10
PCK3145  E  W  Q  T  D  N  C  E  T  C  T  C
                                              15
                                        Y  E  T
         X1 W  Q  X2 D  X1 C  X1 X2 C  X2 C
                                        X3 X1 X2
```

For example, $X_1$ could be glutamic acid (i.e., glutamate) (Glu), aspartic acid (aspartate) (Asp), or asparagine (Asn), $X_2$ could be threonine (Thr) or serine (Ser) and $X_3$ could be tyrosine (Tyr) or phenylalanine (Phe).

Amino acids sequence insertions (e.g., additions) include amino and/or carboxyl-terminal fusions ranging in length from one residues to polypeptides containing a hundred or more residues, as well as intrasequence insertions of single or multiple amino acid residues. Other insertional variants include the fusion of the N- or C-terminus of the protein to a homologous or heterologous polypeptide forming a chimera. Chimeric polypeptides (i.e., chimeras, polypeptide analog) comprise sequence of the polypeptides of the present invention fused to homologous or heterologous sequence. Said homologous or heterologous sequence encompass those which, when formed into a chimera with the polypeptides of the present invention retain one or more biological or immunological properties. Examples of homologous sequences fused to PCK3145 (SEQ ID NO: 5) are illustrated below (1 to 79). Such homologous sequences are derived as it is the case for PCK3145, from rHuPSP94 (SEQ ID NO: 2).

| | | |
|---|---|---|
| 1) | EWQTDNCETCTCYETE | (SEQ ID NO: 10) |
| 2) | EWQTDNCETCTCYETEI | (SEQ ID NO: 11) |
| 3) | EWQTDNCETCTCYETEIS | (SEQ ID NO: 12) |
| 4) | EWQTDNCETCTCYETEISC | (SEQ ID NO: 13) |
| 5) | EWQTDNCETCTCYETEISCC | (SEQ ID NO: 14) |
| 6) | EWQTDNCETCTCYETEISCCT | (SEQ ID NO: 15) |
| 7) | EWQTDNCETCTCYETEISCCTL | (SEQ ID NO: 16) |
| 8) | EWQTDNCETCTCYETEISCCTLV | (SEQ ID NO: 17) |
| 9) | EWQTDNCETCTCYETEISCCTLVS | (SEQ ID NO: 18) |
| 10) | EWQTDNCETCTCYETEISCCTLVST | (SEQ ID NO: 19) |
| 11) | EWQTDNCETCTCYETEISCCTLVSTP | (SEQ ID NO: 20) |
| 12) | EWQTDNCETCTCYETEISCCTLVSTPV | (SEQ ID NO: 21) |
| 13) | EWQTDNCETCTCYETEISCCTLVSTPVG | (SEQ ID NO: 22) |

-continued

| | | |
|---|---|---|
| 14) | EWQTDNCETCTCYETEISCCTLVSTPVGY | (SEQ ID NO: 23) |
| 15) | EWQTDNCETCTCYETEISCCTLVSTPVGYD | (SEQ ID NO: 24) |
| 16) | EWQTDNCETCTCYETEISCCTLVSTPVGYDK | (SEQ ID NO: 25) |
| 17) | EWQTDNCETCTCYETEISCCTLVSTPVGYDKD | (SEQ ID NO: 26) |
| 18) | EWQTDNCETCTCYETEISCCTLVSTPVGYDKDN | (SEQ ID NO: 27) |
| 19) | EWQTDNCETCTCYETEISCCTLVSTPVGYDKDNC | (SEQ ID NO: 28) |
| 20) | EWQTDNCETCTCYETEISCCTLVSTPVGYDKDNCQ | (SEQ ID NO: 29) |
| 21) | EWQTDNCETCTCYETEISCCTLVSTPVGYDKDNCQR | (SEQ ID NO: 30) |
| 22) | EWQTDNCETCTCYETEISCCTLVSTPVGYDKDNCQRI | (SEQ ID NO: 31) |
| 23) | EWQTDNCETCTCYETEISCCTLVSTPVGYDKDNCQRIF | (SEQ ID NO: 32) |
| 24) | EWQTDNCETCTCYETEISCCTLVSTPVGYDKDNCQRIFK | (SEQ ID NO: 33) |
| 25) | EWQTDNCETCTCYETEISCCTLVSTPVGYDKDNCQRIFKK | (SEQ ID NO: 34) |
| 26) | EWQTDNCETCTCYETEISCCTLVSTPVGYDKDNCQRIFKKE | (SEQ ID NO: 35) |
| 27) | EWQTDNCETCTCYETEISCCTLVSTPVGYDKDNCQRIFKKED | (SEQ ID NO: 36) |
| 28) | EWQTDNCETCTCYETEISCCTLVSTPVGYDKDNCQRIFKKEDC | (SEQ ID NO: 37) |
| 29) | EWQTDNCETCTCYETEISCCTLVSTPVGYDKDNCQRIFKKEDCK | (SEQ ID NO: 38) |
| 30) | EWQTDNCETCTCYETEISCCTLVSTPVGYDKDNCQRIFKKEDCKY | (SEQ ID NO: 39) |
| 31) | EWQTDNCETCTCYETEISCCTLVSTPVGYDKDNCQRIFKKEDCKYI | (SEQ ID NO: 40) |
| 32) | EWQTDNCETCTCYETEISCCTLVSTPVGYDKDNCQRIFKKEDCKYIV | (SEQ ID NO: 41) |
| 33) | EWQTDNCETCTCYETEISCCTLVSTPVGYDKDNCQRIFKKEDCKYIVV | (SEQ ID NO: 42) |
| 34) | EWQTDNCETCTCYETEISCCTLVSTPVGYDKDNCQRIFKKEDCKYIVVE | (SEQ ID NO: 43) |
| 35) | EWQTDNCETCTCYETEISCCTLVSTPVGYDKDNCQRIFKKEDCKYIVVEK | (SEQ ID NO: 44) |
| 36) | EWQTDNCETCTCYETEISCCTLVSTPVGYDKDNCQRIFKKEDCKYIVVEKK | (SEQ ID NO: 45) |
| 37) | EWQTDNCETCTCYETEISCCTLVSTPVGYDKDNCQRIFKKEDCKYIVVEKKD | (SEQ ID NO: 46) |
| 38) | EWQTDNCETCTCYETEISCCTLVSTPVGYDKDNCQRIFKKEDCKYIVVEKKDP | (SEQ ID NO: 47) |
| 39) | EWQTDNCETCTCYETEISCCTLVSTPVGYDKDNCQRIFKKEDCKYIVVEKKDPK | (SEQ ID NO: 48) |
| 40) | EWQTDNCETCTCYETEISCCTLVSTPVGYDKDNCQRIFKKEDCKYIVVEKKDPKK | (SEQ ID NO: 49) |
| 41) | EWQTDNCETCTCYETEISCCTLVSTPVGYDKDNCQRIFKKEDCKYIVVEKKDPKKT | (SEQ ID NO: 50) |
| 42) | EWQTDNCETCTCYETEISCCTLVSTPVGYDKDNCQRIFKKEDCKYIVVEKKDPKKTC | (SEQ ID NO: 51) |
| 43) | EWQTDNCETCTCYETEISCCTLVSTPVGYDKDNCQRIFKKEDCKYIVVEKKDPKKTCS | (SEQ ID NO: 52) |
| 44) | EWQTDNCETCTCYETEISCCTLVSTPVGYDKDNCQRIFKKEDCKYIVVEKKDPKKTCSV | (SEQ ID NO: 53) |
| 45) | EWQTDNCETCTCYETEISCCTLVSTPVGYDKDNCQRIFKKEDCKYIVVEKKDPKKTCSVS | (SEQ ID NO: 54) |
| 46) | EWQTDNCETCTCYETEISCCTLVSTPVGYDKDNCQRIFKKEDCKYIVVEKKDPKKTCSVSE | (SEQ ID NO: 55) |
| 47) | EWQTDNCETCTCYETEISCCTLVSTPVGYDKDNCQRIFKKEDCKYIVVEKKDPKKTCSVSEW | (SEQ ID NO: 56) |
| 48) | EWQTDNCETCTCYETEISCCTLVSTPVGYDKDNCQRIFKKEDCKYIVVEKKDPKKTCSVSEWI | (SEQ ID NO: 57) |
| 49) | EWQTDNCETCTCYETEISCCTLVSTPVGYDKDNCQRIFKKEDCKYIVVEKKDPKKTCSVSEWII | (SEQ ID NO: 58) |
| 50) | SCYFIPNEGVPGDSTRKCMDLKGNKHPINSEWQTDNCETCTCYET | (SEQ ID NO: 88) |
| 51) | CYFIPNEGVPGDSTRKCMDLKGNKHPINSEWQTDNCETCTCYET | (SEQ ID NO: 87) |
| 52) | YFIPNEGVPGDSTRKCMDLKGNKHPINSEWQTDNCETCTCYET | (SEQ ID NO: 86) |
| 53) | FIPNEGVPGDSTRKCMDLKGNKHPINSEWQTDNCETCTCYET | (SEQ ID NO: 85) |

-continued

| | | |
|---|---|---|
| 54) | IPNEGVPGDSTRKCMDLKGNKHPINSEWQTDNCETCTCYET | (SEQ ID NO: 84) |
| 55) | PNEGVPGDSTRKCMDLKGNKHPINSEWQTDNCETCTCYET | (SEQ ID NO: 83) |
| 56) | NEGVPGDSTRKCMDLKGNKHPINSEWQTDNCETCTCYET | (SEQ ID NO: 82) |
| 57) | EGVPGDSTRKCMDLKGNKHPINSEWQTDNCETCTCYET | (SEQ ID NO: 81) |
| 58) | GVPGDSTRKCMDLKGNKHPINSEWQTDNCETCTCYET | (SEQ ID NO: 80) |
| 59) | VPGDSTRKCMDLKGNKHPINSEWQTDNCETCTCYET | (SEQ ID NO: 79) |
| 60) | PGDSTRKCMDLKGNKHPINSEWQTDNCETCTCYET | (SEQ ID NO: 78) |
| 61) | GDSTRKCMDLKGNKHPINSEWQTDNCETCTCYET | (SEQ ID NO: 77) |
| 62) | DSTRKCMDLKGNKHPINSEWQTDNCETCTCYET | (SEQ ID NO: 76) |
| 63) | STRKCMDLKGNKHPINSEWQTDNCETCTCYET | (SEQ ID NO: 75) |
| 64) | TRKCMDLKGNKHPINSEWQTDNCETCTCYET | (SEQ ID NO: 74) |
| 65) | RKCMDLKGNKHPINSEWQTDNCETCTCYET | (SEQ ID NO: 73) |
| 66) | KCMDLKGNKHPINSEWQTDNCETCTCYET | (SEQ ID NO: 72) |
| 67) | CMDLKGNKHPINSEWQTDNCETCTCYET | (SEQ ID NO: 71) |
| 68) | MDLKGNKHPINSEWQTDNCETCTCYET | (SEQ ID NO: 70) |
| 69) | DLKGNKHPINSEWQTDNCETCTCYET | (SEQ ID NO: 69) |
| 70) | LKGNKHPINSEWQTDNCETCTCYET | (SEQ ID NO: 68) |
| 71) | KGNKHPINSEWQTDNCETCTCYET | (SEQ ID NO: 67) |
| 72) | GNKHPINSEWQTDNCETCTCYET | (SEQ ID NO: 66) |
| 73) | NKHPINSEWQTDNCETCTCYET | (SEQ ID NO: 65) |
| 74) | KHPINSEWQTDNCETCTCYET | (SEQ ID NO: 64) |
| 75) | HPINSEWQTDNCETCTCYET | (SEQ ID NO: 63) |
| 76) | PINSEWQTDNCETCTCYET | (SEQ ID NO: 62) |
| 77) | INSEWQTDNCETCTCYET | (SEQ ID NO: 61) |
| 78) | NSEWQTDNCETCTCYET | (SEQ ID NO: 60) |
| 79) | SEWQTDNCETCTCYET | (SEQ ID NO: 59) |

Other type of chimera generated by homologous fusion includes new polypeptides formed by the repetition of two or more polypeptides of the present invention. The number of repeat may be, for example, between 2 and 50 units (i.e., repeats). In some instance, it may be useful to have a new polypeptide with a number of repeat greater than 50. Examples of new polypeptides formed by the repetition of PCK3145 (SEQ ID NO: 5) are illustrated below (80 to 82). In some instance, SEQ ID NO: 5 units may be separated by a linker or an adaptor of variable length.

| | | |
|---|---|---|
| 80) | EWQTDNCETCTCYETEEWQTDNCETCTCYETE | (SEQ ID NO: 90) |
| 81) | EWQTDNCETCTCYETEEWQTDNCETCTCYETEEWQTDNCETCTCYETE | (SEQ ID NO: 91) |
| 82) | EWQTDNCETCTCYETEEWQTDNCETCTCYETEEWQTDNCETCTCYETEEWQTDNCETCTCYETE | (SEQ ID NO: 92) |

Heterologous fusion includes new polypeptides made by the fusion of polypeptides of the present invention with heterologous polypeptides. Such polypeptides may include but are not limited to bacterial polypeptides (e.g., betalactamase, glutathione-S-transferase, or an enzyme encoded by the *E. coli* trp locus), yeast protein, viral proteins, phage proteins, bovine serum albumin, chemotactic polypeptides, immunoglobulin constant region (or other immunoglobulin regions), albumin, or ferritin.

Other type of polypeptide modification includes amino acids sequence deletions (e.g., truncations). Those generally range from about 1 to 30 residues, more preferably about 1 to 10 residues and typically about 1 to 5 residues.

A host cell transformed or transfected with nucleic acids encoding the polypeptides of the present invention (i.e., vector containing the DNA sequence of the polypeptides of the present invention) or chimeric proteins formed with the polypeptides of the present invention are also encompassed by the invention. Any host cell, which produces a polypeptide analog, mutant, variant, fragment, or chimera having at least one of the biological properties of the present invention is encompassed by the present invention. For example, such host cell may include bacterial, yeast, plant, insect or mammalian cells. In addition, the polypeptides of the present invention may be produced in transgenic animals. Transformed or transfected host cells and transgenic animals may be obtained using materials and methods that are routinely available to one skilled in the art.

DEFINITIONS

General Molecular Biology

Unless otherwise indicated, the recombinant DNA techniques utilized in the present invention are standard procedures, known to those skilled in the art. Example of such techniques are explained in the literature in sources such as J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1–4, IRL Press (1995 and 1996), and F. M. Ausubel et al. (editors), Current Protocols in Molecular Biology, Greene Pub. Associates and Wiley-Interscience (1988, including all updates until present) and are incorporated herein by reference.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "polypeptide analog" relates to mutants, variants, chimeras, fusions, deletions, additions and any other type of modifications made relative to a given polypeptide.

As used herein, the term "homologous" sequence relates to nucleotide or amino acid sequence derived from the rHuPSP94 DNA sequence or polypeptide.

As used herein, the term "heterologous" sequence relates to DNA sequence or amino acid sequence of a heterologous polypeptide and includes sequence other than that of PSP94.

As used herein, the term "tumor" relates to solid or non-solid tumors, metastasic or non-metastasic tumors, tumors of different tissue origin including, but not limited to, tumors originating in the liver, lung, brain, lymph node, bone marrow, adrenal gland, breast, colon, pancreas, prostate, stomach, or reproductive tract (cervix, ovaries, endometrium etc.). The term "tumor" as used herein, refers also to all neoplastic cell growth and proliferation, whether malignant or benign, and all pre-cancerous and cancerous cells and tissues.

As used herein, the term "polysaccharide" refers to a substance made of two or more saccharide unit and comprise, for example, chitosan, pectin, chondroitin sulfate, cyclodextrin, dextrans, guar gum, inulin, amylose, and locust bean gum.

As used herein, the term "vector" refers to an autonomously replicating DNA or RNA molecule into which foreign DNA or RNA fragments are inserted and then propagated in a host cell for either expression or amplification of the foreign DNA or RNA molecule. The term <<vector>> comprises and is not limited to a plasmid (e.g., linearized or not) that can be used to transfer DNA sequences from one organism to another.

As used herein, the term "time-release encapsulation means" refers to controlled or sustained release obtained when a pharmaceutical composition is formulated, for example, with polysaccharides, biocompatible polymers, other polymeric matrices, capsules, microcapsules, microparticles, bolus preparations, osmotic pumps, diffusion devices, liposomes, liposheres, dry powders, or transdermal delivery systems. Other controlled release compositions of the present invention include liquids that, upon administration to a mammal, form a solid or a gel in situ. Furthermore, the term "time-release encapsulation means" or "time-release means" comprises a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Mutants, Variants and Analogs Proteins

Mutant polypeptides will possess one or more mutations, which are deletions (e.g., truncations), insertions (e.g., additions), or substitutions of amino acid residues. Mutants can be either naturally occurring (that is to say, purified or isolated from a natural source) or synthetic (for example, by performing site-directed mutagenesis on the encoding DNA or made by other synthetic methods such as chemical synthesis). It is thus apparent that the polypeptides of the invention can be either naturally occurring or recombinant (that is to say prepared from the recombinant DNA techniques).

A protein at least 50% identical, as determined by methods known to those skilled in the art (for example, the methods described by Smith, T. F. and Waterman M. S. (1981) Ad. Appl. Math., 2:482–489, or Needleman, S. B. and Wunsch, C. D. (1970) J. Mol. Biol., 48: 443–453), to those polypeptides of the present invention are included in the invention, as are proteins at least 70% or 80% and more preferably at least 90% identical to the protein of the present invention. This will generally be over a region of at least 5, preferably at least 20 contiguous amino acids.

"Variant" as the term used herein, is a polynucleotide or polypeptide that differs from reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion and truncations in the polypeptide encoded by the reference sequence, as discussed herein. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid by one or more substitutions, additions, deletions, or any combination therefore. A substituted or inserted amino acid residue may or may not be one encoded by the genetic code. A variant polynuclotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Amino acid sequence variants may be prepared by introducing appropriate nucleotide changes into DNA, or by in vitro synthesis of the desired polypeptide. Such variant include, for example, deletions, insertions, or substitutions of residues within the amino acid sequence. A combination of deletion, insertion and substitution can be made to arrive at the final construct, provided that the final protein product possesses the desired characteristics. The amino acid changes also may alter posttranslational processes such as changing the number or position of the glycocylation sites, altering the membrane anchoring characteristics, altering the intra-cellular location by inserting, deleting or otherwise affecting the transmembrane sequence of the native protein, or modifying its susceptibility to proteolytic cleavage.

It is to be understood herein, that if a "range" or "group" of substances (e.g. amino acids), substitutents or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a pressure greater than atmospheric, this is to be understood as specifically incorporating herein each and every individual pressure state, as well as sub-range, above atmospheric, such as for example 2 psig, 5 psig, 20 psig, 35.5 psig, 5 to 8 psig, 5 to 35, psig 10 to 25 psig, 20 to 40 psig, 35 to 50 psig, 2 to 100 psig, etc.;

with respect to a temperature greater than 100° C., this is to be understood as specifically incorporating herein each and every individual temperature state, as well as sub-range, above 100° C., such as for example 101° C., 105° C. and up, 110° C. and up, 115° C. and up, 110 to 135° C., 115° C. to 135° C., 102° C. to 150° C., up to 210° C., etc.;

with respect to a temperature lower than 100° C., this is to be understood as specifically incorporating herein each and every individual temperature state, as well as sub-range, below 100° C., such as for example 15° C. and up, 15° C. to 40° C., 65° C. to 95° C., 95° C. and lower, etc.;

with respect to residence or reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

with respect to polypeptides, a polypeptide analog consisting of at least five contiguous amino acids of a particular sequence is to be understood as specifically incorporating each and every individual possibility, such as for example, a polypeptide analog consisting of amino acids 1 to 5, a polypeptide analog consisting of amino acids 2 to 6, a polypeptide analog consisting of amino acids 3 to 7, a polypeptide analog consisting of amino acids 6 to 10, a polypeptide analog consisting of amino acids 9 to 13, a polypeptide analog consisting of amino acids 36 to 40, a polypeptide analog consisting of amino acids 90 to 94, etc.

with respect to polypeptides, a polypeptide analog comprising a particular sequence and having an addition of at least one amino acid to its amino-terminus is to be understood as specifically incorporating each and every individual possibility, such as for example, a polypeptide analog having an addition of one amino acid to its amino-terminus, a polypeptide analog having an addition of two amino acid to its amino-terminus, a polypeptide analog having an addition of three amino acid to its amino-terminus, a polypeptide analog having an addition of ten amino acid to its amino-terminus, a polypeptide analog having an addition of eighteen amino acid to its amino-terminus, a polypeptide analog having an addition of forty amino acid to its amino-terminus, a polypeptide analog having an addition of two hundred amino acid to its amino-terminus, etc.

with respect to polypeptides, a polypeptide analog comprising a particular sequence and having an addition of at least one amino acid to its carboxy-terminus is to be understood as specifically incorporating each and every individual possibility, such as for example, a polypeptide analog having an addition of one amino acid to its carboxy-terminus, a polypeptide analog having an addition of two amino acid to its carboxy-terminus, a polypeptide analog having an addition of five amino acid to its carboxy-terminus, a polypeptide analog having an addition of twenty amino acid to its carboxy-terminus, a polypeptide analog having an addition of fifty-three amino acid to its carboxy-terminus, a polypeptide analog having an addition of three hundred amino acid to its carboxy-terminus, etc.

with respect to polypeptides, a polypeptide analog comprising two to fifty units of a particular sequence is to be understood as specifically incorporating each and every individual possibility, such as for example, a polypeptide analog comprising two units of that particular sequence, a polypeptide analog comprising three units of that particular sequence, a polypeptide analog comprising six units of that particular sequence, a polypeptide analog comprising thirteen units of that particular sequence, a polypeptide analog comprising thirty-five units of that particular sequence, a polypeptide analog comprising fifty units of that particular sequence, etc.

with respect to polypeptides, a polypeptide analog comprising two to ten units of a particular sequence is to be understood as specifically incorporating each and every individual possibility, such as for example, a polypeptide analog comprising two units of that particular sequence, a polypeptide analog comprising three units of that particular sequence, a polypeptide analog comprising four units of that particular sequence, a polypeptide analog comprising five units of that particular sequence, a polypeptide analog comprising six units of that particular sequence, a polypeptide analog comprising seven units of that particular sequence, a polypeptide analog comprising eight units of that particular sequence, a polypeptide analog comprising nine units of that particular sequence, and a polypeptide analog comprising ten units of that particular sequence.

with respect to polypeptides, a polypeptide analog consisting of a sequence of from two to fourteen amino acid units wherein the amino acid units are selected from the group of amino acid units of SEQ ID NO: 5 consisting of glutamic acid (Glu), tryptophan (Trp), glutamine (Gln), threonine (Thr), aspartic acid (Asp), asparagine (Asn), cysteine (Cys), or tyrosine (Tyr), is to be understood as specifically incorporating each and every individual possibility, such as for example, a polypeptide analog of two amino acid units wherein the amino acids are sequentially; Glu and Trp, a polypeptide analog of two amino acid units wherein the amino acids are sequentially; Trp and Glu, a polypeptide analog of three amino acid units wherein the amino acids are sequentially; Trp, Glu, Trp, a polypeptide analog of three amino acid units wherein the amino acids are sequentially; Trp, Trp, Trp, a polypeptide analog of three amino acid units wherein the amino acids are sequentially; Glu, Glu, Trp, a polypeptide analog of three amino acid units wherein the amino acids are, independently of the order; Tyr, Asp, Glu, a polypeptide analog of three amino acid units wherein the amino acids are, independently of the order; Thr, Asp, Asn, a polypeptide analog of three amino acid units wherein the amino acids are, independently of the order; Thr, Thr, Asn, a polypeptide analog of four amino acid units wherein the amino acids are, independently of the order; Glu, Gln, Cys, Asn, a polypeptide analog of four amino acid units wherein the amino acids are, independently of the order; Gln, Gln Cys, Trp, a polypeptide analog of four amino acid units wherein the amino acids are, Cys, Cys, Cys, Cys, a polypeptide analog of fourteen amino acid units wherein the amino acids are, independently of the order; Asn, Asp, Glu, Gln, Trp, Cys, Tyr, Thr, Thr, Asp, Asn, Gln, Thr, Cys, a polypeptide analog of fourteen amino acid units wherein the amino acids are, independently of the order; Asp, Asp, Asp, Asp, Trp, Cys, Cys, Trp, Thr, Thr, Thr, Thr, Thr, Cys, a polypeptide analog of fourteen amino acid units wherein the amino acids are, independently of the order; Tyr, Tyr, Tyr, Tyr, Tyr, Tyr, Tyr, Tyr, Tyr, Tyr, Tyr, Tyr, Tyr, Tyr, etc.

with respect to polypeptides, a polypeptide analog having at least 90% of its amino acid sequence identical to a particular amino acid sequence is to be understood as specifically incorporating each and every individual possibility (excluding 100%), such as for example, a polypeptide analog having 90% of its amino acid sequence identical to that particular amino acid sequence, a polypeptide analog having 91% of its amino acid sequence identical to that particular amino acid sequence, a polypeptide analog having 93% of its amino acid sequence identical to that particular amino acid sequence, a polypeptide analog having 97% of its amino acid sequence identical to that particular amino acid sequence, a polypeptide analog having 99% of its amino acid sequence identical to that particular amino acid sequence, etc.

with respect to polypeptides, a polypeptide analog having at least 70% of its amino acid sequence identical to a particular amino acid sequence is to be understood as specifically incorporating each and every individual possibility (excluding 100%), such as for example, a polypeptide analog having 70% of its amino acid sequence identical to that particular amino acid sequence, a polypeptide analog having 71% of its amino acid sequence identical to that particular amino acid sequence, a polypeptide analog having 73% of its amino acid sequence identical to that particular amino acid sequence, a polypeptide analog having 88% of its amino acid sequence identical to that particular amino acid sequence, a polypeptide analog having 97% of its amino acid sequence identical to that particular amino acid sequence, a polypeptide analog having 99% of its amino acid sequence identical to that particular amino acid sequence, etc.

with respect to polypeptides, a polypeptide analog having at least 50% of its amino acid sequence identical to a particular amino acid sequence is to be understood as specifically incorporating each and every individual possibility (excluding 100%), such as for example, a polypeptide analog having 50% of its amino acid sequence identical to that particular amino acid sequence, a polypeptide analog having 51% of its amino acid sequence identical to that particular amino acid sequence, a polypeptide analog having 54% of its amino acid sequence identical to that particular amino acid sequence, a polypeptide analog having 66% of its amino acid sequence identical to that particular amino acid sequence, a polypeptide analog having 70% of its amino acid sequence identical to that particular amino acid sequence, a polypeptide analog having 79% of its amino acid sequence identical to that particular amino acid sequence, a polypeptide analog having 82% of its amino acid sequence identical to that particular amino acid sequence, a polypeptide analog having 99% of its amino acid sequence identical to that particular amino acid sequence, etc.

and similarly with respect to other parameters such as low pressures, concentrations, elements, etc . . .

It is also to be understood herein that "g" or "gm" is a reference to the gram weight unit; that "C" is a reference to the Celsius temperature unit; and "psig" is a reference to "pounds per square inch gauge".

BRIEF DESCRIPTION OF THE DRAWINGS

FIG. 3 depicts mass spectrometry analysis of polypeptide 76–94 (SEQ ID NO: 6).

Figure 23:
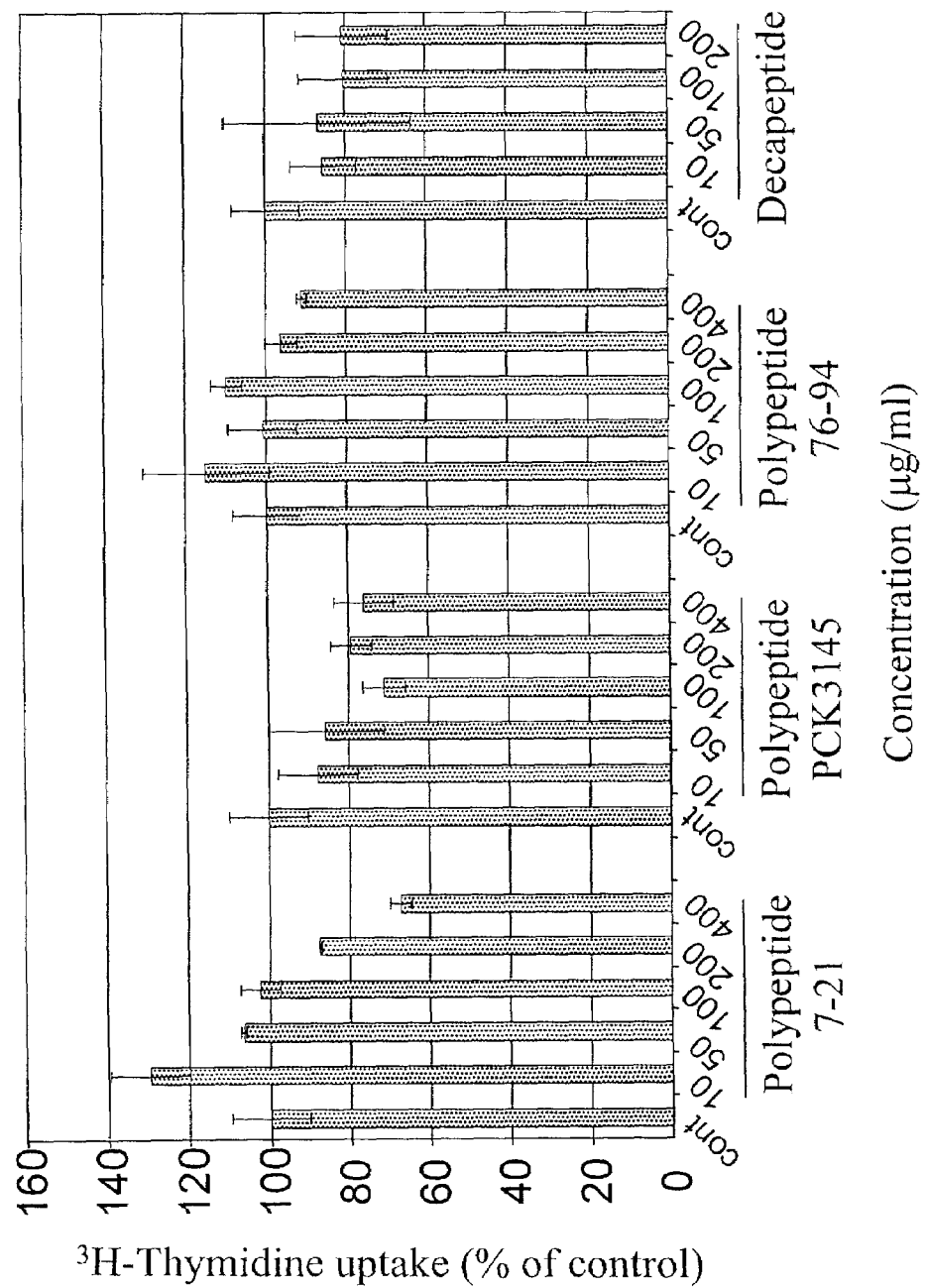

FIG. 23 is a graph depicting the in vitro inhibitory activity of decapeptide as set forth in SEQ ID NO: 3, polypeptide 7–21 as set forth in SEQ ID NO: 4, polypeptide PCK3145 as set forth in SEQ ID NO: 5, or polypeptide 76–94 as set forth in SEQ ID NO: 6 on PC-3 cells, measured by [$^3$H]-Thymidine uptake assay.

Figure 24:
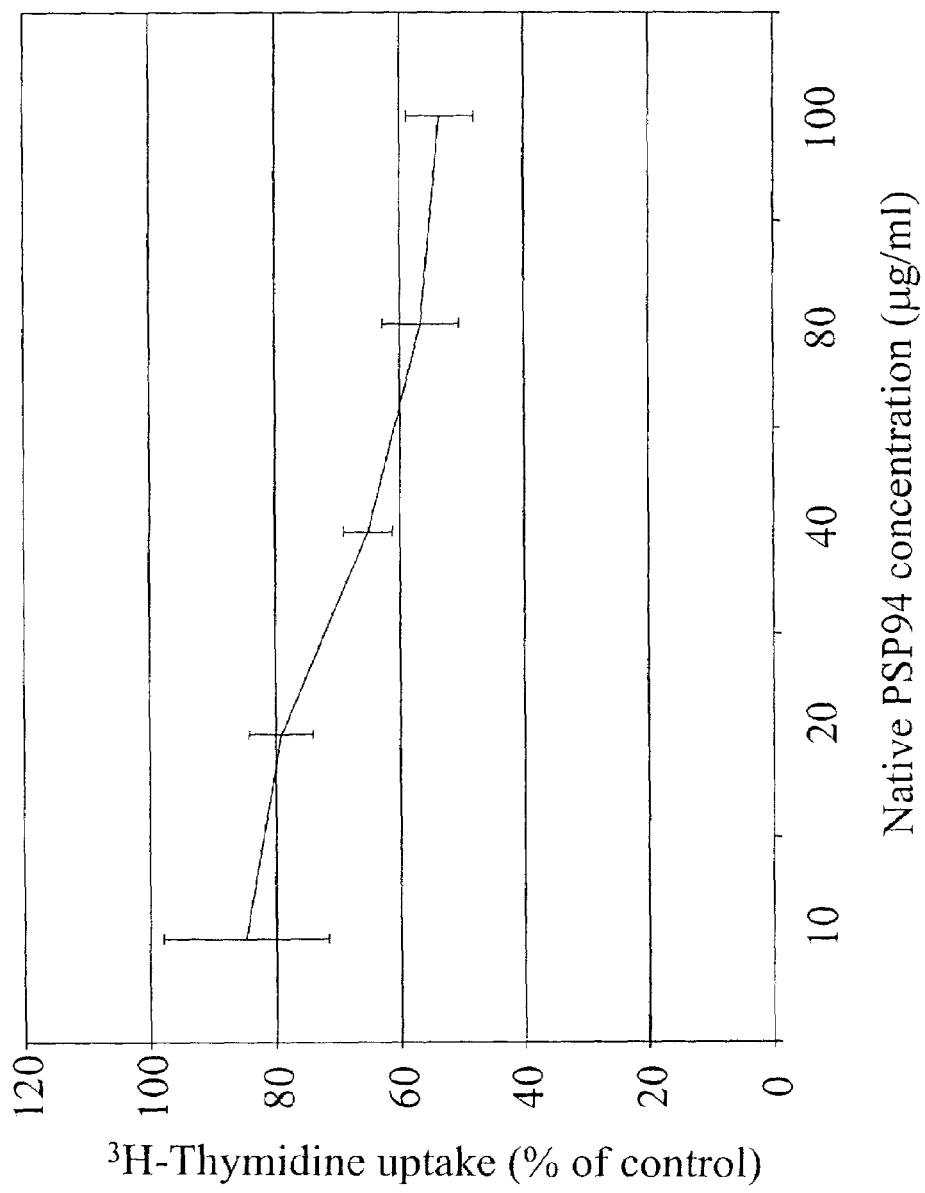

FIG. 24 is a graph depicting the in vitro inhibitory activity of native PSP94 (SEQ ID NO: 1) on PC-3 cells after 72 hours treatment, measured by [$^3$H]-Thymidine uptake assay.

Figure 25:
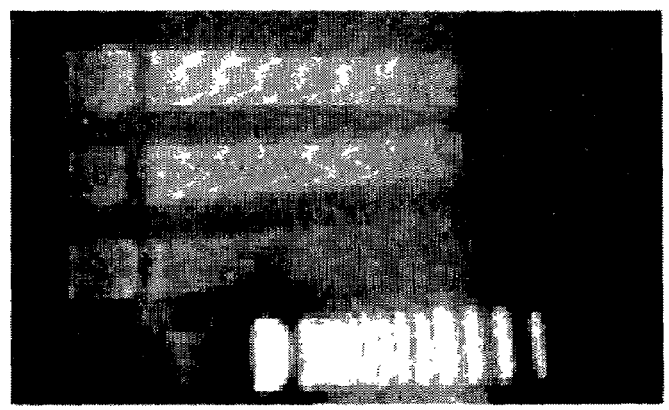

FIG. 25 depicts a gel showing DNA fragmentation following treatment of PC-3 cells with PCK3145 (SEQ ID NO: 5) or doxorubicin.

Figure 26:
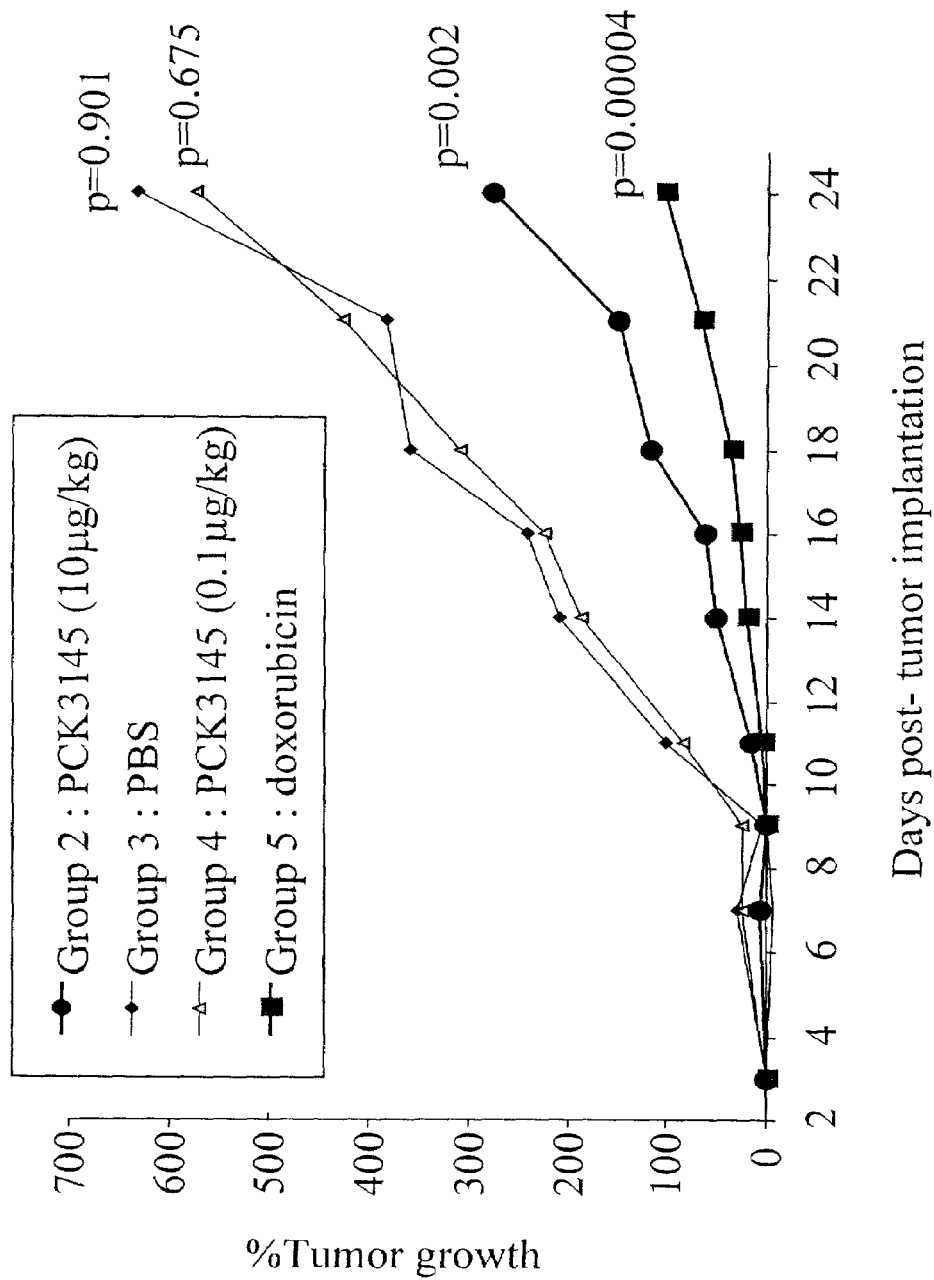

FIG. 26 is a graph depicting the in vivo inhibitory activity of PCK3145 (SEQ ID NO: 5) (0.1 µg/kg/day and 10 µg/kg/day) against human PC-3 tumor xenografted in nude mice.

Figure 27:
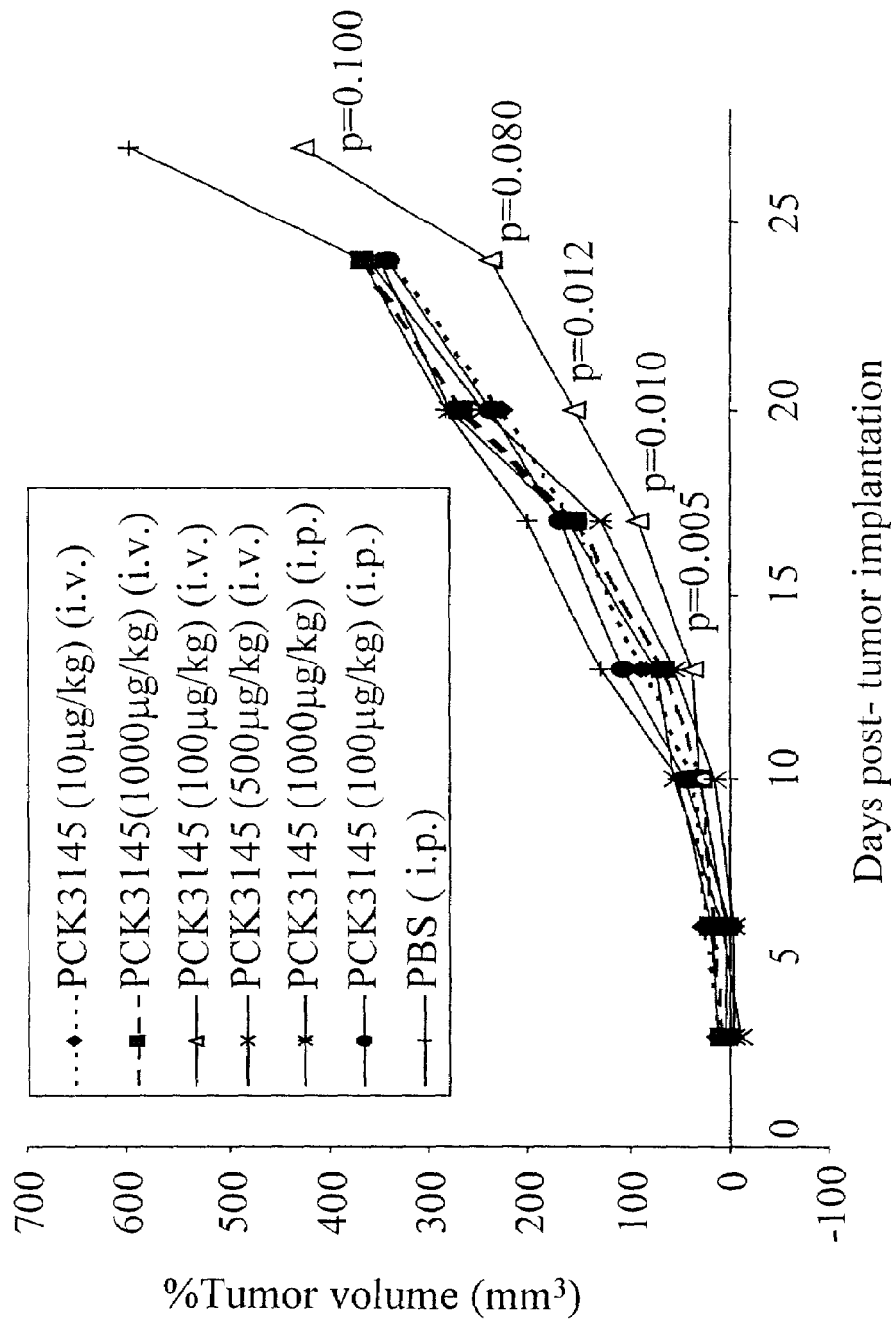

FIG. 27 is a graph depicting the in vivo inhibitory activity of PCK3145 (SEQ ID NO: 5) (10 µg/kg/day to 1000 µg/kg/day, administered either via the intra-venous or intra-peritoneal route) against human PC-3 tumor xenografted in nude mice.

Figure 28:
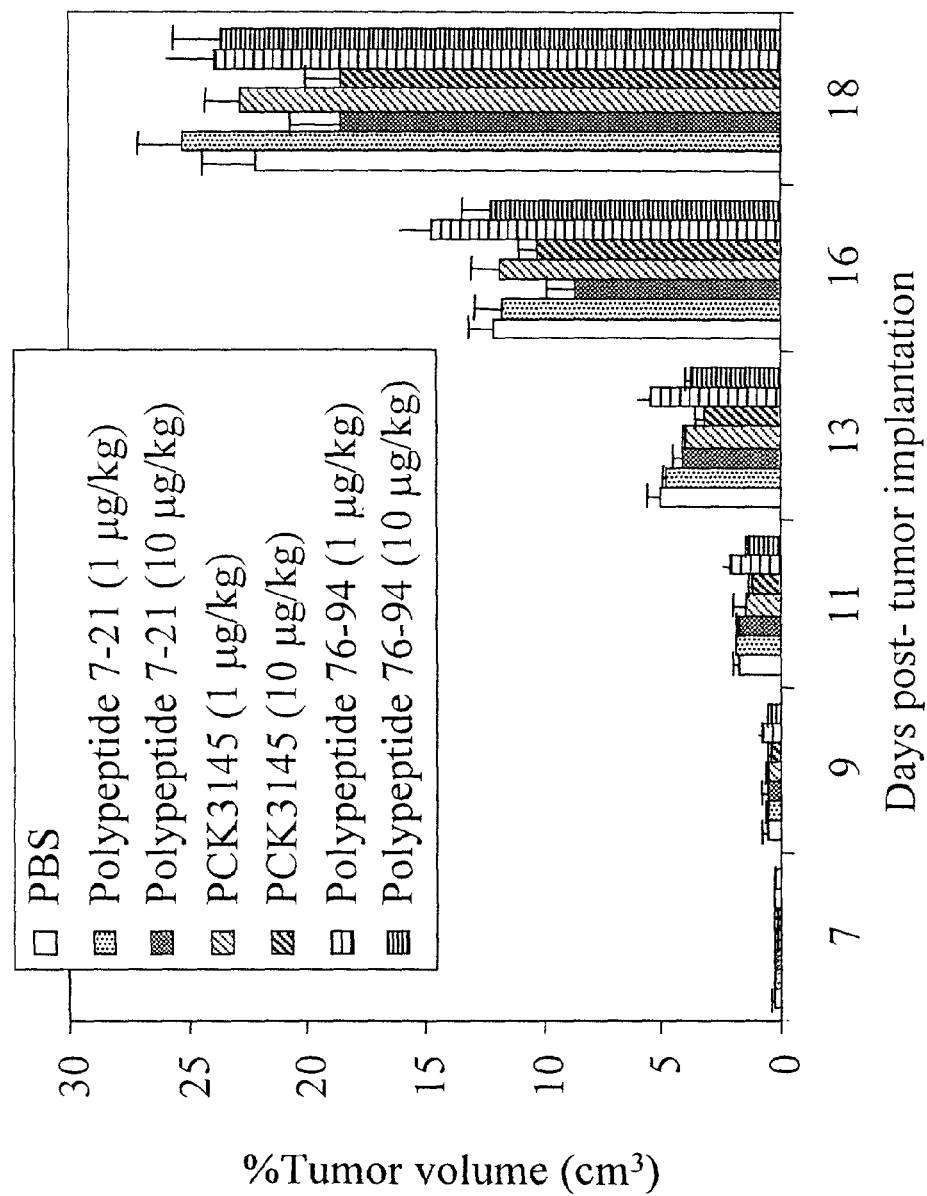

FIG. 28 is a graph depicting the in vivo inhibitory activity of polypeptide 7–21 (SEQ ID NO: 4), PCK3145 (SEQ ID NO: 5) or polypeptide 76–94 (SEQ ID NO: 6), given at doses of 1 µg/kg/day or 10 µg/kg/day, in Copenhagen rats implanted with Dunning Mat Ly Lu tumors.

Figure 29:
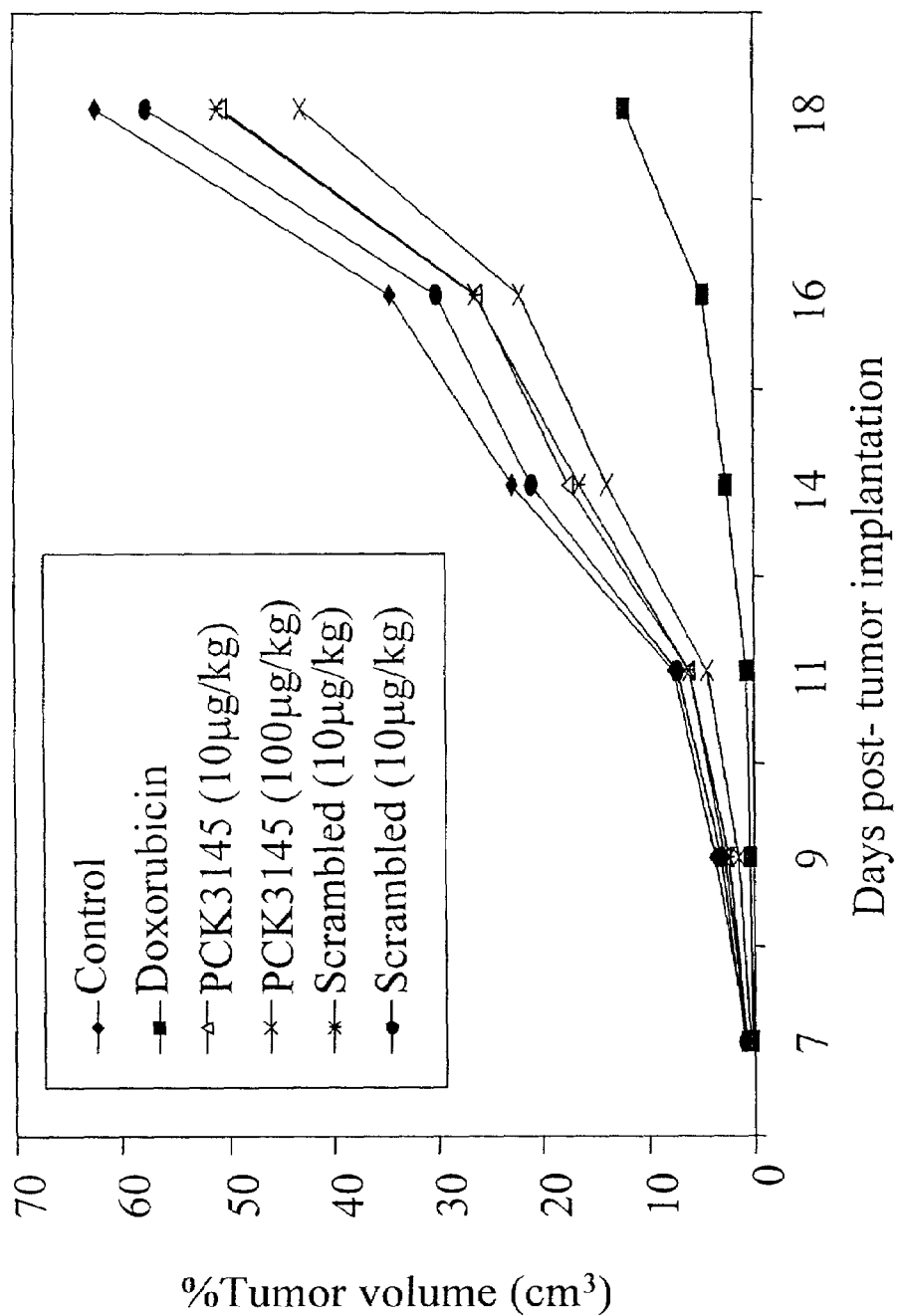

FIG. 29 is a graph depicting the in vivo inhibitory activity of PCK3145 (SEQ ID NO: 5) or the scrambled polypeptide given at doses of 10 µg/kg/day or 100 µg/kg/day, in Copenhagen rats implanted with Dunning Mat Ly Lu tumors.

Figure 30:
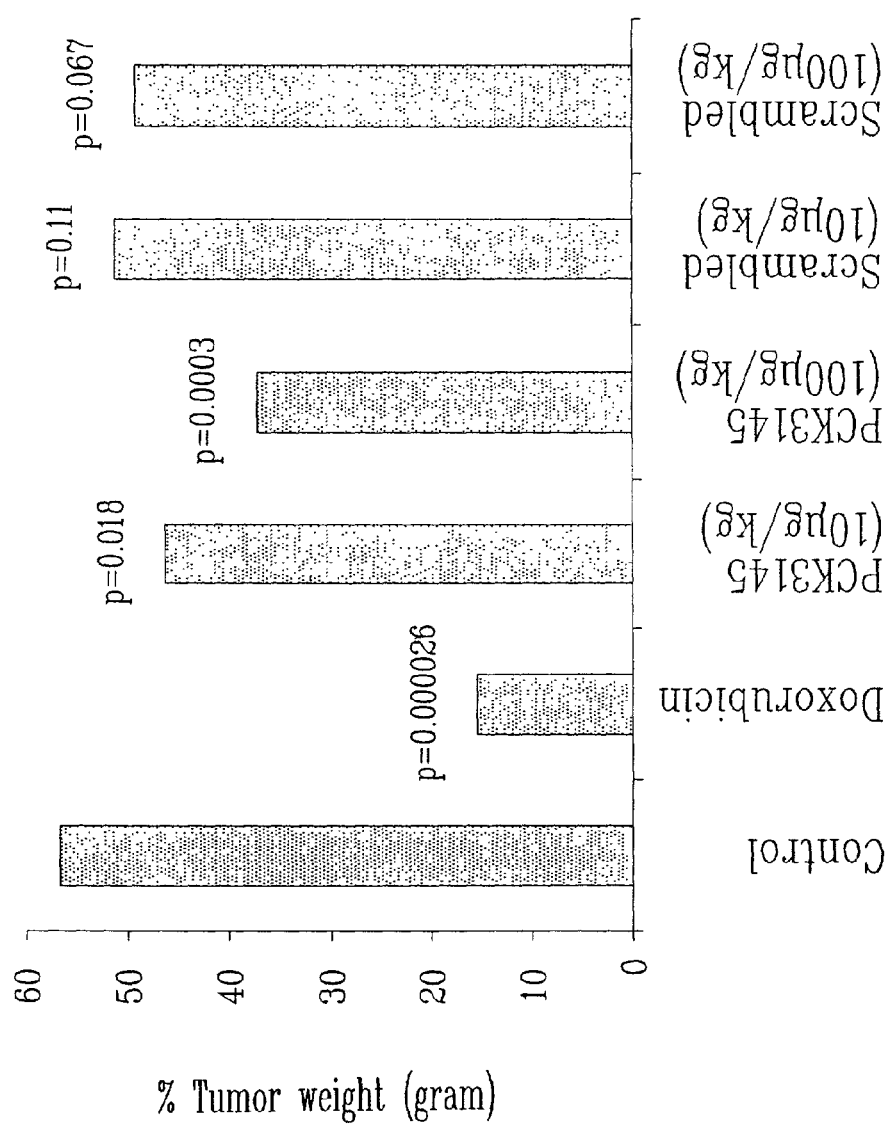

FIG. 30 is a graph depicting tumor weight at day 18 following PCK3145 (SEQ ID NO: 5) or scrambled polypeptide treatment (10 µg/kg/day or 100 µg/kg/day), in Copenhagen rats implanted with Dunning Mat Ly Lu tumors.

Figure 31:
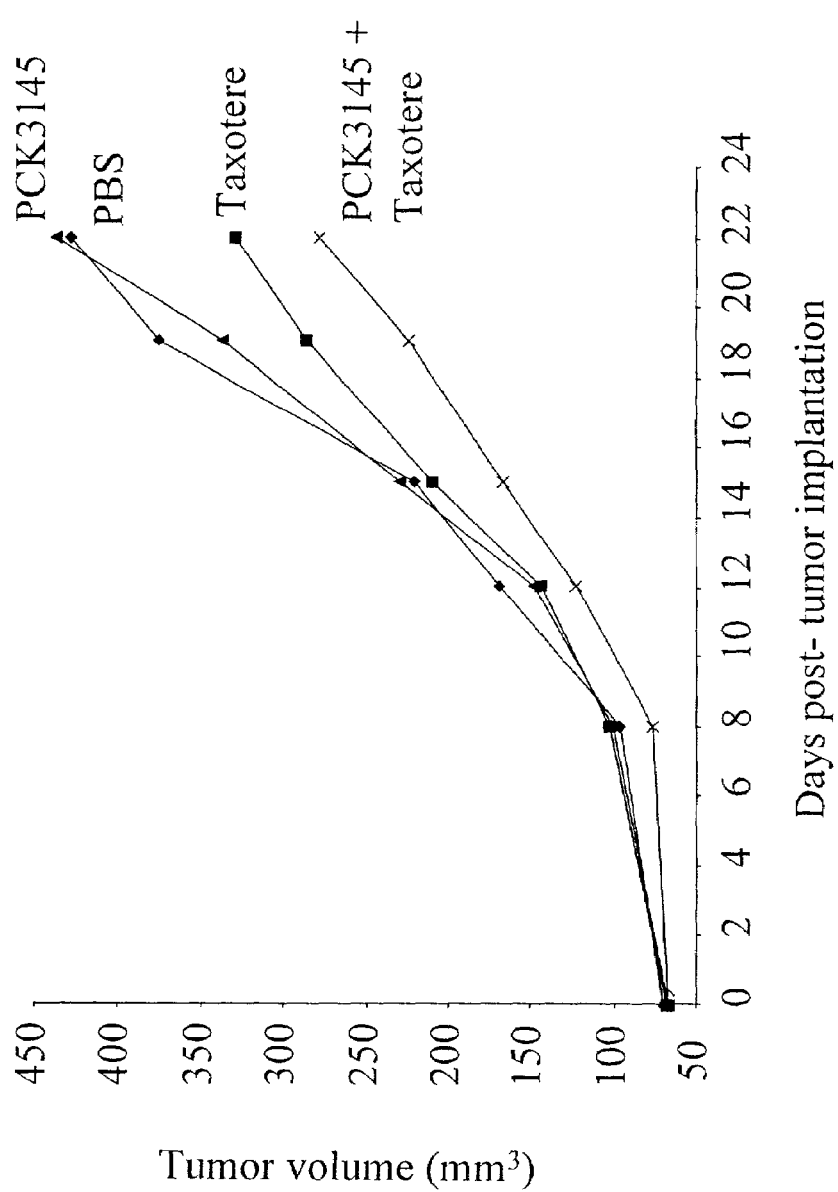

FIG. 31 is a graph depicting the efficacy of PCK3145 and taxotere (i.e. docetaxel) combination treatment in Nude mice implanted with PC-3 tumor cells in tumor growth retardation.

DETAILED DESCRIPTION OF THE INVENTION

The recombinant human rHuPSP94 expressed in yeast is non-glycosylated and has 10 cystein residues. The molecular weight of rHuPSP94 was determined to be 11.5 kDa, compared to 10.7 kDa for its native counterpart.

Various experimental studies have been carried out in order to determine the efficacy of rHuPSP94 (SEQ ID NO: 2) relative to the native PSP94 secreted by the diseased prostate as tumor suppressive agent. Studies have also been carried out to determine the efficacy of the decapeptide as set forth in SEQ ID NO: 3, the polypeptide as set forth in SEQ ID NO: 4 (polypeptide 7–21), the polypeptide as set forth in SEQ ID NO: 5 (PCK3145), and the polypeptide as set forth in SEQ ID NO: 6 (polypeptide 76–94), as tumor suppressive agents. The tumor suppression activity of the polypeptides of the present invention has been monitored by their ability to reduce or inhibit the growth of prostatic adenocarcinoma both in-vivo and in-vitro. Those results are summarized below.

Studies were carried out using PC-3 human prostate adenocarcinoma line, which can be maintained both in vivo as a xenograft in nude mice and in vitro as a cell line. In addition, a rat Dunning Mat LyLu prostate tumor, which is a pre-eminent animal model for the study of CaP, was also used. The Dunning tumor is a fast growing, poorly differentiated, transplantable tumor, which can be maintained both in-vivo in the Copenhagen rat and in-vitro as a cell line.

The following examples are offered by way of illustration and not by way of limitation.

EXAMPLE 1

Preparation of rHuPSP94 (SEQ ID NO: 2) and Polypeptides (SEQ ID NO: 3, SEQ ID NO: 4, SEQ ID NO: 5 and SEQ ID NO: 6)

Recombinant HuPSP94 was cloned and expressed in *Pichia pastoris*, and then purified and characterized as follows.

Materials

DEAE-cellulose (DE52) was purchased from Whatman (Fairfield, N.J.). Dialysis membranes and the electro chemiluminescence (ECL) detection kit were purchased from Biolynx Canada (Pierce Inc.). Broad-range molecular weight markers and Econo-pack columns fitted with flow adapters were purchased from Bio-Rad Labs Ltd (California). Pellicon device was purchased from Millipore (Massachusetts). Tris-HCl was obtained from ICN. MES ((2-[N-Morpholino]ethanesulfonic acid) hydrate)was obtained from Sigma. Swine anti-rabbit IgG alkaline-phosphatase conjugates was purchased from DAKO (Denmark). *Pichia Pastoris* expression Kit version G was from Invitrogen (Carlsbad, Calif.). Non-Radioactive High Prime DIG labeling kit® was purchased from Boehringer Mannheim (Indianapolis, Ind.). The MTS (3-(4,5-dimethylthiazol-2-yl)-5-(3-carboxymethoxyphenyl)-2-(4-sulfophenyl)-2H-tetrazolium, inner salt) assays were performed using Cell Titer Aqueous Non radioactive cell proliferation assay kit from Promega (Madison, Wis.). MRX microtiter plate reader was from Dynex technologies (Chantillly, Va.). Rabbit polyclonal antiserum against PSP94 was a gift from the late Dr. A. Sheth. All primers were synthesized by Procyon Biopharma Inc. London, Ontario, Canada.

Cell Line and Cell Culture

*P. pastoris* host strain GS115 (his4) and all *Pichia* related products were obtained from Invitrogen. PC-3 (ATCC-# CRL 1435) cell line was obtained from the American Type Cell Culture (ATCC) and maintained in OPTI MEM (minimum essential media) with 10% fetal bovine serum (FBS). All cell culture products were obtained from GIBCO BRL.

Cloning

TA cloning vector (pCR TM 2.1) containing human PSP94 cDNA including a 20 amino acid leader sequence described previously (Baijal-Gupta, M., et. al., J. Endocrinol., 165:425–433, 2000) was used to amplify human PSP94 without its leader sequence using appropriate primers. The primers for the polymerase chain reaction (PCR) were designed to contain an EcoRI restriction sites at either end. The 5' primer used was 5'-GGG AAG AAT TC<u>T</u>CAT GCT ATT TCA TA-3' (SEQ ID NO: 7) and the 3' primer, 5'-TGG ATA TCT GCA GAA TTC GGC-3' (SEQ ID NO: 8). The +1 start site for PSP94 (at a Serine residue) has been underlined in the 5' primer described above.

The PCR included 1 cycle of 12 minutes at 94° C., followed by 25 cycles of 1 minute at 94° C., 1 minute at 55° C., 1 minute at 72° C. and a final step of 1 cycle of 10 minutes at 72° C. PCR amplification of the product was performed using BM Expand™ High Fidelity PCR System. The product was run on a 1.5% agarose gel and the appropriate PCR product was isolated using Pharmacia Sehphaglass Kit (Bandprep). Subcloning of the PSP94 insert was performed in pPIC9 vector (Invitrogen). The EcoRI enzyme was used for the restriction digestion of both the plasmid and the PCR products (thus removing PSP94 signal sequence) followed by ligation and transformation, using DH5α cells. The isolated clones were selected for by ampicillin resistance and inserts were identified by restriction mappings. The constructs were sequenced (Robart's sequencing service, London, Ontario) to identify PSP94 insert with a correct sequence as well as proper orientation and reading frame.

Screening for Clones Expressing rHuPSP94

For *Pichia pastoris* transformation, the spheroplast method was used according to manufacturer's instructions (Invitrogen) using GS115 and KM71 yeast strains. Plasmid pPIC9 with or without the PSP94 insert were linearized using SalI restriction enzyme. Transformed colonies were screened and selected for their ability to produce their own histidine, hence survived on media without histidine. All GS115 transformants scored as $Mut^+$, whereas all KM71 colonies, which did not grow well in the liquid culture, scored as $Mut^s$. Hence a number of GS115 clones were screened for production of the highest levels of rHuPSP94 expression.

About a hundred clones were selected and grown into 2 ml of culture media until an optical density at 600 nm (OD600) of approximately 6 was reached. Total DNA was isolated for rapid dot blot analysis in order to detect multiple integrations by Southern blot that would possibly correspond to high rHuPSP94 expressing clones. Two hundred microliters of each culture specimens were denatured and blotted (in duplicate) to a positively charged nylon membrane, placed in a dot blot apparatus. The membrane was subsequently air-dried. The membrane was soaked between two sheets of Whatman 3MM paper for 15 minutes in a solution containing 50 mM ethylenediaminetetraacetic acid (EDTA), 2.5% beta-mercaptoethanol (BME), pH 9, followed by an incubation of 24 hours at 37° C. with 1 mg/ml Zymolyase 100T, 5 minutes in 0.1 N NaOH, 1.5 M NaCl, 0.015 M sodium citrate pH 7 and two 5 minutes incubation in 2× saline-sodium citrate (SSC). Finally the membrane was baked at 80° C. for 45 minutes and exposed to ultraviolet light (UV) for 15 minutes. Human PSP94 cDNA probe was labeled with the non-radioactive High Prime DIG labeling kit® (Boehringer Mannheim) and was used for hybridization. Hybridization with digoxigenin labeled cDNA probe (25 ng/μl) was done for 2 days at 42° C. in Sodium dodecyl sulfate(SDS) buffer (SDS 7% (w/v); formamide 50% (v/v); 5×SSC; 50 mM sodium phosphate, pH 7.0; N-lauroyl-sarcosine 0.1% (w/v)) and blocking reagent, CSPD® 2% (w/v) (Boehringer Mannheim) was used as the chemiluminescence substrate. All digoxigenin (DIG) labeling procedures were performed according to the manufacturer's instruction. Detection was performed using the Hyper film-ECL product (Amersham Life Science Inc. Arlington Hts, Ill.).

The clone with the highest signal intensity was used for all flasks shaken cultures.

Optimization of the Expression of the Protein in Flask Shaken Cultures

A clone containing the PSP94 construct was selected for high expression of the protein. Colony was grown in 25 ml of basal minimum growth media (BMG) until an OD600 between 2 and 6 was obtained. This clone was further amplified in Baffled Erlenmeyer flasks in a volume of 1 liter of BMG media until the OD600 reached approximately between 2.0 to 6.0. The culture was centrifuged for 15 minutes at 2500×g and the pellet was collected. The induction phase (i.e., induction of expression of rHuPSP94) was carried out by inoculating the cell pellet in basal minimum media (BMM). Growth was performed in Baffled flasks for 6 days, as recommended by Invitrogen. The volume of BMM added varied according to the size of the pellet collected. Five milliliters of 100% methanol were added for each liter of culture. This was performed each day, around the same time, to a final concentration of 0.1% of methanol. A plasmid without the PSP94 insert served as a negative control.

To determine the optimum time for harvesting rHuPSP94 secreted in the cell culture media, aliquots were taken every 24 hours for 6 days, starting from the first day of induction. Levels of rHuPSP94 protein expression were determined by measuring OD600 and by performing a 15% SDS-PAGE (sodium dodecyl sulfate polyacrylamide gel electrophoresis) stained with Coomassie Brilliant blue or by Western blot analysis using polyclonal antibody against PSP94.

Sample Preparation

Culture supernatant of clone showing the highest rHuPSP94 expression, post-induction (e.g., after 96 hours), was centrifuged at 2500×g for 20 minutes. The supernatant was filtered through a 0.8 μm filter and concentrated approximately 10-fold using a Pellicon unit (Millipore). The filtered supernatant was dialyzed against 0.05 mM Tris-HCl buffer, pH 8.0, using a 3500 molecular weight cut-off membrane. An aliquot of the dialyzed supernatant was analyzed by SDS-PAGE and Western blot analysis and the rest was submitted to further purification.

Culture Conditions for Fermentation

Fermentation was carried out at the Institute for Biological Sciences, National Research Council (NRC) (Ottawa, Ontario Canada), following manufacturer's instruction (Invitrogen). For example, a fermentation procedure was initiated by inoculating 7.5 liter of media with 625 ml of a starting culture. The growth phase was carried out for approximately 2 days in BMG media until the OD600 reached approximately 0.5. The induction phase was initiated by the addition of methanol (100%), according to the manufacturer's instructions (Invitrogen). The culture was harvested after 95 hours (i.e., after induction with methanol for 67 hours). The final volume of the culture was approximately 13.5 liters.

Sample Preparation from Fermentation Culture

The large cell mass was removed by centrifugation. The cell free media collected (9 liters) was further clarified using a 0.2 μm filtration unit (Pellicon). The remaining 8.5 liters containing secreted rHuPSP94 was tested for protein expression and stored at −20° C. for further isolation and purification of the protein.

Protein Estimation

The amount of rHuPSP94 protein secreted in the culture supernatant from the flask shaken and the fermentation process was obtained based on estimates of band intensities of samples compared to band intensities of a standard curve obtained by loading known quantities of pure lyophilized PSP94 on a SDS-PAGE. The initial estimate for rHuPSP94 at each step of purification was determined by OD at 280 nm. Quantification of total protein content at the final steps of purification was done by the BCA (bicinchoninic acid) method, using bovine serum albumin (BSA) as standard.

Lyophilization

Samples of purified rHuPSP94 were dialyzed against deionized water using a 3000 molecular weight cut-off membrane and were lyophilized.

SDS-PAGE

SDS-PAGE was performed using acrylamide at a final concentration of 15% for the separating portion of the gel and acrylamide at a final concentration of 5% for the stacking portion of the gel. The gel contained 0.1% SDS and was performed under reducing conditions. Broad-range molecular weight markers were used for the estimation of molecular weight of the protein. Proteins were stained with Coomassie Brilliant Blue R-250.

Western Blotting

For immunoblotting, Mini Trans-Blot Electrophoretic Transfer Cell (Bio Rad) was used with Hi bond-C super membrane (Amersham) and 85 mm blotting papers. Protein samples (0.4 µg) were loaded and separated on SDS-PAGE, as described earlier. Proteins were transferred to the membrane for 2 hours at 4° C., using transfer buffer (25 mM Tris, 192 mM Glycine, pH 8.3 and 20% methanol) and a transfer unit set at 200 milliamperes (mAmp). Membranes were blocked overnight by incubation in 2% (w/v) non-fat dry milk (skim milk) disolved in tris buffer saline (TBS: 500 mM NaCl, 20 mM Tris-HCl, pH 7.5) at room temp (RT). Membranes were washed three times with TBS containing 0.02% (v/v) Tween-20 (this buffer is named TTBS). Membranes were subsequently incubated for 2 hours at RT with anti-PSP94 antibody (1:2000 dilution) diluted in TTBS containing 2% skim milk. Membranes were washed twice with TTBS (5 minutes each washing), and incubated at RT with a secondary antibody (i.e., swine anti-rabbit antibody HRP conjugated) (1:5000 dilution) diluted in TTBS. Membranes were washed twice with 0.02% TTBS (5 minutes each washing). Blots were developed using the ECL detection system, according to manufacturer's instructions, using the Super Signal Substrate, and exposed to a Hyperfilm ECL from Amersham LS for 5 to 20 seconds. Pre-stained molecular weight markers were used for molecular weight estimation.

Purification of rHuPSP94 using DE52 Column Chromatography

Following removal of *P. pastoris* cells from the fermentation culture, supernatant was concentrated approximately ten fold, dialyzed and subjected to anion exchange chromatography. A DE52 column having a bed volume of approximately 40 ml (2.5 cm internal diameter (id)×8 cm height(h)) was equilibrated with 0.05 M Tris-HCl, pH 8.0 (equilibrating buffer). The sample (25 ml) containing 15 to 20 mg of rHuPSP94 protein was applied to the DE52 column at a flow rate of 1 ml/minute.

Impurities were removed from the column by washing it with 40 to 50 ml of the equilibrating buffer, and monitoring the absorbance at 280 nm. This step was followed by the addition of 100 to 150 ml of 0.05 M Tris-HCl, pH 6.5 to the column until the pH of the wash reached approximately 6.5. The column was further washed with 100 to 150 ml of 0.05 M MES-acetate buffer, pH 6.5, until the absorbance at 280 nm approached zero. Finally rHuPSP94 was eluted from the column with 0.05 M MES-acetate buffer, pH 5.0. Peak fractions were characterized by absorbance at 280 nm, followed by SDS-PAGE and Western blot analysis as described above. Fractions with high absorbance at 280 nm values (0.5 to 1.8) were pooled and dialyzed against water or PBS for storage at −20° C. and/or lyophilization.

Amino acid Composition

Amino acid analysis of the DE52 purified flask shaken culture and fermentation cultures was carried out. The Perkin Elmer Biosystems Derivatizer-Analysis system was used with Spheri-5 PTC C-18 5µ column and UV detection at OD254.

Mass Spectral Analysis

Figure 1:
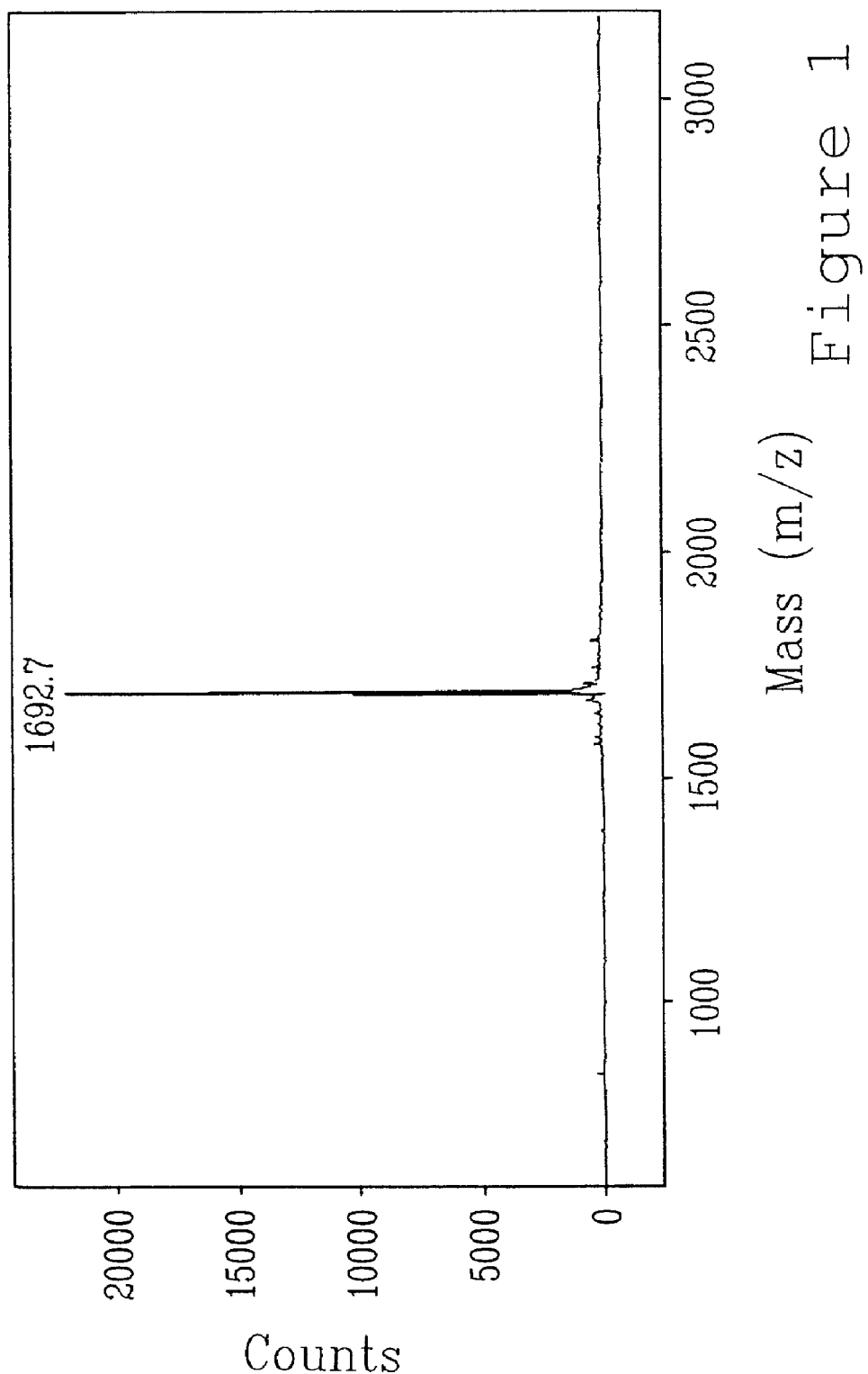
FIG. 1 depicts mass spectrometry analysis of polypeptide 7–21 (SEQ ID NO: 4).
Figure 2:
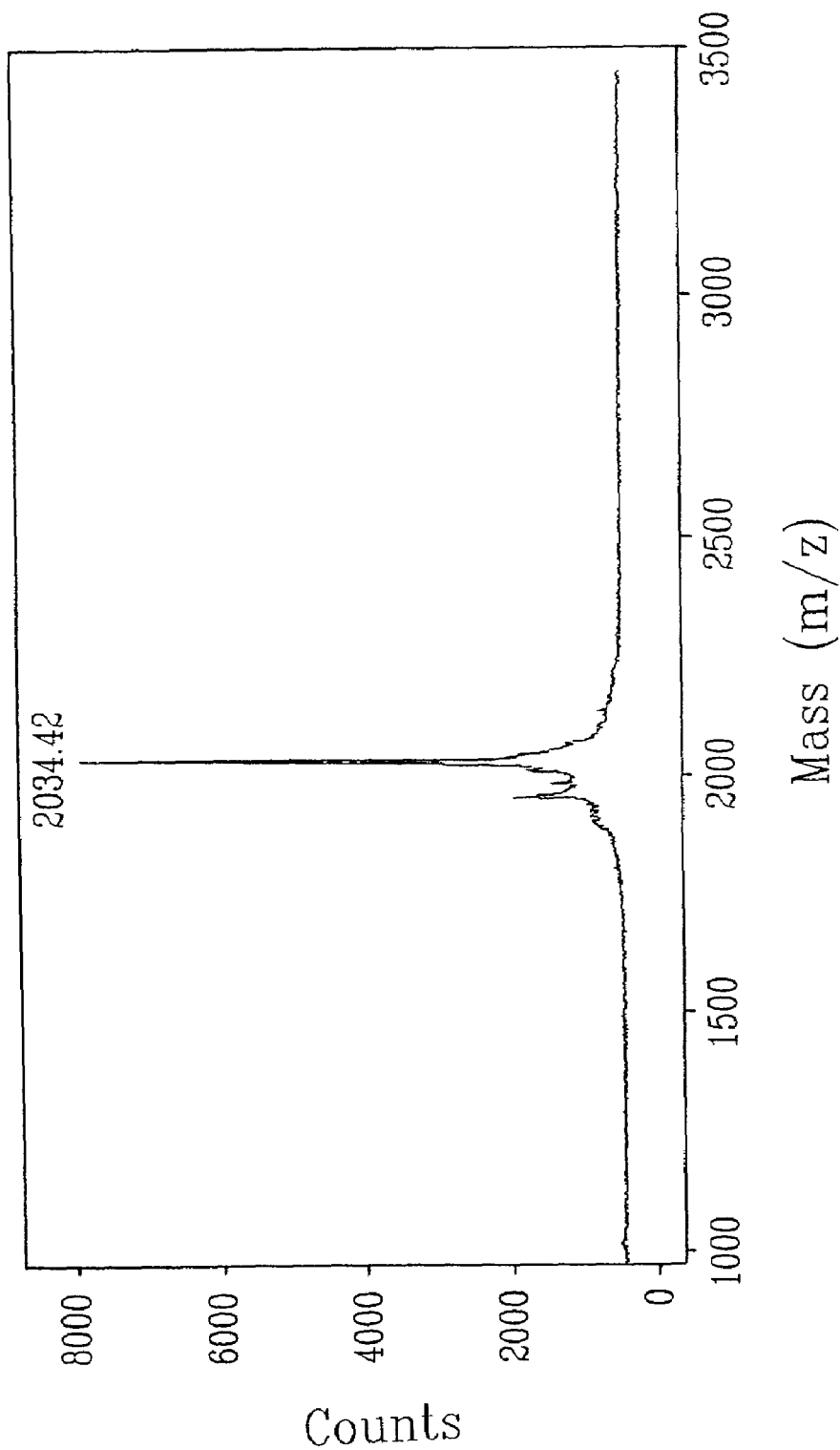
FIG. 2 depicts mass spectrometry analysis of polypeptide PCK3145 (SEQ ID NO: 5).

PSP94 derived polypeptides were synthesized, were found to be in accordance with the required specifications and were analyzed by Mass Spectral Analysis. Mass spectrometry analysis of polypeptide 7–21 (SEQ ID NO: 4), PCK3145 (SEQ ID NO: 5) and polypeptide 76–94 (SEQ ID NO: 6) are represented in FIGS. 1, 2 and 3 respectively.

Polypeptide samples were analyzed using the PerSeptive Biosystems (Framingham, Mass.), with Voyager-DE MALDI-TOF mass spectrometer using 337 nm light from a nitrogen laser. About 12 to 50 scans were averaged for each analysis.

Purified samples from the flask shaken culture and fermentation culture were analyzed using the PerSeptive Biosystems (Framingham, Mass.), with Voyager-DE MALDI-TOF mass spectrometer using 337 nm light from a nitrogen laser. About 50 scans were averaged for each analysis. A sample from the native PSP94 was also analyzed under similar conditions for comparison.

EXAMPLE 2

In-vitro Effect of rHuPSP94 on PC-3 Cells (MTS Assay)

The biological activity of the rHuPSP94 was determined by its growth inhibitory effect on human prostate cancer cells PC-3. Cell proliferation was monitored on PC-3 cells using the MTS/PMS (phenazine methosulfate) kit (Promega), which primarily measures mitochondrial activity of live cells. The basic principle of this method involves the fact that the mitochondrial enzymes of the live cells metabolize the MTS/PMS dyes forming a brown colored precipitate which can be measured as optical density (OD) by absorption at 490 nm in a spectrophotometer. Therefore, the OD values are proportional to the number of living cells. In addition, monitoring of cell morphology was also performed. Cell morphology would be indicative of their health status. For example, viable cells would appear adherent and spread out whereas dead cells would be in suspension in the media and would appear granular and round.

Results of in vitro effect of rHuPSP94 on PC-3 cells measured by MTS assay are summarized in table 2, below. PC-3 cells (ATCC, Lot AT06) used in these experiments were at a passage number lower or equal to 70 (n≧70). Cells were seeded in Costar 96 well cell culture flat bottom plates in RPMI supplemented media containing 50 µg/ml of bovine serum albumin (BSA) and 0.1 µM $FeSO_4$. Peptide was diluted in the same media. Cells were continuously exposed to the polypeptides of the present invention for 72 hours without changing media. Native PSP94 or rHuPSP94 concentrated two fold were directly added to wells and diluted to 1× in order to minimize cell manipulation and avoid detachment.

The evaluation of growth inhibitory effect of rHuPSP94 on PC-3 cells indicated a substantial reduction in cell numbers (i.e., viability) ranging from 37% to 57% reduction at concentrations of 80 and 120 µg/ml of rHuPSP94 respectively. This effect was observed in 3 out of 4 experiments (Table 2). Results of trypan blue exclusion test demonstrated a cell viability of 62% at 80 µg/ml.

TABLE 2

| Experiment no. | Sample | % Viability (control = 100%) (µg/ml) | | | |
|---|---|---|---|---|---|
| | | 40 | 60 | 80 | 120 |
| 1 | rHuPSP94 | 72 | 78 | 58 | 43 |
| 2 | rHuPSP94 | 63 | 63 | 63 | 68 |
| 3 | rHuPSP94 | 95 | 85 | 78 | ND |
| 4 | rHuPSP94 | 100 | 52 | 62 | 60 |
| 5 | rHuPSP94 | 100 | 98 | 90 | 52 |

| Sample | % Viability (control = 100%) (µg/ml) | | | | |
|---|---|---|---|---|---|
| | 5 | 10 | 20 | 40 | 80 |
| rHuPSP94 | 98 | 84 | 78 | 70 | 55 |
| rHuPSP94 | 92 | 95 | 80 | 71 | 59 |
| rHuPSP94 | 89 | 69 | 79 | 68 | 65 |

EXAMPLE 3

In-vitro Effect of rHuPSP94 on PC-3 Cells ([$^3$H]-Thymidine Uptake Assay)

The in vitro growth inhibition effect of rHuPSP94 was assessed using [$^3$H]-Thymidine uptake assay. [$^3$H]-Thymidine uptake assay involves [$^3$H]-Thymidine incorporation into cellular DNA of actively proliferating cells. It measures the proliferative index of the cells versus the MTS assay, which quantifies the number of lived cells following treatment. Cells were seeded in Costar 96 well cell culture flat bottom plates in RPMI supplemented media containing 50 µg/ml of bovine serum albumin (BSA) and 0.1 µM FeSO$_4$. PC-3 cells were exposed to various concentrations of rHuPSP94 for 72 hours and during the final 16 hours of incubation cells were pulsed with 1 µCi of [$^3$H]-Thymidine. The radioactivity in each well of the plate is counted by a beta-counter and is expressed as total counts per minutes (cpm). Results of in vitro effect of rHuPSP94 on PC-3 cells using the $^3$[H]-Thymidine uptake assay are summarized in Table 3 and are expressed as percentage of radioactivity measured for treated-cells relative to the radioactivity measured for non-treated cells (for which [$^3$H]-thymidine uptake value was set at 100%).

Results indicated a 65% reduction in the percentage of cells incorporating [$^3$H]-thymidine following treatment with rHuPSP94 at a concentration of 80 µg/ml for 72 hrs, compared to the non-treated control. Results of a 65% reduction in [$^3$H]-thymidine uptake may also be an indication of a 65% reduction in cell proliferation.

Comparison was performed between [$^3$H]-Thymidine uptake assay and the MTS assay, in order to evaluate their relative sensitivity. An additional plate was set aside for MTS assay and treated in parallel with the same lot (i.e., batch) of rHuPSP94 as the one used for the [$^3$H]-thymidine uptake assay. Result obtained for the MTS assay demonstrated a 35% reduction in cell viability (65% cells remaining viable) following treatment with rHuPSP94 at a concentration of 80 µg/ml, indicating that the [$^3$H]-Thymidine uptake assay, which was able to measure a 65% reduction in cell proliferation, may be more sensitive than the MTS assay.

TABLE 3

| Experiment no. | Sample | $^3$[H]-Thymidine Uptake (% of control) (µg/ml) | | | | |
|---|---|---|---|---|---|---|
| | | 5 | 10 | 20 | 40 | 80 |
| 1 | rHuPSP94 | 94 | 101 | 98 | 79 | 35 |
| 1 | native PSP94 | 97 | 98 | 100 | 98 | 77 |

EXAMPLE 4

In-vitro Effect of Decapeptide and other Polypeptide on PC-3 Cells

Figure 4A:
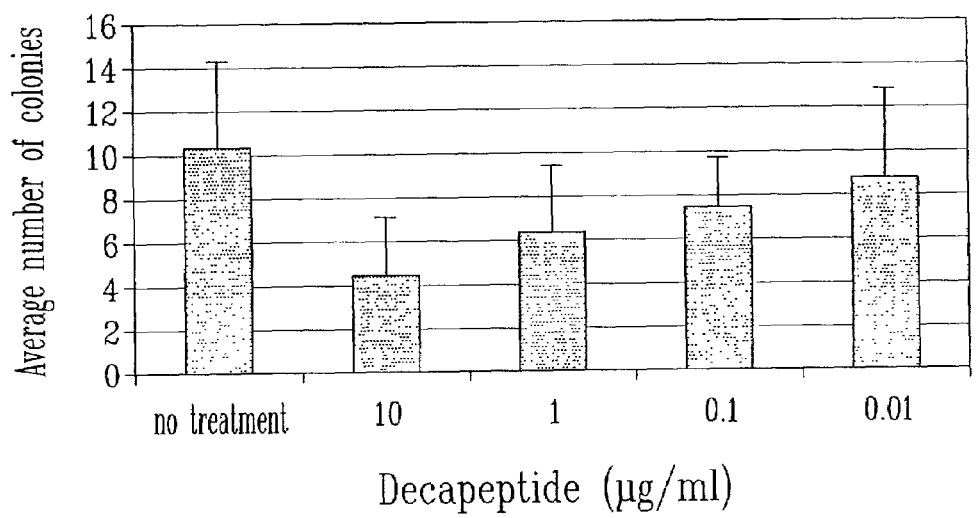
FIG. 4*a* is a graph depicting the in-vitro inhibitory activity of the decapeptide of SEQ ID NO: 3 on PC-3 cells after 9 days of culture.
Figure 4B:
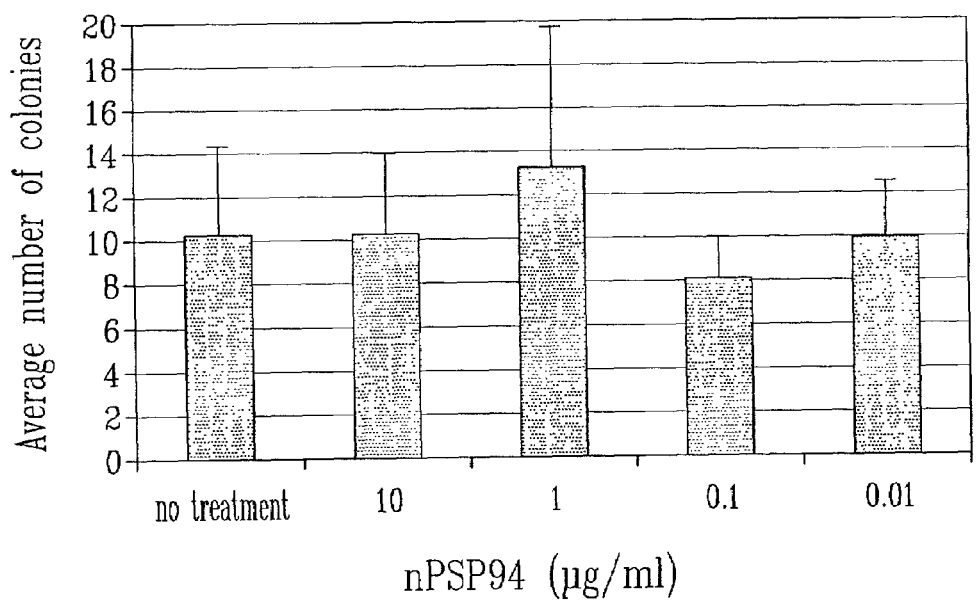
FIG. 4*b* is a graph depicting the in-vitro inhibitory activity of the native PSP94 (nPSP94) on PC-3 cells after 9 days of culture.
Figure 5A:
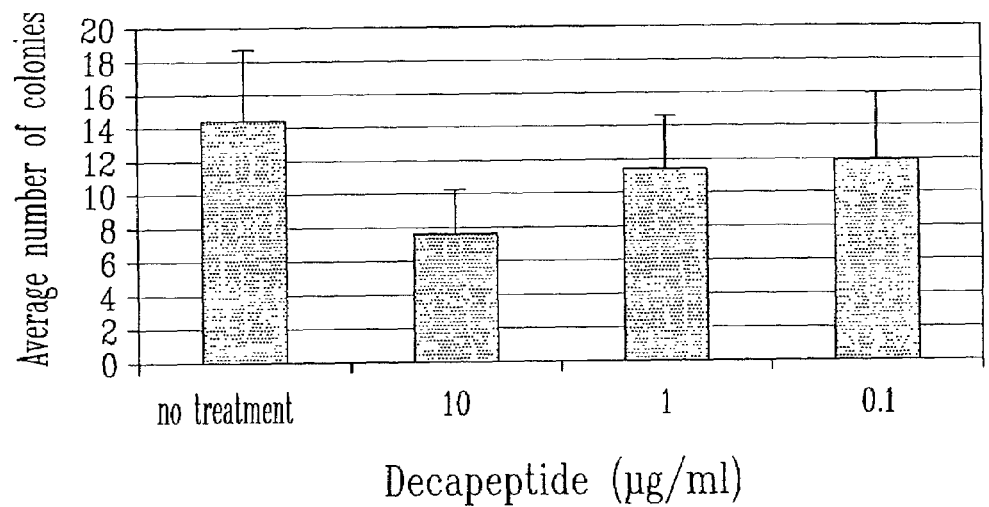
FIG. 5*a* is a graph depicting the in-vitro inhibitory activity of the decapeptide of SEQ ID NO: 3 on PC-3 cells after 21 days of culture.
Figure 5B:
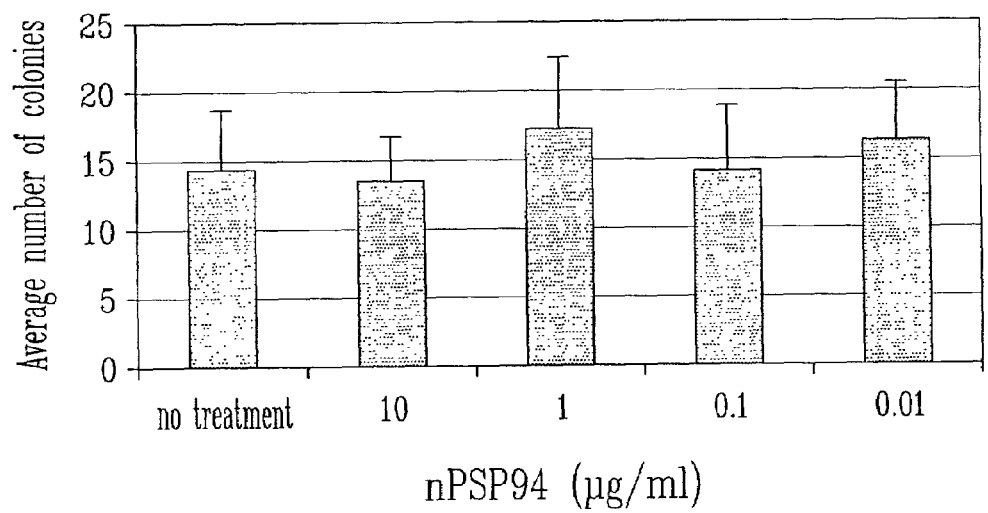
FIG. 5*b* is a graph depicting the in-vitro inhibitory activity of the native PSP94 (nPSP94) on PC-3 cells after 21 days of culture.
Figure 6A:
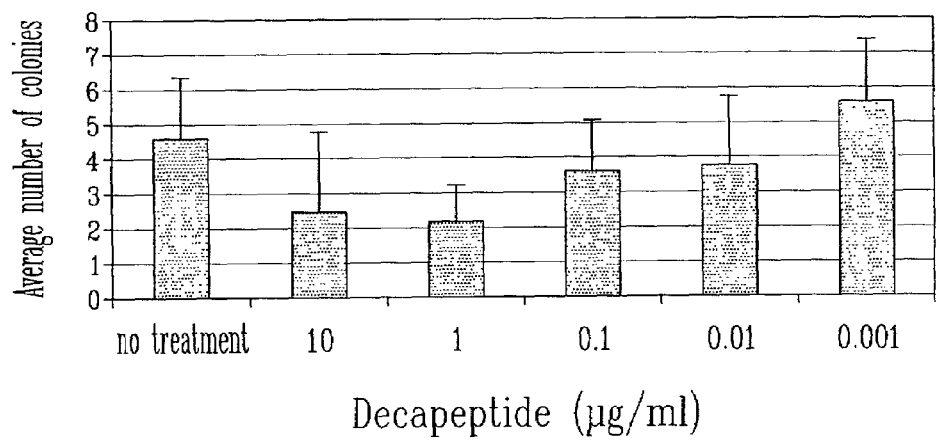
FIG. 6*a* is a graph depicting the in-vitro inhibitory activity of the decapeptide of SEQ ID NO: 3 on PC-3 cells after 10 days of culture.
Figure 6B:
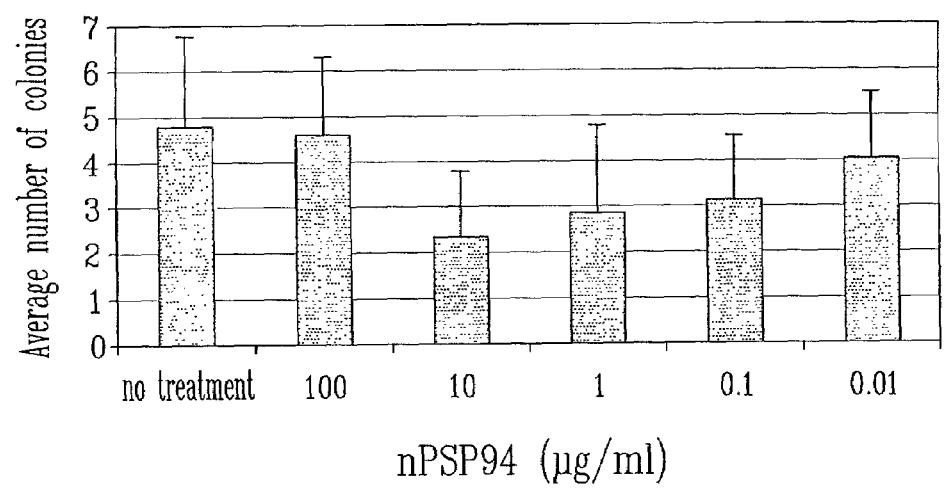
FIG. 6*b* is a graph depicting the in-vitro inhibitory activity of the native PSP94 (nPSP94) on PC-3 cells after 10 days of culture.

The synthetic decapeptide (SEQ ID NO: 3) has been shown herein to mimic the biological activity of native PSP94 (nPSP94)(SEQ ID NO: 1) and therefore its effect on the PC-3 cells was studied in clonogenicity assay (colony formation). Cells were seeded in Costar 96 well cell culture flat bottom plates in RPMI supplemented media containing 50 µg/ml of bovine serum albumin (BSA) and 0.1 µM FeSO$_4$. Clonogenicity was evaluated for PC-3 cells grown in the presence of various concentration of the decapeptide after 9 days of culture (FIG. 4a). A parallel experiment was performed with various concentration of nPSP94 using the same experimental conditions (FIG. 4b). Other experiments evaluating clonogenicity was performed with the decapeptide (FIG. 5a) or nPSP94 (FIG. 5b) after 21 days of culture as well as after 10 days of culture (FIG. 6a: Decapeptide and FIG. 6b: nPSP94).

Referring to FIGS. 4 to 6, the decapeptide (SEQ ID NO: 3) had a similar inhibitory action as nPSP94 (SEQ ID NO: 1) on in-vitro PC-3 cells studied. Results indicated a 40% decrease in colony number for cells incubated with the decapeptide (SEQ ID NO: 3) at a concentration of 1 µg/ml. A decrease in colony number of up to 60% was observed for the decapeptide (SEQ ID NO: 3) at a concentration of 10 µg/ml.

EXAMPLE 5

DNA Fragmentation Assay

Figure 7:
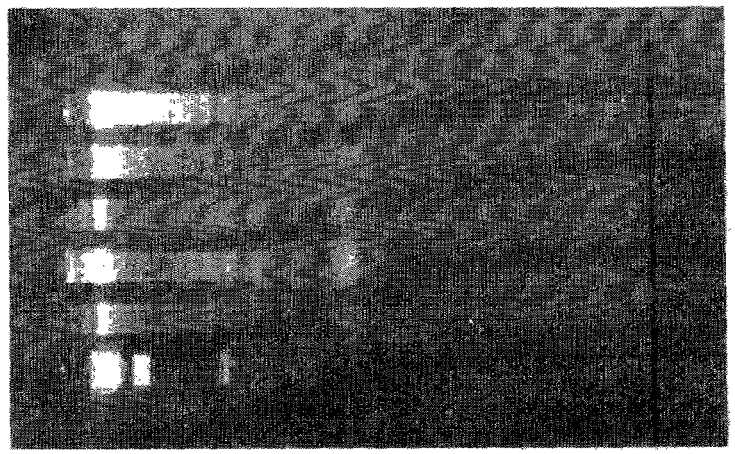
FIG. 7 depicts a gel showing DNA fragmentation following treatment of PC-3 cells with polypeptide PCK3145 as set forth in SEQ ID NO: 5.

Cell apoptosis result in DNA fragmentation can be evaluated by the presence of a DNA ladder visualized when DNA is run on a 1.2% agarose gel. DNA ladder assay (apoptosis assay) was performed following exposure of PC-3 to various concentrations of the polypeptides for 72 hours. The polypeptides that were used in this particular experiment are polypeptide 7–21 (SEQ ID NO: 4), polypeptide PCK3145 (SEQ ID NO: 5) and polypeptide 76–94 (SEQ ID NO: 6). Visualization of DNA isolated and run on 1.2% agarose gel, demonstrated that every polypeptides tested induced a DNA laddering effect characteristic of apoptosis. This effect was especially evident following treatment with PCK3145 (SEQ ID NO: 5), which is illustrated by FIG. 7. Lane 1 of the gel illustrated in FIG. 7 represents a lambda HindIII digest standard. Lane 2 of the gel illustrated in FIG. 7 represents DNA laddering effect obtained for doxorubicin-treated cells. Lane 3 of the gel illustrated in FIG. 7 represents DNA laddering effect obtained for cells incubated with 40 µg of nPSP94. Lane 4 of the gel illustrated in FIG. 7 represents DNA laddering effect obtained for cells incubated with 20 µg of nPSP94. Lane 5 of the gel illustrated in FIG. 7 represents DNA laddering effect obtained for cells incubated with 22.5

μM of PCK3145 (SEQ ID NO: 5). Lane 6 of the gel illustrated in FIG. 7 represents DNA laddering effect obtained for cells incubated with 45 μM of PCK3145 (SEQ ID NO: 5).

EXAMPLE 6

Apoptosis Assay by Elisa Plus

The three polypeptides (SEQ ID NO: 4, SEQ ID NO: 5 and SEQ ID NO 6) and native PSP94 used here as a positive control were tested in ELISA plus assay to measure cell death through apoptosis. Briefly, the ELISA plus assay is a sandwich enzyme immunoassay able to measure mono- and oligonucleosomes present in the cytoplasmic fraction of cell lysate using two antibodies, one directed against DNA and the other directed against histones. The apoptotic cell death is characterized by activation of endogenous endonucleases (e.g., calcium- and magnesium-dependant), which cleave double-stranded DNA at the most accessible internucleosomal linker region, generating mono- and oligonucleosomes. The enrichment of mono- and oligonucleosomes in the cytoplasm of the apoptotic cells is due to the fact that DNA degradation occurs several hours before plasma membrane breakdown.

Four thousand cells were seeded in Costar 96 well cell culture flat bottom plates in RPMI supplemented media containing 50 μg/ml of bovine serum albumin (BSA) and 0.1 μM $FeSO_4$. The PC-3 cells were treated with various concentrations (22.5 μM to 90 μM) of polypeptides for 72 hours. Apoptosis assay was done as per manufacturer's instructions using the ApopTag kit (Boeringher Mannheim).

Figure 8:
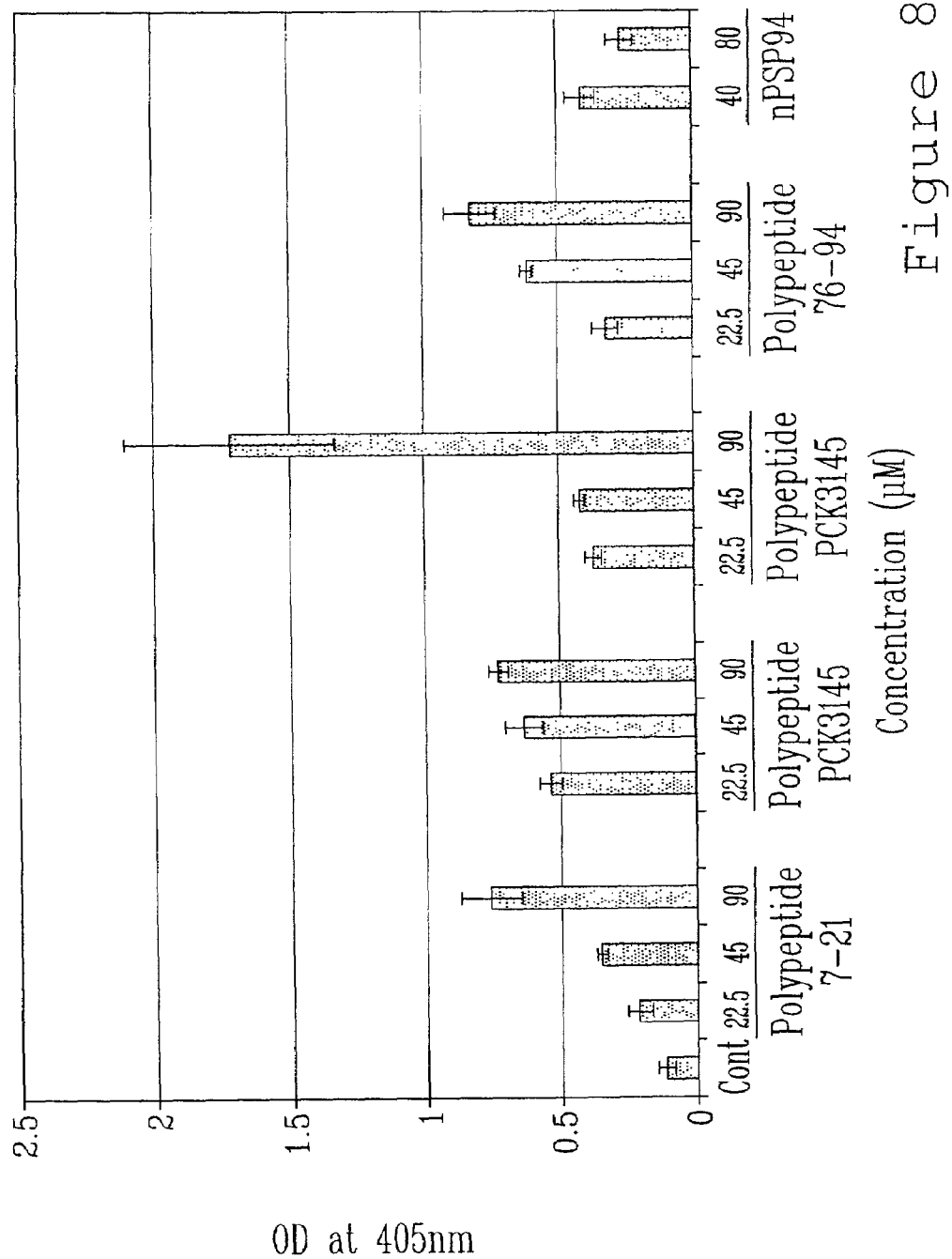
FIG. 8 is a graph depicting the results of an apoptosis assay with an ELISA plus kit following polypeptide treatment of PC-3 cells for 72 hours with various concentration of polypeptide 7–21 (SEQ ID NO: 4), polypeptide PCK3145 (SEQ ID NO: 5), polypeptide 76–94 (SEQ ID NO: 6) or native PSP94 (SEQ ID NO: 1).

Results presented in FIG. 8, indicate a dose dependent increase in the apoptotic cell death effect was observed for every polypeptides used (SEQ ID NO: 4, SEQ ID NO: 5 and SEQ ID NO 6). Polypeptide PCK3145 (SEQ ID NO: 5) was more potent than the other polypeptides at 90 μM concentration (FIG. 8).

EXAMPLE 7

Figure 9:
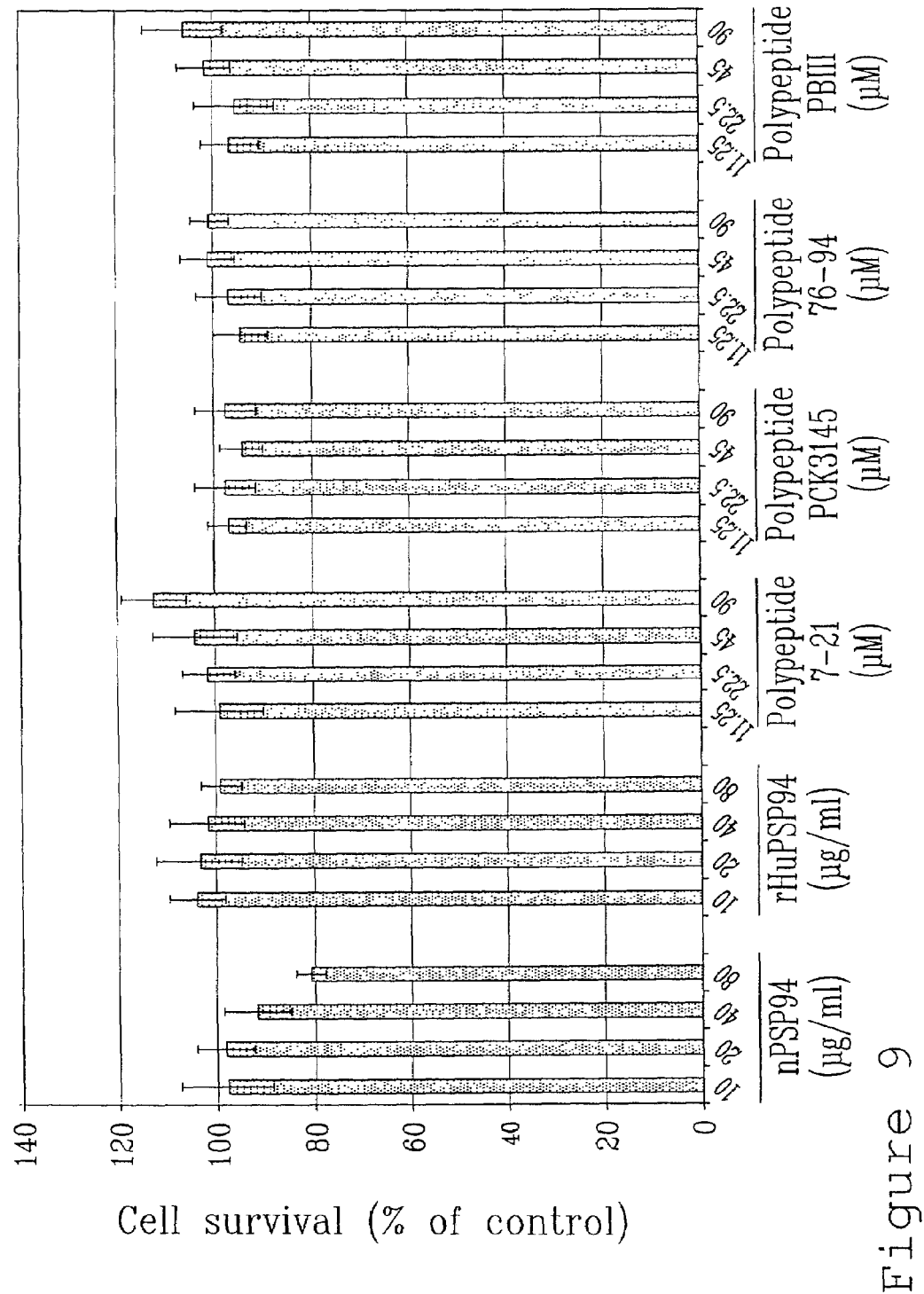
FIG. 9 is a graph depicting in vitro fibroblast cell growth when exposed for 72 hours to various concentration of native PSP94 (nPSP94) (SEQ ID NO: 1) or various concentration of rHuPSP94 (SEQ ID NO: 2) or polypeptide 7–21 (SEQ ID NO: 4), polypeptide PCK3145 (SEQ ID NO: 5), or polypeptide 76–94 (SEQ ID NO: 6).
Figure 10:
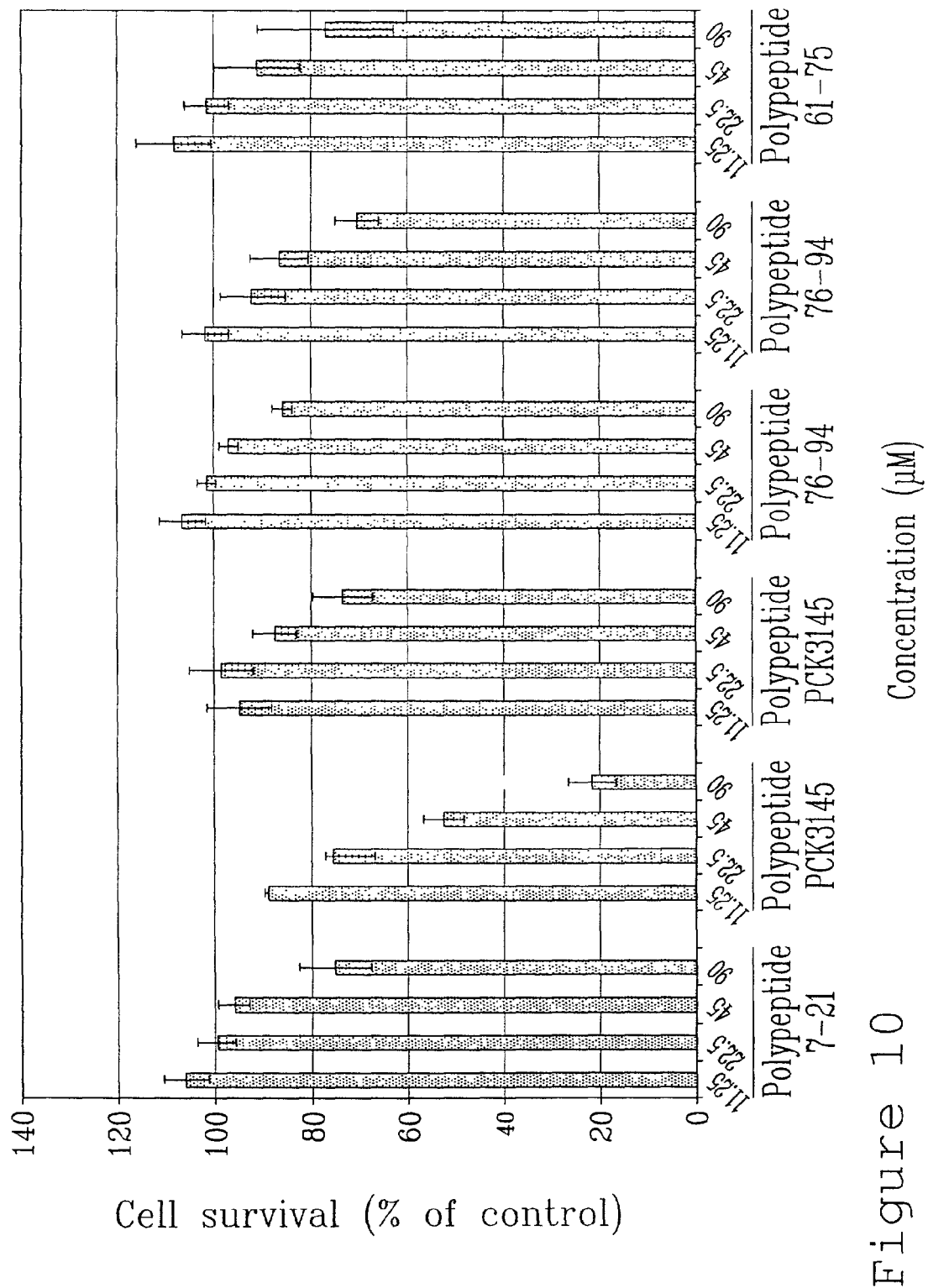
FIG. 10 is a graph depicting the effect of polypeptide 7–21 (SEQ ID NO: 4), polypeptide PCK3145 (SEQ ID NO: 5), polypeptide 76–94 (SEQ ID NO: 6), and polypeptide 61–75 on the in vitro growth of PC-3 cells after 72 hours.
Figure 11:
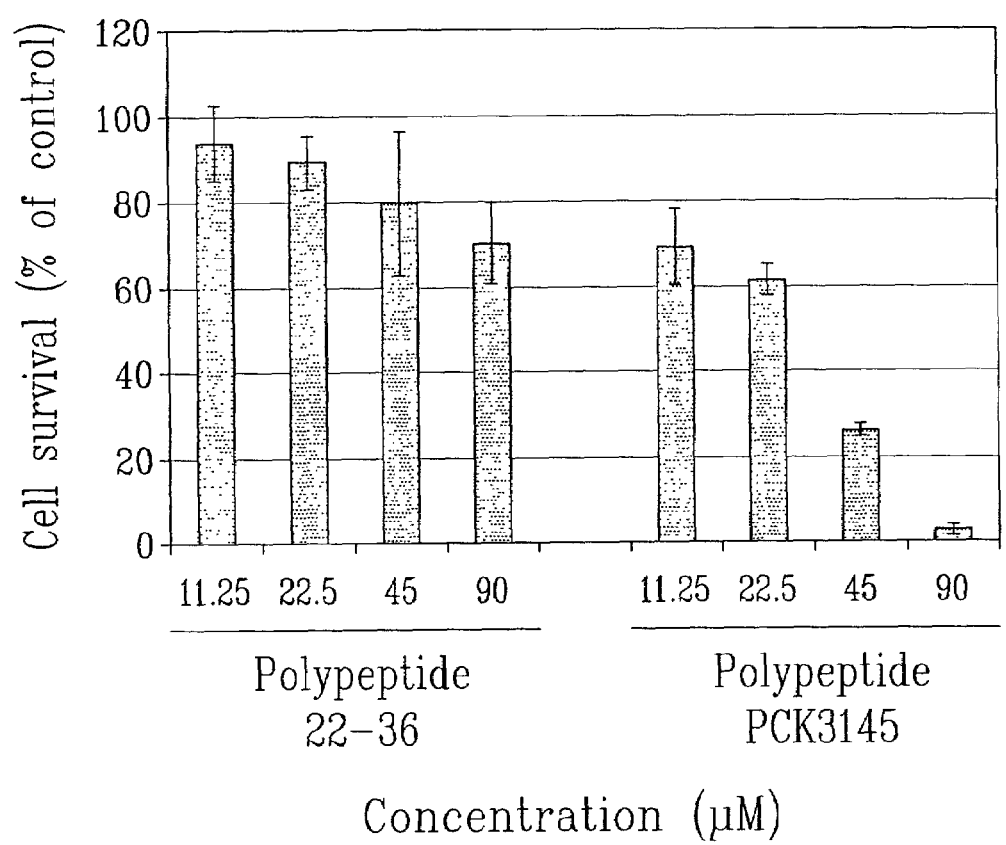
FIG. 11 is a graph depicting the effect of polypeptide 22–36 and polypeptide PCK3145 (SEQ ID NO: 5) on in vitro growth of PC-3 cells after 72 hours.

Inhibition of Cell-growth by PSP94 Polypeptides (FIGS. 9 to 11)

Biological activity of the polypeptides as set forth in SEQ ID NO: 4, SEQ ID NO: 5 and SEQ ID NO 6 was determined by their growth inhibitory effect on human prostate cancer cells PC-3. Native PSP94, rHuPSP94, polypeptide 22–36 and PB111 polypeptide (scrambled polypeptide) were also included in this experiment as controls. Cell proliferation assay was performed on either PC-3 cells or normal fibroblasts (used here as control) using the MTS/PMS kit (Promega). Four thousand cells (FIGS. 9 and 10) or three thousand (FIG. 11) cells were seeded in Costar 96 well cell culture flat bottom plates in RPMI supplemented media containing 50 μg/ml of bovine serum albumin (BSA) and 0.1 μM $FeSO_4$. In addition, monitoring of cell morphology was also performed.

Results of these experiments are shown in FIGS. 9 to 11. No cell inhibitory effect was observed following incubation of fibroblasts with various polypeptide concentrations (from 10 to 90 μM) for 72 hours (FIG. 9). However, a significant growth inhibition was observed for polypeptides as set forth in SEQ ID NO: 4 and SEQ ID NO: 6 and more importantly with polypeptide PCK3145 (SEQ ID NO: 5) (FIG. 10). Another experiment was performed using PCK3145 and polypeptide 22–36 at various concentrations on PC-3 cells, grown in OPTI-MEM media. In FIGS. 9 to 11, the percentage of growth inhibition given for treated cells is evaluated relative to non-treated control cells for which a value of 100% cell survival is given.

EXAMPLES 8 & 9

Figure 12:
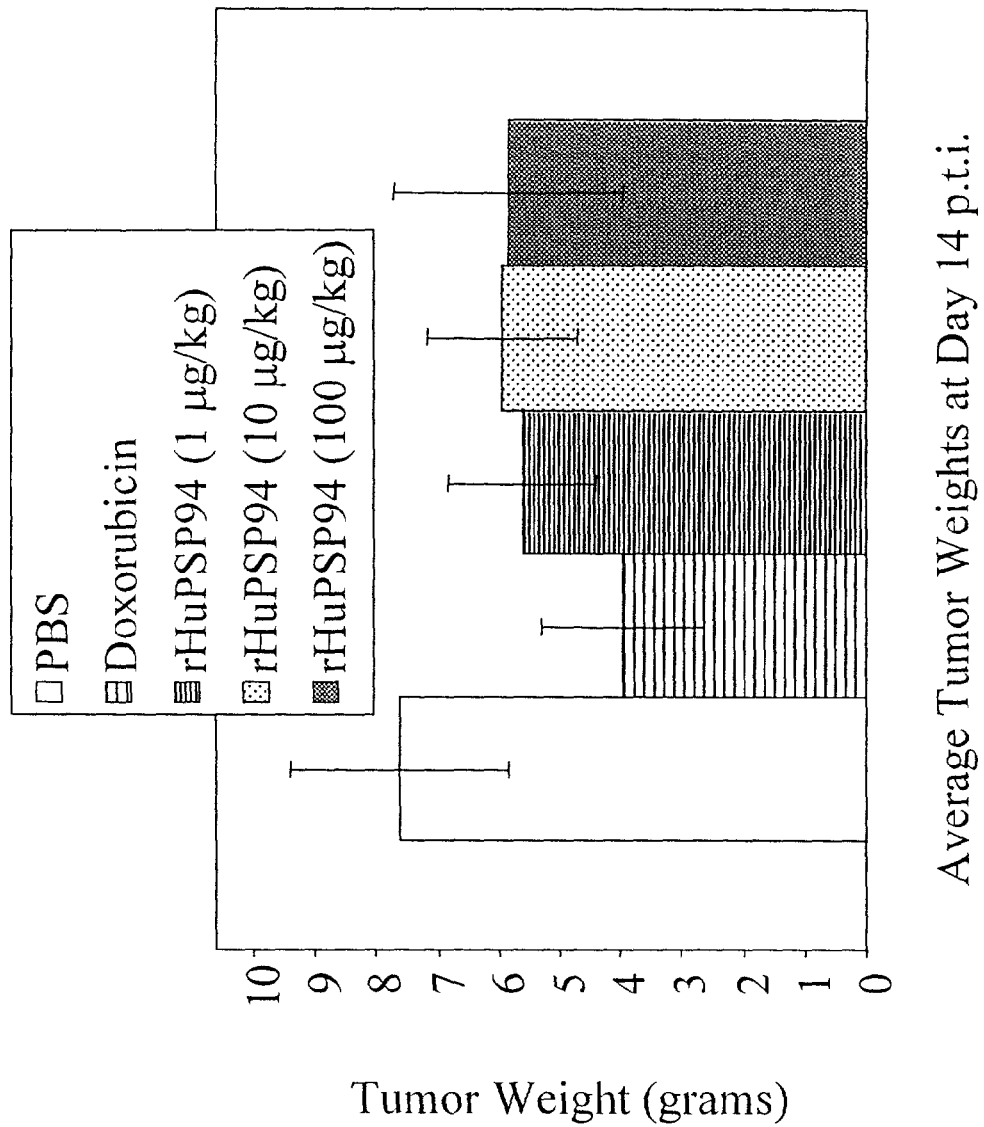
FIG. 12 is a graph depicting results of study no. MLL-1 on the anti-tumor efficacy validation of rHuPSP94 (rPSP94) (SEQ ID NO: 2) against Mat Ly Lu (MLL) tumor implanted in nude mice.
Figure 13:
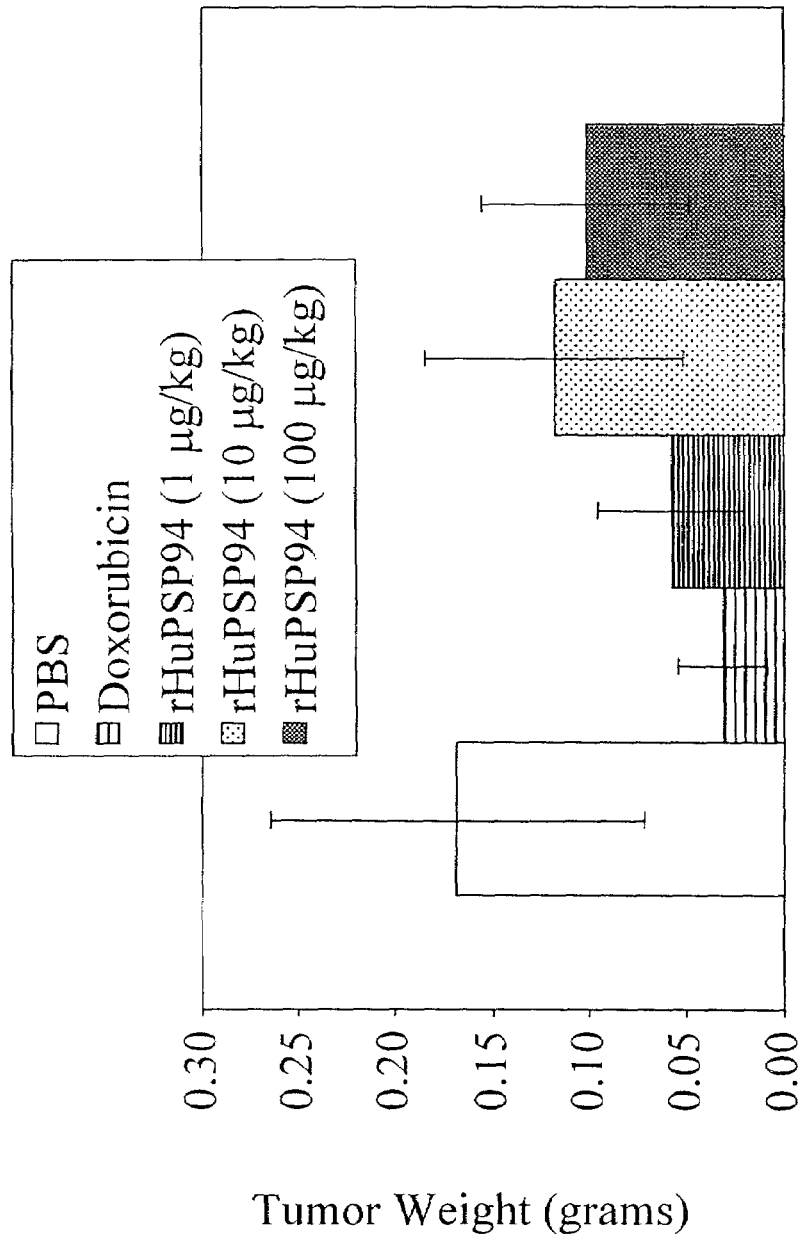
FIG. 13 is a graph depicting results of study no. MLL-2 on the anti-tumor efficacy validation of rHuPSP94 (rPSP94) (SEQ ID NO: 2) against Mat Ly Lu (MLL) tumor implanted in nude mice.

In-vitro Experiments (FIGS. 12 & 13)

Studies MLL-1 and MLL-2 were performed as follows; on day 0, male Copenhagen rats were injected subcutaneously with $5 \times 10^5$ Mat LyLu cells per rat. These cells were derived from cultures of Mat LyLu cell line grown in RPMI media containing 10% (v/v) of fetal calf serum in logarithmic phase of growth. Cells were harvested from the culture flasks by trypsinization, were centrifuged at 1200 rotation per minute (rpm) and washed three timed with Hanks balanced salt solution (HBSS). Following washing, cells were counted and adjusted to a concentration of $5 \times 10^6$ cells/ml in HBSS. A 0.1 ml volume of tumor cell inoculum containing $5 \times 10^5$ cells was administered subcutaneously into the flank region of each rat. Three days after tumor cell implantation (i.e., inoculation), animals were treated daily by a subcutaneous injection of the desired polypeptide until day 13.

Experiments illustrated in FIG. 12 show the anti-tumor efficacy validation of rHuPSP94 against Mat LyLu (MLL) tumor implanted in nude mice (Protocol based on S. Garde et al.; The Prostate, 22: 225–233, 1993).

For study MLL-1 (FIG. 12), tumor-implanted nude mice were separated in different groups, each receiving various amount of rHuPSP94 or control reagents. The different groups used in these experiments are illustrated below. Each group contained 8 mice.

Group 1: Negative control: PBS subcutaneously (s.c.)
Group 2: Positive control: Doxorubicin at 5 mg/kg intraveanously (i.v.) single bolus on day 3
Group 3: rHuPSP94 at 1 μg/kg/day (s.c.)
Group 4: rHuPSP94 at 10 μg/kg/day (s.c.)
Group 5: rHuPSP94 at 100 μg/kg/day (s.c.)

A schematic of inoculation is illustrated below; (Tumor cell implantation (T.C.I.), treatment (Tx), measurement (M), day (D)).

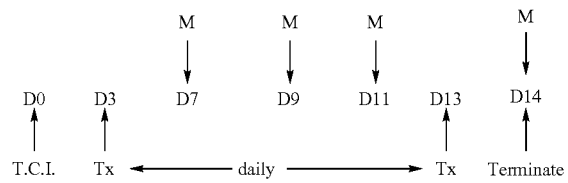

Experiments illustrated in study MLL-2 show the anti-tumor efficacy validation of rHuPSP94 against Mat Ly Lu (MLL) tumor implanted in severe combined immunodeficiency (SCID) mice (Protocol based on S. Garde et al.; The Prostate, 22: 225–233, 1993).

For study MLL-2 (FIG. 13), tumor-implanted Scid mice were separated in different groups each receiving various amounts of rHuPSP94 or control reagents. The different groups used in these experiments are illustrated below. Each group contained 8 mice.

Group 1: Negative control: PBS (s.c.)
Group 2: Positive control: Doxorubicin at 5 mg/kg i.v. single bolus on day 3

Group 3: rHuPSP94 at 1 µg/kg/day (s.c.)
Group 4: rHuPSP94 at 10 µg/kg/day (s.c.)
Group 5: rHuPSP94 at 100 µg/kg/day (s.c.)

A schematic of inoculation is illustrated below; (Tumor cell implantation (T.C.I.), treatment (Tx), measurement (M), day (D)).

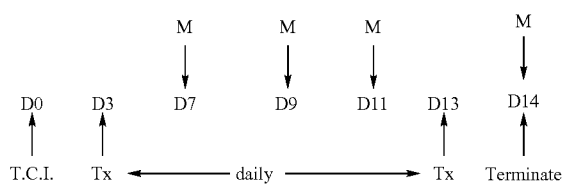

Results of those two studies indicate a difference in tumor size and growth in Nude vs SCID mice. The tumors grew slower and were smaller in SCID mice. This may be due to some specific factors controlling tumor growth in this mouse strain. Results also show a significant tumor reduction in mice injected with Doxorubicin (positive control). For example, tumor weight reduction in Nude mice (study MLL-1) injected with Doxorubicin was 48% (p=0.006)(p values measured by unpaired Student's t-test at p<0.05 as cut-off limit). Tumor weight reduction in SCID mice (study MLL-2) inoculated with Doxorubicin was 82% (p=0.002) (p values measured by unpaired Student's t-test at p<0.05 as cut-off limit). Results indicate also a significant tumor reduction in mice treated with rHuPSP94 at a concentration of 1 µg/kg/day. For example, tumor weight reduction in Nude mice (study MLL-1) treated with rHuPSP94 at a concentration of 1 µg/kg/day was 26% (p=0.042) (p values measured by unpaired Student's t-test at p<0.05 as cut-off limit). Tumor weight reduction in SCID mice (study MLL-2) treated with rHuPSP94 at a concentration of 1 µg/kg/day was 65% (p=0.010) (p values measured by unpaired Student's t-test at p<0.05 as cut-off limit).

EXAMPLE 10

Figure 14:
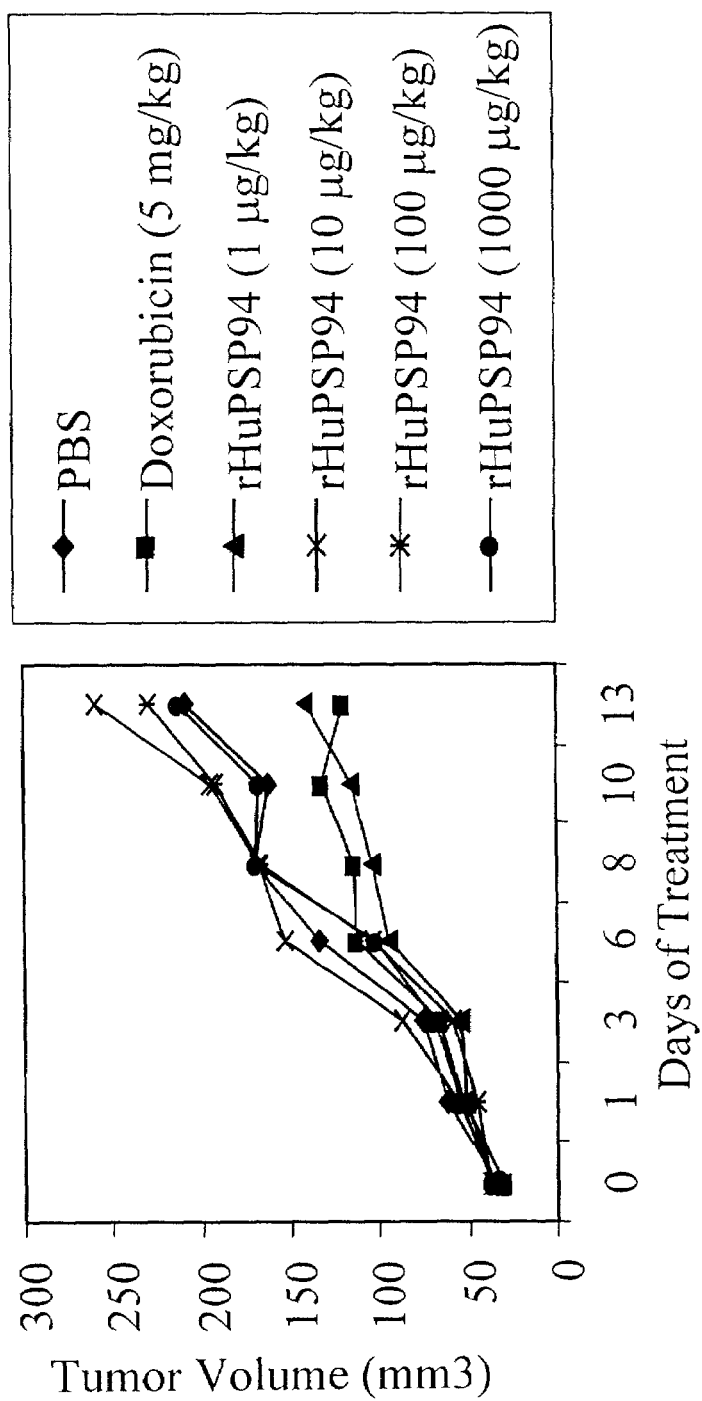
FIG. 14 is a graph depicting tumor volume (tumor growth reduction) in rHuPSP94-treated nude mice.

In-vivo Experiment using PC-3 Cell Line (FIG. 14)

PC-3 human prostate tumor was obtained from ATCC (ATCC 1435). PC-3 cells were grown in RPMI media containing 10% (v/v) of fetal calf serum and were harvested in the logarithmic phase of growth by trypsinization. Cells were centrifuged at 1200 rotation per minute (rpm) and washed three timed with Hanks balanced salt solution (HBSS). Following washing, cells were counted and adjusted to a concentration of $1\times10^7$ cells/ml in HBSS. A 0.1 ml volume of tumor cell inoculum containing $1\times10^6$ cells was administered subcutaneously into the two opposite flank region of each Nude mouse (Nu/Nu, BALB/c background). Tumor growth was monitored for approximately 18 days. Once tumor growth has been established (volume of tumor reached a volume of 50 mm$^3$) treatment with rHuPSP94 (SEQ ID NO: 2) was initiated and was performed once a day for 14 days by the subcutaneous route. Based on the assigned treatment groups illustrated in table 4.

TABLE 4

| Treatment group | Test control articles | Dose Level (µg/kg/day) | Dose concentration (µg/mg) | No. of animal |
|---|---|---|---|---|
| 1 Negative control | PBS | 0 | 0 | 8 |
| 2 Positive control | Doxorubicin | 5000 | 2500 | 8 |
| 3 | rHuPSP94 | 1 | 0.5 | 8 |
| 4 | rHuPSP94 | 10 | 5 | 8 |
| 5 | rHuPSP94 | 100 | 50 | 8 |
| 6 | rHuPSP94 | 1000 | 500 | 8 |

Results of this experiment (FIG. 14) demonstrated tumor growth reduction in the group of mice treated with rHuPSP94 at a dosage level of 1 µg/kg body weight per day. This reduction was similar to that observed for Doxorubicin (given at 5 mg/kg/day) which is a chemotherapeutic agent used as reference gold standard.

EXAMPLE 11

Figure 15:
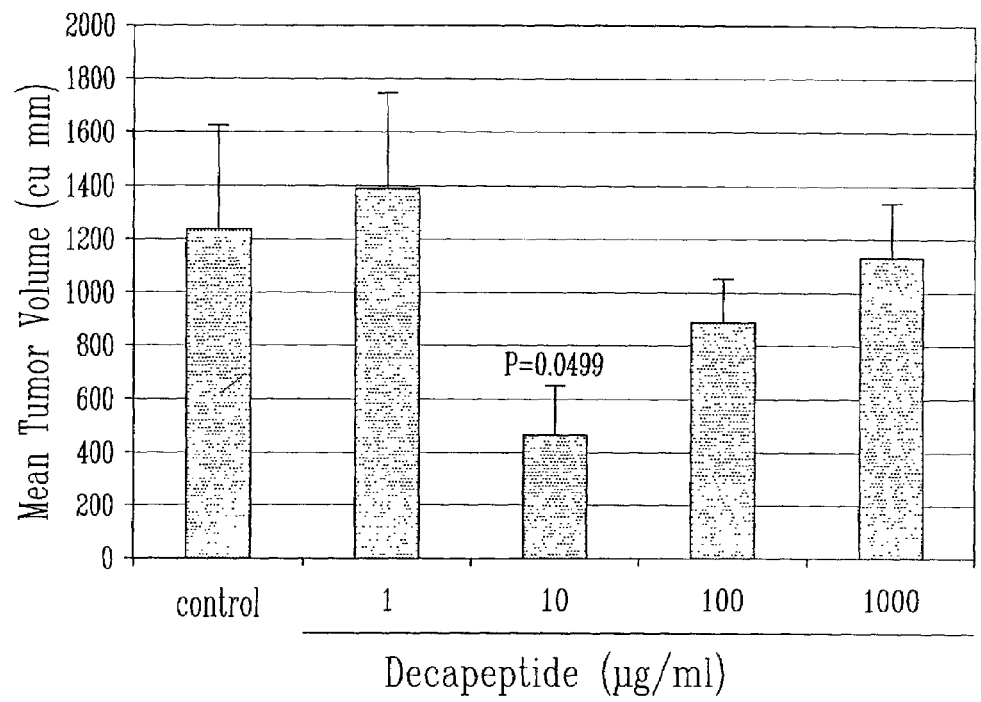
FIG. 15 is a graph depicting tumor volume (tumor growth reduction) in decapeptide (SEQ ID NO: 3)-treated nude mice.
Figure 16:
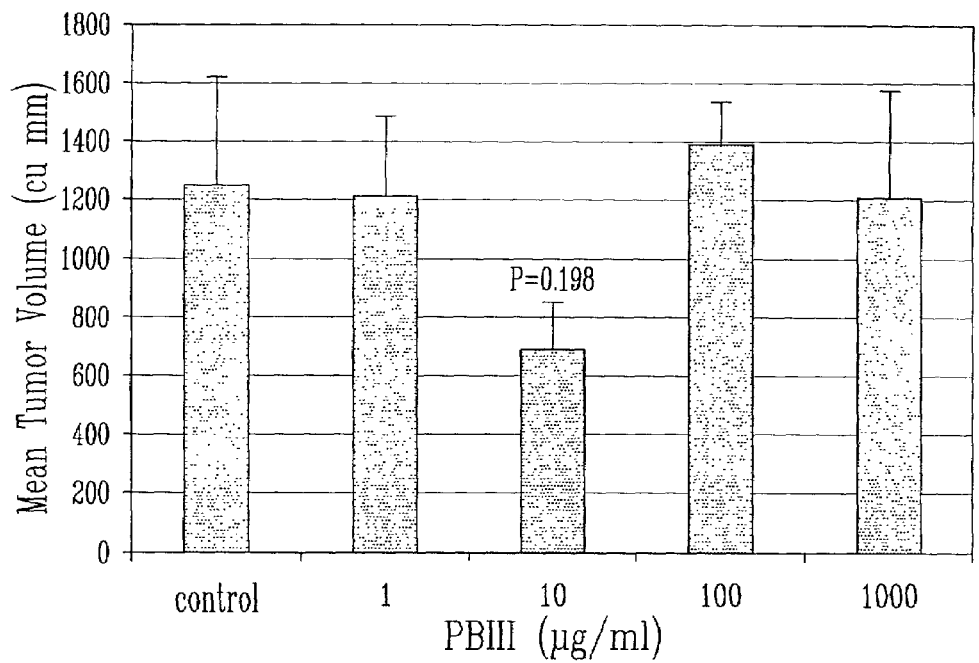
FIG. 16 is a graph depicting tumor volume (tumor growth reduction) in control scrambled polypeptide (PB111)-treated mice.
Figure 17:
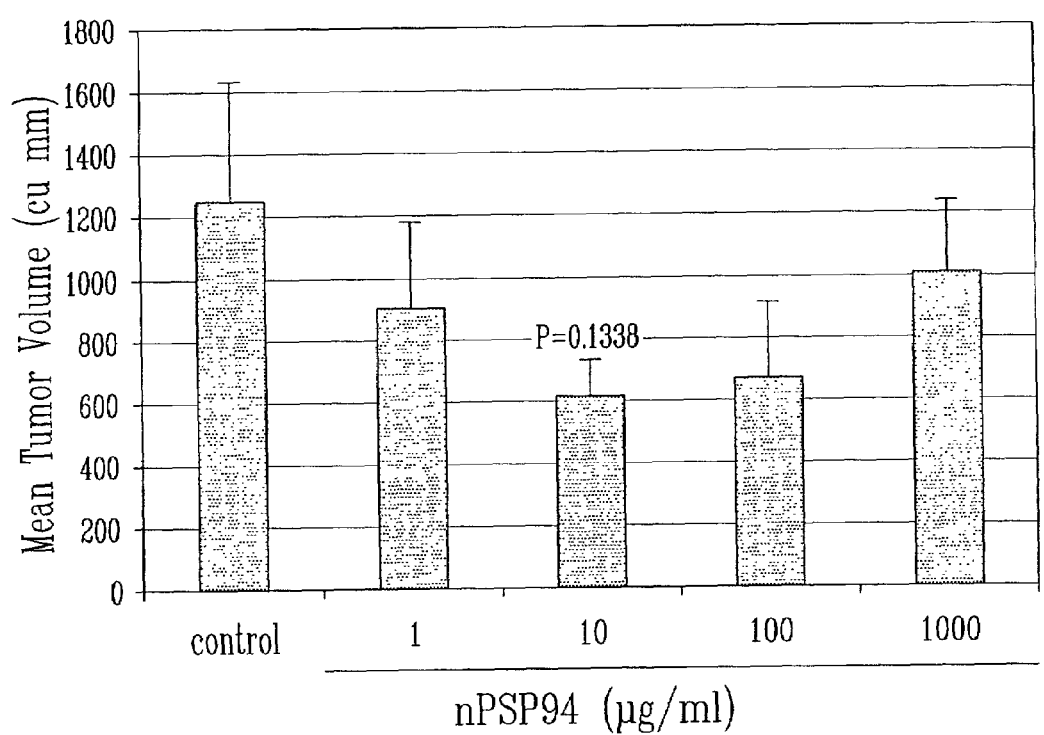
FIG. 17 is a graph depicting tumor volume (tumor growth reduction) in native-PSP94 (nPSP94)-treated mice.

In-vivo Experiment using PC-3 Cell Line (FIGS. 15–17)

PC-3 human prostate tumor (ATCC 1435) obtained from ATCC was implanted bilateraly into nude mice and tumor growth was monitored for approximately 18 days. PC-3 cells were injected once subcutaneously into each flank of the mice. Once tumor growth has been established (i.e., volume of tumor reached 0.25 to 0.50 cm$^3$) the treatment with decapeptide (SEQ ID NO: 3), native PSP94 (SEQ ID NO: 1) and control scrambled polypeptide PB111 was initiated and was performed once a day for 14 days by the subcutaneous route based on the treatment groups (randomly assigned) illustrated in table 5.

TABLE 5

| Treatment groups | Test and control articles | Dose Level (µg/kg/day) | Dose concentration (µg/mg) | No. of animal |
|---|---|---|---|---|
| 1 (Negative control) | PBS | 0 | 0 | 4 |
| 3 | Decapeptide (SEQ ID NO: 3) | 1 | 0.5 | 4 |
| 4 | Decapeptide (SEQ ID NO: 3) | 10 | 5 | 4 |
| 5 | Decapeptide (SEQ ID NO: 3) | 100 | 50 | 4 |
| 6 | Decapeptide (SEQ ID NO: 3) | 1000 | 500 | 4 |
| 7 | Native PSP94 (SEQ ID NO: 1) | 1 | 0.5 | 4 |
| 8 | Native PSP94 (SEQ ID NO: 1) | 10 | 5 | 4 |
| 10 | Native PSP94 (SEQ ID NO: 1) | 100 | 50 | 4 |
| 11 | Native PSP94 (SEQ ID NO: 1) | 1000 | 500 | 4 |
| 12 | Scrambled polypeptide (PB111) | 1 | 0.5 | 4 |
| 13 | Scrambled polypeptide (PB111) | 10 | 5 | 4 |
| 14 | Scrambled polypeptide (PB111) | 100 | 50 | 4 |
| 15 | Scrambled polypeptide (PB111) | 1000 | 500 | 4 |

FIG. 15 represents results obtained for tumor-implanted nude mice treated with the decapeptide (SEQ ID NO: 3) compared to a non-treated control. FIG. 16 represents results obtained for tumor-implanted nude mice treated with scrambled polypeptide PB111 compared to a non-treated control. FIG. 17 represents results obtained for tumor-implanted nude mice treated with native PSP94 (SEQ ID NO: 1) compared to a non-treated control. Results of these experiments (FIGS. 15–17) indicate a significant ($p<0.05$) tumor growth reduction in mice treated with the decapeptide (SEQ ID NO: 3) at a dosage level of 10 µg/kg body weight per day.

EXAMPLE 12

Manufacturing and Preparation of Polypeptides

PSP94 derived polypeptides including PCK3145 (SEQ ID NO: 5) were synthesized using the FMOC and BOC solid phase polypeptide synthesis method (Merrifield, B., Science, 232: 341–347, 1986). Polypeptides were analyzed in order to determine their identity by Mass Spectral Analysis. Polypeptide samples were analyzed using the PerSeptive Biosystems (Framingham, Mass.), with Voyager-DE MALDI-TOF mass spectrometer using 337 nm light from a nitrogen laser. About 50 scans were averaged for each analysis. A sample from the native PSP94 was also analyzed under similar conditions for comparison. Polypeptides were weighed on a Mettler AE 163 micro-balance. The measurements were to nearest 0.1 mg. The polypeptides were reconstituted in 10 mM PBS pH 7.3 to a final concentration of 1 and 5 mg/ml. The polypeptides dissolved relatively well and were filter sterilized through a 0.2 µM syringe filter. Aliquots of 2 ml/tube were made and stored at –80° C.

The pH of the polypeptides was measured after reconstitution to ensure that possible differences in pH would not be a factor of variation. The pH values of each solution were taken at three concentrations: neat, 100 µg/ml and 12.5 µg/ml. The pH range was approximately from 7.0 to 7.5. This did not make a significant difference in the outcome of the test as cells survive very well within this pH range. To change the concentrations to molar values, the approximate volume of the 1 mg/ml stocks were diluted in PBS pH 7.3. All stocks were made to contain 450 µM polypeptide solutions. When fresh stocks of polypeptide were to be reconstituted, it was done directly to 450 µM concentration in PBS pH 7.3.

After our initial screening and confirmation of the inhibitory activity of the polypeptide on the growth of the PC-3 cells, a GMP manufactured polypeptide was tested. This polypeptide was weighed and dissolved in PBS and 2 mg/ml stock solution was prepared, sterile filtered through a 0.2 µm syringe filter and stored at in –80° C.

EXAMPLE 13

Effect of PCK3145 on In-vitro PC-3 Cells (MTS Assay (FIGS. 18–21))

PCK3145, manufactured as set forth in example 12, was evaluated as a lead candidate product in tumor growth inhibition.

The biological activity of PCK3145 was determined by its growth inhibitory effect on the human prostate cancer cell line PC-3 using the MTS/PMS kit (Promega). This assay measures the mitochondrial activity of the live cells. The basic principle of this method involves the fact that the mitochondrial enzymes of the live cells metabolize the MTS/PMS dyes forming a brown colored precipitate which can be measured as optical density (OD) by absorption at 490 nm in a spectrophotometer. Therefore, the OD values are proportional to the number of living cells.

Figure 18:
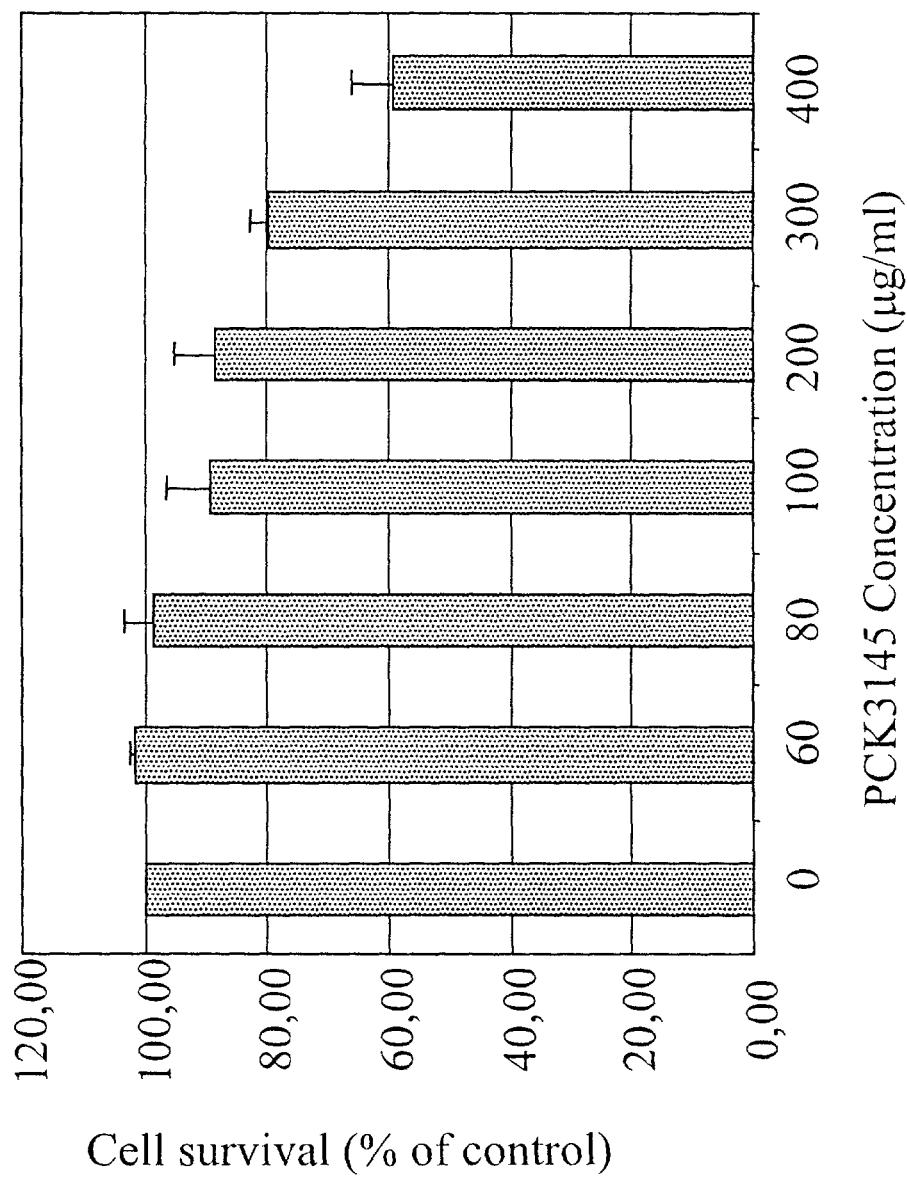
FIG. 18 is a graph depicting the in vitro inhibitory activity of PCK3145 (SEQ ID NO: 5) on PC-3 cells, after a 72 hours treatment, as measured by MTS (3-(4,5-dimethylthiazol-2-yl)-5-(3-carboxymethoxyphenyl)-2-(4-sulfophenyl)-2H-tetrazolium,inner salt) assay.

In addition, a visual observation of the cells was also done to check the cell morphology, which could also be indicative of cell growth. The following conditions for MTS assay were used: PC-3 (ATCC, Lot AT06), passage number $n \geq 70$, cell line adapted to grow in serum-free OPTI-MEM and in RPMI supplemented with BSA (50 µg/ml) and Ferrous Sulfate (0.1 µM), continuous exposure for up to 72 hours without changing media (i.e., adding PCK3145 at 2× concentration directly to wells and diluting it 1:2 to 1× to minimize cell manipulation and avoid detachment). As indicated in FIG. 18, PCK3145 was assessed at the following concentrations: 12.5, 25, 50, 100, 200, 300 and 400 µg/ml on PC-3 cells (ATCC) grown in supplemented media. The MTS tests were repeated 5 times and a dose dependent inhibitory effect on the growth of PC-3 cells was consistently reproducible demonstrating approximately 40% cell growth inhibition at the highest PCK3145 concentration of 400 µg/ml.

Figure 19:
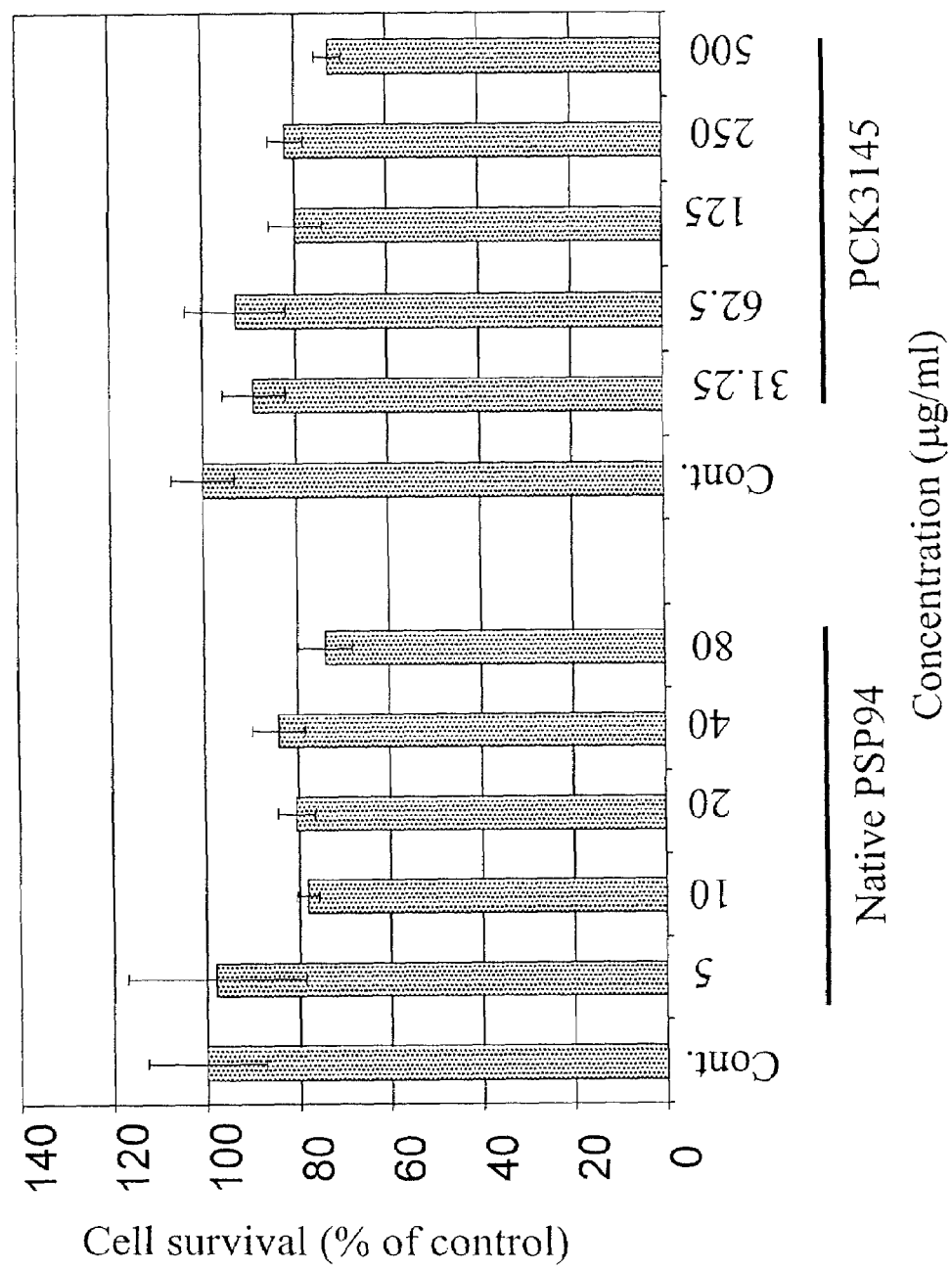
FIG. 19 is a graph depicting the in vitro inhibitory activity of native PSP94 (SEQ ID NO: 1) and PCK3145 (SEQ ID NO: 5) (GMP grade) on PC-3 cells, after 48 hours of treatment, as measured by MTS assay.
Figure 20:
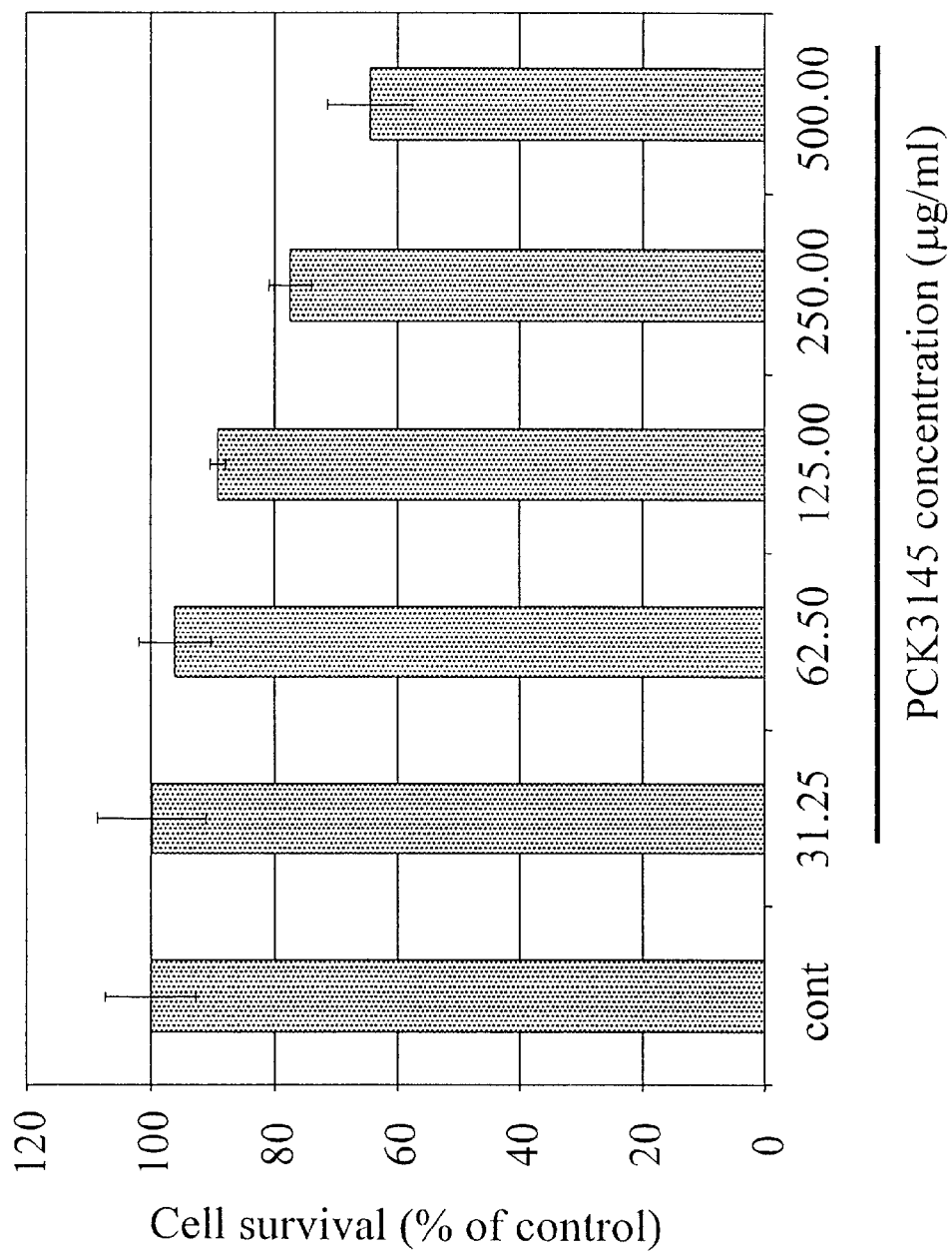
FIG. 20 is a graph depicting the in vitro inhibitory activity of PCK3145 (SEQ ID NO: 5) (GMP grade) on PC-3 cells (ATCC), after 72 hours of treatment, as measured by the MTS assay.
Figure 21:
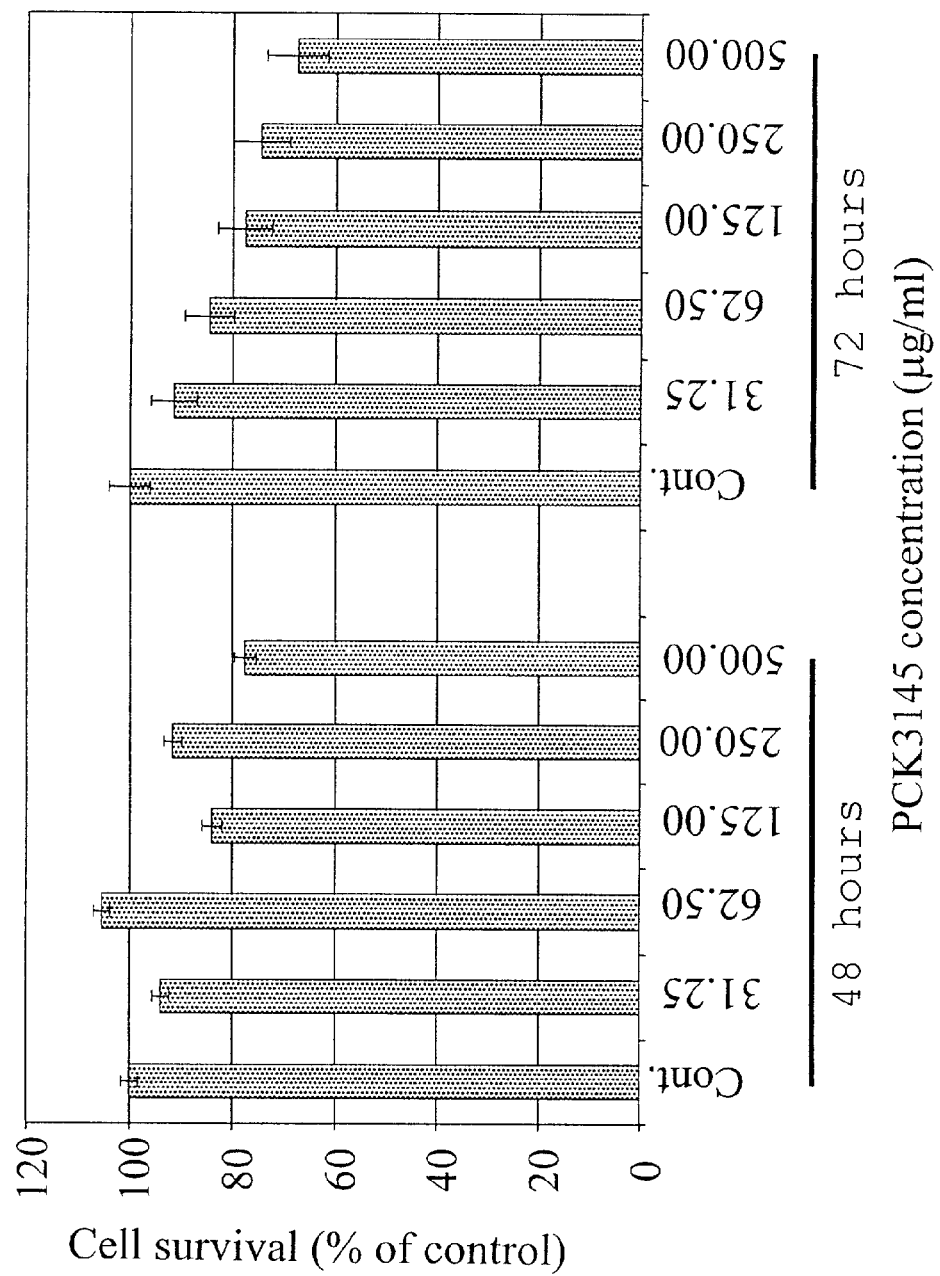
FIG. 21 is a graph depicting the in vitro inhibitory activity of PCK3145 (SEQ ID NO: 5)(GMP grade) on PC-3 cells (ATCC), after a 48 or 72 hours treatment, as measured by the MTS assay.

With the availability of GMP (good manufacturing practice) grade polypeptide the MTS assays were repeated to check the reproducibility and cytotoxicity against PC-3 cells. In parallel PC-3 cells were also treated with the native PSP94 as a reference positive control and with no treatment (negative control, i.e., cont.). FIG. 19 shows the results of the MTS assay where 4000 cells were seeded and exposed to PCK3145 (GMP grade) for 48 hours. A 30% growth inhibitory effect was observed following treatment with PCK3145 at 500 µg/ml. This effect was increased to approximately 40% after 72 hours of exposure (FIG. 20). In a repeat experiment a 48 hours exposure to the polypeptide at 500 µg/ml resulted in only 20–22% growth inhibition, however this effect increased to 30% after 72 hours exposure (FIG. 21). Despite assay to assay variability reflected by the state of cell growth in vitro, polypeptide PCK3145 exhibited a significant cell growth inhibition.

EXAMPLE 14

Figure 22:
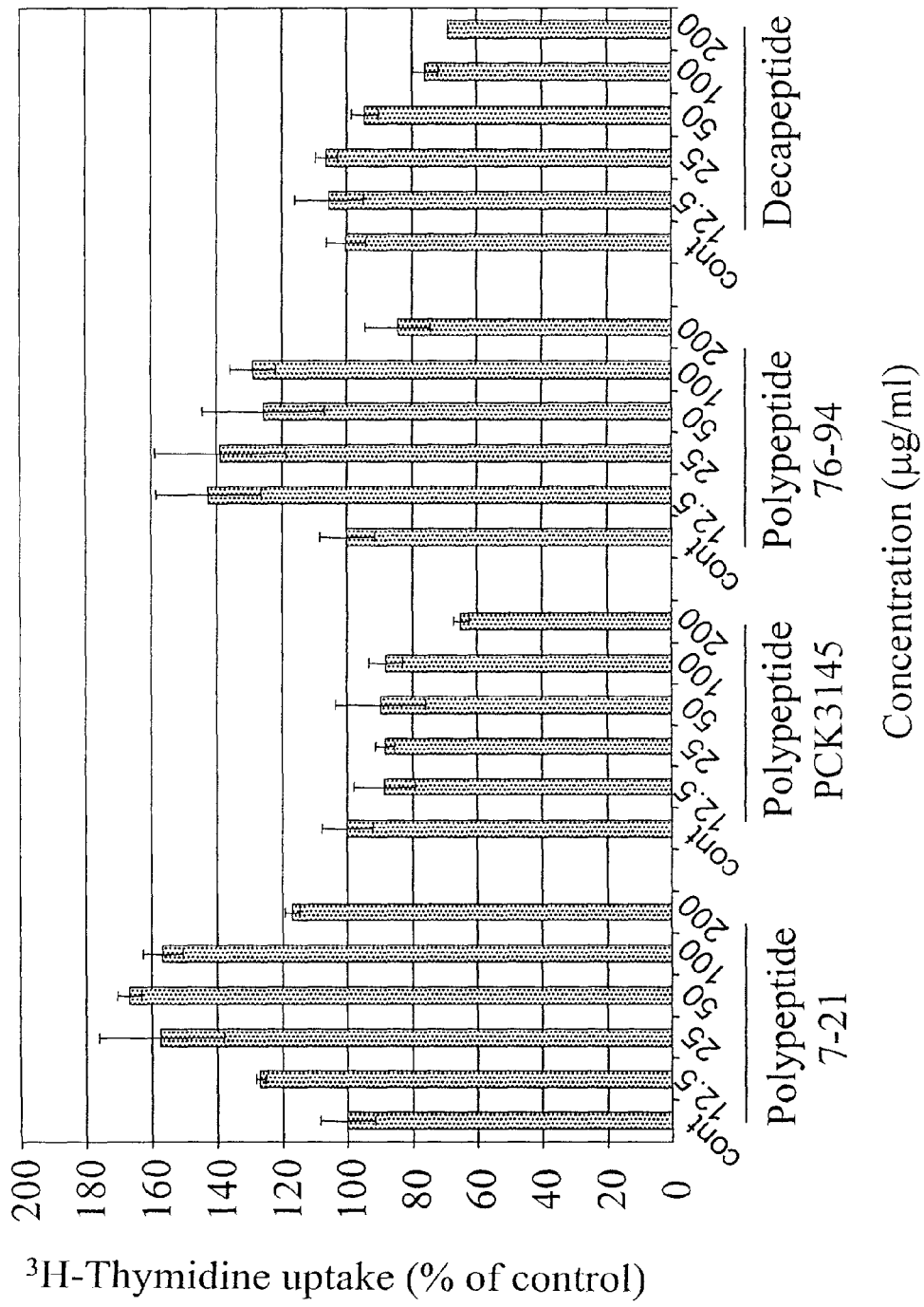
FIG. 22 is a graph depicting the in vitro inhibitory activity of decapeptide as set forth in SEQ ID NO: 3, polypeptide 7–21 as set forth in SEQ ID NO: 4, polypeptide PCK3145 as set forth in SEQ ID NO: 5, or polypeptide 76–94 as set forth in SEQ ID NO: 6 on PC-3 cells, measured by [$^3$H]-Thymidine uptake assay.

Effect of PCK3145 on In-vitro PC-3 Cells [$^3$H]-Thymidine Uptake Assay (FIGS. 22–24)

[$^3$H]-Thymidine uptake assay involves [$^3$H]-Thymidine incorporation into cellular DNA of actively proliferating cells. [$^3$H]-Thymidine uptake assay measures the proliferative index of the cells versus the MTS assay, which quantifies the number of lived cells following treatment. The anti-proliferative effects of PCK3145 and two other synthetic polypeptides derived from the amino and carboxy terminus ends of PSP94 (SEQ ID NO: 4 and NO: 6, respectively) as well as the decapeptide (SEQ ID NO: 3) previously shown to mimic the biological action of native PSP94 were assessed in [H3]-Thymidine uptake assay on PC-3 cells. Two separate experiments were conducted with GMP-grade PCK3145.

As shown in the FIGS. 22 and 23, polypeptide PCK3145 exhibited a significant proliferation inhibition activity reflected in the percentage of [H3]-Thymidine uptake. In the first experiment, a reduction of nearly 40% in [$^3$H]-Thymidine uptake was observed at PCK3145 concentration of 200 µg/ml. In the second experiment, although a two fold higher concentration of the PCK3145 was used (i.e., 400 µg/ml) only a 25% inhibition was observed. Despite assay to assay variation the overall degree of proliferative inhibitory effect against PC-3 cell was markedly evident with the GMP grade material. Treatment of PC-3 cells with the native PSP94 used as a positive reference standard, exhibited a significant dose dependent reduction in cell proliferation with almost 50% reduction in the [H3]-Thymidine uptake following 72 hours exposure (FIG. 24).

EXAMPLE 15

In Vitro Effect of PCK3145 on PC-3 Cells (Apoptosis-FIG. 25)

Apoptosis of PC-3 cells, following a 72 hours exposure to PCK3145 at 500 µg/ml concentration, was evaluated in supplemented media by DNA fragmentation assay. Doxorubicin was used as a reference positive control. Untreated cells and PCK3145-treated cells were harvested and the DNA was isolated. Isolated DNA was run on a 1.2% agarose gel containing Ethidium Bromide (EtBr). As shown in FIG. 25 treatment of PC-3 cells with polypeptide PKC3145 resulted in DNA fragmentation evidenced by the ladder formation seen for fragmented DNA. Lane 1 of the gel illustrated in FIG. 25 represents the DNA marker (100 base pair DNA ladder). Lane 2 of the gel illustrated in FIG. 25 represents a control of untreated PC-3 cells. Lane 3 of the gel illustrated in FIG. 25 represents DNA laddering effect observed for cells treated with doxorubicin at a concentration of 2 µg/ml. Lane 4 of the gel illustrated in FIG. 25 represents DNA laddering effect observed for cells treated with PCK3145 (SEQ ID NO: 5).

EXAMPLE 16

In Vivo Experiments using Human PC-3 Prostate Cancer Cell Line (FIGS. 26–27)

Studies PC3-6 and PC3-12 (FIGS. 26–27) are consecutive group experiments designed to characterize the in vivo activity of PCK3145 in the human PC-3 prostate cancer nude mouse xenograft model and to explore relationships between dose, route and schedule of administration and the efficacy parameters of tumor growth (volume).

PC-3 cells harvested in mid-log phase were inoculated at $5 \times 10^6$ cells per mice via the subcutaneous route in the mice's back area. Tumors grown from this inoculum were excised at approximately day 32 to 35 post-tumor implantation (p.t.i) when tumor volume reached 200–300 MM$^3$ (i.e., cu mm). The necrotic tissue was removed and the viable tumor mass cut into small pieces (approximately 1 to 3 mm$^3$) were implanted SC in the flank region at two opposite sites of the mouse. Treatment with various concentrations of PCK3145 was initiated at day 3 post-tumor implantation (p.t.i) and was continued daily for 21 days. Subcutaneous injections were done below tumor growth sites. Intra-peritoneal injections were performed in the abdominal region. Intra-venous injections were performed via the lateral tail vein. The experiment was terminated 24 hours after the last treatment. Tumor measurements were taken at Days 11, 14, 16, 18, 20, 22 and 24 post-tumor implantation (p.t.i). Tumor volumes were calculated according to formula $(a \times b^2 \times 0.5)$, where a—is the length of the long diameter, and b—is the width of the perpendicular small diameter.

Study No: PC3-6 illustrates the efficacy of PCK3145, injected subcutaneously, in tumor growth retardation in Nude mice, which have received PC-3 implants. Mice were separated in different group each receiving various amounts of PCK3145 (SEQ ID NO: 5) or control reagents. The different groups used in these experiments are illustrated in table 6 below. Each group contained 10 mice. Doxorubicin was administered as single bolus intra-venous injection on days 3 and 11 post-tumor implantation (p.t.i).

TABLE 6

| Treatment group | Test and control articles | Dose Level (µg/kg/day) | No. of animals | No. of tumors |
|---|---|---|---|---|
| 1 Negative control | PBS | 0 | 10 | 20 |
| 2 Positive control | Doxorubicin | 10000 | 10 | 20 |
| 3 | PCK3145 | 0.1 | 10 | 20 |
| 4 | PCK3145 | 1 | 10 | 20 |
| 5 | PCK3145 | 10 | 10 | 20 |

Results of this study (FIG. 26) demonstrated a significant PC-3 tumor growth retardation following treatment with PCK3145 at 10 µg/kg/day. This anti-tumor effect was evidenced by a statistically significant decrease in percentage of tumor growth observed at days 11, 14, 16, 18, 21 and 24 after tumor implantation with respective p-values ranging from p=0.001 to 0.002, in comparison to the control PBS-treated group (p values measured by unpaired Student's t-test at p<0.05 as cut-off limit). Doxorubicin, a potent chemotherapeutic agent, was used as reference gold standard and demonstrated a highly significant anti-tumor therapeutic effect. ANOVA analysis of variance, Dunnett's test, Kruskal-Wallis and Dunn's test analysis of data confirmed statistical significance of the observed anti-tumor effect.

Study No: PC3-12 illustrates the efficacy of PCK3145 in tumor growth retardation in Nude mice, which have received PC-3 implants. Mice were separated in different group each receiving various amounts of PCK3145 (SEQ ID NO: 5) or control reagents. PCK3145 was injected either through intra-venous or intra-peritoneal route. The different groups used in these experiments are illustrated in table 7 below. Each group contained 9 mice.

TABLE 7

| Treatment groups | Test and control articles | Dose level (µg/kg/day) | No. of animals | No. of tumors |
|---|---|---|---|---|
| 1 Negative control | PBS | 0 | 9 | 18 |
| 2 | PCK3145 IV | 10 | 9 | 18 |
| 3 | PCK3145 IV | 100 | 9 | 18 |
| 4 | PCK3145 IV | 500 | 9 | 18 |
| 5 | PCK3145 IV | 1000 | 9 | 18 |
| 6 | PCK3145 IP | 100 | 9 | 18 |
| 7 | PCK3145 IP | 1000 | 9 | 18 |

Results of this experiment (FIG. 27) demonstrated a significant tumor growth retardation following treatment with PCK3145 at 100 µg/kg/day via the intra-venous route. This effect was statistically significant at days 13, 17 and 20 after tumor implantation when compared by Student's t-test (p-values were p=0.005, 0.025 and 0.011, respectively for each time-point) (p values measured by unpaired Student's t-test at p<0.05 as cut-off limit). No significant anti-tumor effect was observed following PCK3145 treatment at the other dosage levels of 10, 500 and 1000 µg/kg/day injected via the intra-venous route. However a trend towards significance was observed following treatment with 500 and 1000 µg/kg/day doses of PCK3145. Treatment of mice with PCK3145 at 100 and 1000 µg/kg/day administered via the intra-peritoneal route showed a similar tumor growth retardation trend with statistically less significant difference observed at day 13 p.t.i (p=0.056) (p values measured by unpaired Student's t-test at p<0.05 as cut-off limit) at the highest dose of 1000 µg/kg/day (FIG. 27).

During the course of experimentation using the human PC-3 prostate cancer nude mouse xenograft model, results obtained have suggested that subcutaneous PCK3145 injection of mice at a site (i.e., scruff of the neck) distant from tumor site, might not be efficacious enough and will unlikely may unlikely result in an anti-tumor effect, at least in the experimental conditions tested (doses of PCK3145 tested: 10 µg/kg/day and 100 µg/kg/day). The use of the scruff of the neck as a subcutaneous injection site represents an optimal site for immune response induction rather than a route for therapeutic product administration and as such, selection of this site is expected to be a sub-optimal site for tumor efficacy evaluation.

EXAMPLE 17

In Vivo Experiments using Dunning Rat Mat Ly Lu Prostate Cancer Line (FIGS. 28–30)

Anti-tumor efficacy evaluation of PCK3145 against Mat Ly Lu (MLL) tumor implanted in Copenhagen rats was performed. (Protocol based on S. Garde et al.; The Prostate, 22: 225–233, 1993). Mat LyLu tumor cells were harvested in mid-log phase from the culture flasks by trypsinization, were centrifuged at 1200 rotation per minute (rpm) and washed three timed with Hanks balanced salt solution (HBSS). Following washing, cells were counted and adjusted to a concentration of $5 \times 10^6$ cells/ml in HBSS. A 0.1 ml volume of tumor cell inoculum containing $5 \times 10^5$ cells was administered subcutaneously into the flank region of each rat. Treatment started at day 3 post-tumor implantation (p.t.i) by local subcutaneous injection (i.e., in the shaved back area just below tumor implantation site) of various PCK3145 concentrations. This treatment was continued daily for 16 days. Experiments were terminated 24 hours after the last treatment. Tumor measurements were taken at days 7, 9, 11, 14, 16 and 18. Tumor volumes are calculated according to formula $(a \times b^2 \times 0.5)$, where a—is the length of the long diameter, b-width of the perpendicular small diameter. At day 19 tumors of individual rats were excised and weighed.

Study No: MLL-5 illustrates the efficacy of PCK3145 (SEQ ID NO: 5) compared with polypeptide 7–21 (SEQ ID NO: 4) and polypeptide 76–94 (SEQ ID NO: 6) in tumor growth retardation in Copenhagen rats, which have received Mat Ly Lu implants. Mice were separated in different groups, each receiving various amount of PCK3145 (SEQ ID NO: 5) or control reagents. PCK3145 was injected through the subcutaneous route. The different groups used in these experiments are illustrated in table 8 below. Each group contained 8 mice.

TABLE 8

| Treatment groups | Test and control articles | Dose Level (µg/kg/day) | No. of animals | No. of tumors |
|---|---|---|---|---|
| 1 Negative control | PBS | 0 | 8 | 8 |
| 2 | Polypeptide 7-21 | 10 | 8 | 8 |
| 3 | Polypeptide 7-21 | 1 | 8 | 8 |
| 4 | PCK3145 | 10 | 8 | 8 |
| 5 | PCK3145 | 1 | 8 | 8 |
| 6 | Polypeptide 76-94 | 10 | 8 | 8 |
| 7 | Polypeptide 76-94 | 1 | 8 | 8 |

Results of this study (FIG. 28) demonstrated a significant anti-tumor effect following administration of PCK3145 at 10 µg/kg/day. This was evidenced by a significant tumor volume reduction at days 11 (p=0.006), 13 (p=0.00001), 16 (p=0.002) and 18 (p=0.004), post-tumor cell implantation compared to control PBS-treated group (p values measured by unpaired Student's t-test at p<0.05 as cut-off limit). No significant effect was detectable following PCK3145 treatment at 1 µg/kg/day. It was of interest to note that the amino-terminus polypeptide 7–21 also demonstrated comparable anti-tumor effect, which was also observed in the PC-3 nude mouse xenograft model, indicating the possibility of an overlapping active site between the N-terminus and the central regions of the PSP94 protein. This was evidenced by a significant tumor volume reduction observed at day 13 (p=0.05), 16 (p=0.00005), and 18 (p=0.01) in mice treated with polypeptide 7–21 (p values measured by unpaired Student's t-test at p<0.05 as cut-off limit).

Study No: MLL-6 illustrates the efficacy of PCK3145 (SEQ ID NO: 5) in tumor growth retardation in Copenhagen rats, which have received Mat Ly Lu implants. Mice were separated in different group each receiving various amounts of PCK3145 (SEQ ID NO: 5) or control reagents. PCK3145 was injected through the subcutaneous route. The different groups used in these experiments are illustrated in table 9 below. Each group contained 8 mice. Doxorubicin was administered as single bolus via intra-venous injection on day 3 p.t.i.

TABLE 9

| Treatment groups | Test and control articles | Dose level (µg/kg/day) | No. of animals | No. of tumors |
|---|---|---|---|---|
| 1 (Negative control) | PBS | 0 | 8 | 8 |
| 2 | Doxorubicin | 5000 | 8 | 8 |
| 3 | PCK3145 | 10 | 8 | 8 |
| 4 | PCK3145 | 100 | 8 | 8 |
| 5 | Scrambled polypeptide | 10 | 8 | 8 |
| 6 | Scrambled polypeptide | 100 | 8 | 8 |

Results of this study (FIGS. 29 and 30) demonstrated a significant dose-dependent anti-tumor effect following administration of PCK3145 at 10 and 100 µg/kg/day. This was evidenced by a significant tumor volume reduction (31% over control) following PCK3145 treatment especially with 100 µg/kg/day at days 14, 16 and 18 post-tumor cell implantation (FIG. 29). The p-value versus negative control-treated group (i.e., scrambled polypeptide (PB111)) was highly significant at p=0.0000062 (p values measured by unpaired Student's t-test at p<0.05 as cut-off limit). A moderate extent of growth retardation (marginal statistical significance at p=0.03 versus control PBS-treated group) was also observed following treatment with scrambled polypeptide at a concentration of 100 pg/kg/day (FIG. 29) (p values measured by unpaired Student's t-test at p<0.05 as cut-off limit). Doxorubicin treatment was highly significant resulting in over 80% reduction in tumor volumes. This anti-tumor effect of PCK3145 at 100 µg/kg/day was also reproduced following analysis of the tumor weights data. As shown in FIG. 30, (tumor weight data) a significant reduction in tumor weights (p=0.0003) was observed on day 18 p.t.i (p values measured by unpaired Student's t-test at p<0.05 as cut-off limit). This represented a 34% reduction in tumor mass, a 20 gram difference between the control (56.6 g) and PCK3145-treated at 100 µg/kg/day group (37.2 g). This difference in tumor weights was also statistically significant when it was compared to the tumor weights of the control scrambled polypeptide-treated rats given the same dose of 100 µg/kg/day (p=0.003) (p values measured by unpaired Student's t-test at p<0.05 as cut-off limit). Comparison of the scrambled polypeptide treated tumor weights with that of control PBS-untreated tumor weights was not statistically significant (p=0.06) (p values measured by unpaired Student's t-test at p<0.05 as cut-off limit).

EXAMPLE 18

Efficacy of PCK3145 and Taxotere Combination Treatment

In order to test for the efficacy of combination treatment, in tumor growth retardation, PCK3145 and taxotere (i.e., docetaxel) were co-administered in Nude mice previously inoculated with PC-3 tumor cells. Mice were separated in different groups each receiving PCK3145 alone or PCK3145 in combination with taxotere (administered by separate routes) or control reagent (i.e., PBS). In this experiment, the combination treatment was initiated against relatively large tumor burdens. Tumors were allowed to grow beyond the 50 to 60 mm$^3$ size at which PCK3145 treatment usually becomes inefficient. PCK3145 was injected through intravenous route every other day for 28 days starting from day 1 when 50 to 60 mm$^3$ size subcutaneous tumors were apparent. Taxotere was injected by intra-peritoneal route at a sub-optimal concentration of 2 mg/kg on days 4 and 11 after subcutaneous tumors were evident. The different groups used in this experiment are illustrated in table 10 below. Each group contained 11 mice.

TABLE 10

| Treatment groups | Test and control articles | Dose level (µg/kg) | No. of animals | No of tumors |
| --- | --- | --- | --- | --- |
| 1. Negative control | PBS | 0 | 11 | 11 |
| 2. Positive control | Taxotere | 2000 | 11 | 11 |
| 3. | PCK3145 | 100 | 11 | 11 |
| 4. | PCK3145 + taxotere | 100 + 2000 | 11 | 11 |

Results of this experiment (FIG. 31) demonstrate a significant tumor growth retardation following combination treatment of PCK3145 and taxotere. This effect is statistically significant at days 19 and 22 post-tumor cell inoculation when compared by Student's t-test (p=0.02 at day 19 and p=0.047 at day 22), (p-values are measured by unpaired Student's t-test at p<0.05 as a cut-off limit) and was markedly better than taxotere administered alone at the same dose of 2 mg/kg (suboptimal dose).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A polypeptide comprising at least two repetitions of the amino acid sequence consisting of SEQ ID NO: 5, wherein the polypeptide inhibits the growth of prostatic adenocarcinoma.

2. A pharmaceutical composition comprising:
   a) the polypeptide of claim 1; and
   b) a pharmaceutically acceptable carrier.

3. The pharmaceutical composition of claim 2, further comprising an anticancer drug for the treatment of prostatic adenocarcinoma.

4. The pharmaceutical composition of claim 3, wherein said anticancer drug is selected from the group consisting of mitomycin, idarubicin, cisplatin, 5-fluoro-uracil, methotrexate, adriamycin, daunomycin, taxol, taxotere taxane, and mixtures thereof.

5. A method of treating a patient having prostatic adenocarcinoma, the method comprising administering the pharmaceutical composition of claim 2.

6. A polypeptide of at least 15 and no more than 64 contiguous amino acids of SEQ ID NO: 1, wherein the polypeptide inhibits the growth of prostatic adenocarcinoma, wherein the polypeptide comprises SEQ ID NO: 5.

7. A pharmaceutical composition comprising:
   a) the polypeptide of claim 6; and
   b) a pharmaceutically acceptable carrier.

8. The pharmaceutical composition of claim 7, further comprising an anticancer drug for the treatment of prostatic adenocarcinoma.

9. The pharmaceutical, composition of claim 8, wherein said anticancer drug is selected from the group consisting of mitomycin, idarubicin, cisplatin, 5-fluoro-uracil, methotrexate, adriamycin, daunomycin, taxol, taxotere, taxane, and mixtures thereof.

10. A method of treating a patient having prostatic adenocarcinoma, the method comprising administering the pharmaceutical composition of claim 7.

11. A polypeptide consisting of the amino acid sequence defined in SEQ ID NO.:5.

12. A pharmaceutical composition comprising:
    a) the polypeptide of claim 11; and
    b) a pharmaceutically acceptable carrier.

13. The pharmaceutical composition of claim 12, further comprising an anticancer drug for the treatment of prostatic adenocarcinoma.

14. The pharmaceutical composition of claim 13, wherein said anticancer drug is selected from the group consisting of mitomycin, idarubicin, cisplatin, 5-fluoro-uracil, methotrexate, adriamycin, daunomycin, taxol, taxotere, taxane, and mixtures thereof.

15. A method of treating a patient having prostatic adenocarcinoma, the method comprising administering the pharmaceutical composition of claim 12.

16. A polypeptide as defined in any one of SEQ ID NO.:10, SEQ ID NO.:11, SEQ ID NO.:12, SEQ ID NO.:13, SEQ ID NO.:14, SEQ ID NO.:15, SEQ ID NO.:16, SEQ ID NO.:17, SEQ ID NO.:18, SEQ ID NO.:19, SEQ ID NO.:20, SEQ ID NO.:21, SEQ ID NO.:22, SEQ ID NO.:23, SEQ ID NO.:24, SEQ ID NO.:25, SEQ ID NO.:26, SEQ ID NO.:27, SEQ ID NO.:28, SEQ ID NO.:29, SEQ ID NO.:30, SEQ ID NO.:31, SEQ ID NO.:32, SEQ ID NO.:33, SEQ ID NO.:34, SEQ ID NO.:35, SEQ ID NO.:36, SEQ ID NO.:37, SEQ ID NO.:38, SEQ ID NO.:39, SEQ ID NO.:40, SEQ ID NO.:41, SEQ ID NO.:42, SEQ ID NO.:43, SEQ ID NO.:44, SEQ ID NO.:45, SEQ ID NO.:46, SEQ ID NO.:47, SEQ ID NO.:48, SEQ ID NO.:49, SEQ ID NO.:50, SEQ ID NO.:51, SEQ ID NO.:52, SEQ ID NO.:53, SEQ ID NO.:54, SEQ ID NO.:55, SEQ ID NO.:56, SEQ ID NO.:57, SEQ ID NO.:58, SEQ ID NO.:59, SEQ ID NO.:60, SEQ ID NO.:61, SEQ ID NO.:62, SEQ ID NO.:63, SEQ ID NO.:64, SEQ ID NO.:65, SEQ ID NO.:66, SEQ ID NO.:67, SEQ ID NO.:68, SEQ ID NO.:69, SEQ ID NO.:70, SEQ ID NO.:71, SEQ ID NO.:72, SEQ ID NO.:73, SEQ ID NO.:74, SEQ ID NO.:75, SEQ ID NO.:76, SEQ ID NO.:77, SEQ ID NO.:78, SEQ ID NO.:79, SEQ ID NO.:80, SEQ ID NO.:81, SEQ ID NO.:82, SEQ ID NO.:83, SEQ ID NO.:84, SEQ ID NO.:85, SEQ ID NO.:86, SEQ ID NO.:87, SEQ ID NO.:88, SEQ ID NO.: 90, SEQ ID NO.: 91 and SEQ ID NO.: 92.

17. A pharmaceutical composition comprising:
a) the polypeptide of claim 16; and
b) a pharmaceutically acceptable carrier.

18. The pharmaceutical composition of claim 17, further comprising an anticancer drug for the treatment of prostatic adenocarcinoma.

19. The pharmaceutical composition of claim 18, wherein said anticancer drug is selected from the group consisting of mitomycin, idarubicin, cisplatin, 5-fluoro-uracil, methotrexate, adriamycin, daunomycin, taxol, taxotere taxane, and mixtures thereof.

20. A method of treating a patient having prostatic adenocarcinoma, the method comprising administering the pharmaceutical composition of claim 17.

21. A polypeptide which inhibits the growth of prostatic adenocarcinoma, said polypeptide having at least 50% of its amino acid sequence identical to the amino acid sequence consisting of SEQ ID NO: 5.

22. A pharmaceutical composition comprising:
a) the polypeptide of claim 21; and
b) a pharmaceutically acceptable carrier.

23. The pharmaceutical composition of claim 22, further comprising an anticancer drug for the treatment of prostatic adenocarcinoma.

24. The pharmaceutical composition of claim 23, wherein said anticancer drug is selected from the group consisting of mitomycin, idarubicin cisplatin, 5-fluoro-uracil, methotrexate, adriamycin, daunomycin, taxol, taxotere taxane, and mixtures thereof.

25. A method of treating a patient having prostatic adenocarcinoma, the method comprising administering the pharmaceutical composition of claim 22.

26. A polypeptide which inhibits the growth of prostatic adenocarcinoma, said polypeptide having at least 70% of its amino acid sequence identical to the amino acid sequence consisting of SEQ ID NO: 5.

27. A pharmaceutical composition comprising:
a) the polypeptide of claim 26; and
b) a pharmaceutically acceptable carrier.

28. The pharmaceutical composition of claim 27, further comprising an anticancer drug for the treatment of prostatic adenocarcinoma.

29. The pharmaceutical composition of claim 28, wherein said anticancer drug is selected from the group consisting of mitomycin, idarubicin, cisplatin, 5-fluoro-uracil, methotrexate, adriamycin, daunomycin, taxol, taxotere, taxane, and mixtures thereof.

30. A method of treating a patient having prostatic adenocarcinoma, the method comprising administering the pharmaceutical composition of claim 27.

31. A polypeptide which inhibits the growth of prostatic adenocarcinoma, said polypeptide having at least 90% of its amino acid sequence identical to the amino acid sequence consisting of SEQ ID NO: 5.

32. A pharmaceutical composition comprising:
a) the polypeptide of claim 31; and
b) a pharmaceutically acceptable carrier.

33. The pharmaceutical composition of claim 32, further comprising an anticancer drug for the treatment of prostatic adenocarcinoma.

34. The pharmaceutical composition of claim 33, wherein said anticancer drug is selected from the group consisting of mitomycin, idarubicin, cisplatin, 5-fluoro-uracil, methotrexate, adriamycin, daunomycin, taxol, taxotere, taxane, and mixtures thereof.

35. A method of treating a patient having prostatic adenocarcinoma, the method comprising administering the pharmaceutical composition of claim 32.

* * * * *

SEQUENCE LISTING

<160> NUMBER OF SEQ ID NOS: 92

<210> SEQ ID NO 1
<211> LENGTH: 94
<212> TYPE: PRT
<213> ORGANISM: Homo sapiens
<300> PUBLICATION INFORMATION:
<301> AUTHORS: Ulvsback, M., Lindstrom, C., Weiber, H., Abrahamson, P.A.,
      Lilja, H., and Lundwall, A"
<302> TITLE: Molecular cloning of a small prostate protein, known as
      beta-microsemenoprotein, PSP94 or beta-inhibin, and demonstration
      of transcripts in non-genital tissues.
<303> JOURNAL: Biochem. Biophys. Res Commun.
<304> VOLUME: 164
<305> ISSUE: 3
<306> PAGES: 1310-1315
<307> DATE: 1989
<308> DATABASE ACCESSION NUMBER: GI 131436
<309> DATABASE ENTRY DATE: 1988-08-01

```
<400> SEQUENCE: 1

Ser Cys Tyr Phe Ile Pro Asn Glu Gly Val Pro Gly Asp Ser Thr Arg
1               5                   10                  15

Lys Cys Met Asp Leu Lys Gly Asn Lys His Pro Ile Asn Ser Glu Trp
            20                  25                  30

Gln Thr Asp Asn Cys Glu Thr Cys Tyr Glu Thr Glu Ile Ser
        35                  40                  45

Cys Cys Thr Leu Val Ser Thr Pro Val Gly Tyr Asp Lys Asp Asn Cys
    50                  55                  60

Gln Arg Ile Phe Lys Lys Glu Asp Cys Lys Tyr Ile Val Val Glu Lys
65                  70                  75                  80

Lys Asp Pro Lys Lys Thr Cys Ser Val Ser Glu Trp Ile Ile
                85                  90

<210> SEQ ID NO 2
<211> LENGTH: 102
<212> TYPE: PRT
<213> ORGANISM: Artificial Sequence
<220> FEATURE:
<223> OTHER INFORMATION: recombinant human PSP94 (rHuPSP94) produced
      from yeast

<400> SEQUENCE: 2

Glu Ala Glu Ala Tyr Val Glu Phe Ser Cys Tyr Phe Ile Pro Asn Glu
1               5                   10                  15

Gly Val Pro Gly Asp Ser Thr Arg Lys Cys Met Asp Leu Lys Gly Asn
            20                  25                  30

Lys His Pro Ile Asn Ser Glu Trp Gln Thr Asp Asn Cys Glu Thr Cys
        35                  40                  45

Thr Cys Tyr Glu Thr Glu Ile Ser Cys Cys Thr Leu Val Ser Thr Pro
    50                  55                  60

Val Gly Tyr Asp Lys Asp Asn Cys Gln Arg Ile Phe Lys Lys Glu Asp
65                  70                  75                  80

Cys Lys Tyr Ile Val Val Glu Lys Lys Asp Pro Lys Lys Thr Cys Ser
                85                  90                  95

Val Ser Glu Trp Ile Ile
            100

<210> SEQ ID NO 3
<211> LENGTH: 10
<212> TYPE: PRT
<213> ORGANISM: Artificial Sequence
<220> FEATURE:
<223> OTHER INFORMATION: decapeptide

<400> SEQUENCE: 3

Tyr Thr Cys Ser Val Ser Glu Pro Gly Ile
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Polypeptide 7-21

<400> SEQUENCE: 4

Asn Glu Gly Val Pro Gly Asp Ser Thr Arg Lys Cys Met Asp Leu
1               5                   10                  15
```

```
<210> SEQ ID NO 5
<211> LENGTH: 15
<212> TYPE: PRT
<213> ORGANISM: Artificial Sequence
<220> FEATURE:
<223> OTHER INFORMATION: PCK3145 (polypeptide 31-45)

<400> SEQUENCE: 5

Glu Trp Gln Thr Asp Asn Cys Glu Thr Cys Thr Cys Tyr Glu Thr
1               5                   10                  15

<210> SEQ ID NO 6
<211> LENGTH: 19
<212> TYPE: PRT
<213> ORGANISM: Artificial Sequence
<220> FEATURE:
<223> OTHER INFORMATION: Polypeptide 76-94

<400> SEQUENCE: 6

Ile Val Val Glu Lys Lys Asp Pro Lys Lys Thr Cys Ser Val Ser Glu
1               5                   10                  15

Trp Ile Ile

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide used in the amplification and
      cloning of rHPSP94

<400> SEQUENCE: 7
gggaagaatt ctcatgctat ttcata                                          26

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide used in the amplification and
      cloning of rHPSP94

<400> SEQUENCE: 8
tggatatctg cagaattcgg c                                               21

<210> SEQ ID NO 9
<211> LENGTH: 285
<212> TYPE: DNA
<213> ORGANISM: Homo sapiens
<300> PUBLICATION INFORMATION:
<301> AUTHORS: Green, C.B., Liu, W.Y. and Kwok, S.C.
<302> TITLE: Cloning and nucleotide sequence analysis of the human beta-
      microseminoprotein gene.
<303> JOURNAL: Biochem. Biophys. Res. Commun.
<304> VOLUME: 167
<305> ISSUE: 3
<306> PAGES: 1184-1190
<307> DATE: 1990
<308> DATABASE ACCESSION NUMBER: GI 514370
<309> DATABASE ENTRY DATE: 1995-01-07

<400> SEQUENCE: 9
tcatgctatt tcatacctaa tgagggagtt ccaggagatt caaccaggaa atgcatggat     60
ctcaaaggaa acaaacaccc aataaactcg gagtggcaga ctgacaactg tgagacatgc    120
acttgctacg aaacagaaat tcatgttgc acccttgttt ctacacctgt ggttatgac     180 aaagacaact gccaaagaat cttcaagaag gaggactgca agtatatcgt ggtggagaag    240
```

-continued aaggacccaa aaaagacctg ttctgtcagt gaatggataa tctaa               285

<210> SEQ ID NO 10
<211> LENGTH: 16
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 10

Glu Trp Gln Thr Asp Asn Cys Glu Thr Cys Thr Cys Tyr Glu Thr Glu
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 11

Glu Trp Gln Thr Asp Asn Cys Glu Thr Cys Thr Cys Tyr Glu Thr Glu
1               5                   10                  15

Ile

<210> SEQ ID NO 12
<211> LENGTH: 18
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 12

Glu Trp Gln Thr Asp Asn Cys Glu Thr Cys Thr Cys Tyr Glu Thr Glu
1               5                   10                  15

Ile Ser

<210> SEQ ID NO 13
<211> LENGTH: 19
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 13

Glu Trp Gln Thr Asp Asn Cys Glu Thr Cys Thr Cys Tyr Glu Thr Glu
1               5                   10                  15

Ile Ser Cys

<210> SEQ ID NO 14
<211> LENGTH: 20
<212> TYPE: PRT
<213> ORGANISM: Artificial Sequence
<220> FEATURE:
<223> OTHER INFORMATION: Polypeptide derived from rHuPSP94 sequence
      polypeptide analog)

<400> SEQUENCE: 14

Glu Trp Gln Thr Asp Asn Cys Glu Thr Cys Thr Cys Tyr Glu Thr Glu
1               5                   10                  15

Ile Ser Cys Cys
          20

<210> SEQ ID NO 15
<211> LENGTH: 21
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 15

Glu Trp Gln Thr Asp Asn Cys Glu Thr Cys Thr Cys Tyr Glu Thr Glu
1               5                   10                  15

Ile Ser Cys Cys Thr
          20

<210> SEQ ID NO 16
<211> LENGTH: 22
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 16

Glu Trp Gln Thr Asp Asn Cys Glu Thr Cys Thr Cys Tyr Glu Thr Glu
1               5                   10                  15

Ile Ser Cys Cys Thr Leu
          20

<210> SEQ ID NO 17
<211> LENGTH: 23
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 17

Glu Trp Gln Thr Asp Asn Cys Glu Thr Cys Thr Cys Tyr Glu Thr Glu
1               5                   10                  15

Ile Ser Cys Cys Thr Leu Val
          20

<210> SEQ ID NO 18
<211> LENGTH: 24
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 18

Glu Trp Gln Thr Asp Asn Cys Glu Thr Cys Thr Cys Tyr Glu Thr Glu
1               5                   10                  15

Ile Ser Cys Cys Thr Leu Val Ser
          20

<210> SEQ ID NO 19
<211> LENGTH: 25
<212> TYPE: PRT
<213> ORGANISM: Artificial Sequence
<220> FEATURE:
<223> OTHER INFORMATION: Polypeptide derived from rHuPSP94 sequence
      (polypeptide analog)

-continued

<400> SEQUENCE: 19

Glu Trp Gln Thr Asp Asn Cys Glu Thr Cys Thr Cys Tyr Glu Thr Glu
1               5                   10                  15

Ile Ser Cys Cys Thr Leu Val Ser Thr
            20                  25

<210> SEQ ID NO 20
<211> LENGTH: 26
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 20

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro
            20                  25

<210> SEQ ID NO 21
<211> LENGTH: 27
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 21

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val
            20                  25

<210> SEQ ID NO 22
<211> LENGTH: 28
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 22

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly
            20                  25

<210> SEQ ID NO 23
<211> LENGTH: 29
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 23

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr
            20                  25

<210> SEQ ID NO 24

```
<211> LENGTH: 30
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 24

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 25

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 26

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

<210> SEQ ID NO 27
<211> LENGTH: 33
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 27

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn

<210> SEQ ID NO 28
<211> LENGTH: 34
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 28
```

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys
```

<210> SEQ ID NO 29
<211> LENGTH: 35
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 29

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln
        35
```

<210> SEQ ID NO 30
<211> LENGTH: 36
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 30

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg
        35
```

<210> SEQ ID NO 31
<211> LENGTH: 37
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 31

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile
        35
```

<210> SEQ ID NO 32
<211> LENGTH: 38
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 32

-continued

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe
            35
```

<210> SEQ ID NO 33
<211> LENGTH: 39
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 33

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys
            35
```

<210> SEQ ID NO 34
<211> LENGTH: 40
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 34

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys
            35                  40
```

<210> SEQ ID NO 35
<211> LENGTH: 41
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 35

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu
            35                  40
```

<210> SEQ ID NO 36
<211> LENGTH: 42
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 36

```
Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp
        35                  40

<210> SEQ ID NO 37
<211> LENGTH: 43
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 37

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys
        35                  40

<210> SEQ ID NO 38
<211> LENGTH: 44
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 38

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys
        35                  40

<210> SEQ ID NO 39
<211> LENGTH: 45
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 39

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr
        35                  40                  45

<210> SEQ ID NO 40
<211> LENGTH: 46
<212> TYPE: PRT
<213> ORGANISM: Artificial Sequence
<220> FEATURE:
<223> OTHER INFORMATION: Polypeptide derived from rHuPSP94 sequence
      (polypeptide analog)
```

-continued

```
<400> SEQUENCE: 40

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile
        35                  40                  45

<210> SEQ ID NO 41
<211> LENGTH: 47
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 41

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val
        35                  40                  45

<210> SEQ ID NO 42
<211> LENGTH: 48
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 42

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

<210> SEQ ID NO 43
<211> LENGTH: 49
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 43

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
         35                  40                  45
    Glu

<210> SEQ ID NO 44
<211> LENGTH: 50
<212> TYPE: PRT
<213> ORGANISM: Artificial Sequence
<220> FEATURE:
<223> OTHER INFORMATION: Polypeptide derived from rHuPSP94 sequence
```

-continued (polypeptide analog)

<400> SEQUENCE: 44

Glu Trp Gln Thr Asp Asn Cys Glu Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys
    50

<210> SEQ ID NO 45
<211> LENGTH: 51
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 45

Glu Trp Gln Thr Asp Asn Cys Glu Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys
    50

<210> SEQ ID NO 46
<211> LENGTH: 52
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 46

Glu Trp Gln Thr Asp Asn Cys Glu Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp
    50

<210> SEQ ID NO 47
<211> LENGTH: 53
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 47

Glu Trp Gln Thr Asp Asn Cys Glu Thr Cys Tyr Glu Thr Glu
1               5                   10                  15

Ile Ser Cys Cys Thr Leu Val Ser Thr Pro Val Gly Tyr Asp Lys Asp
            20                  25                  30

-continued

Asn Cys Gln Arg Ile Phe Lys Lys Glu Asp Cys Lys Tyr Ile Val Val
          35                  40                  45

Glu Lys Lys Asp Pro
    50

<210> SEQ ID NO 48
<211> LENGTH: 54
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 48

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
          35                  40                  45

Glu Lys Lys Asp Pro Lys
    50

<210> SEQ ID NO 49
<211> LENGTH: 55
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 49

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
          35                  40                  45

Glu Lys Lys Asp Pro Lys Lys
    50                  55

<210> SEQ ID NO 50
<211> LENGTH: 56
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 50

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
          35                  40                  45

Glu Lys Lys Asp Pro Lys Lys Thr
    50                  55

<210> SEQ ID NO 51
<211> LENGTH: 57
<212> TYPE: PRT

<213> ORGANISM: Artificial Sequence
<220> FEATURE:
<223> OTHER INFORMATION: Polypeptide derived from rHuPSP94 sequence
      (polypeptide analog)

<400> SEQUENCE: 51

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys
    50                  55

<210> SEQ ID NO 52
<211> LENGTH: 58
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 52

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser
    50                  55

<210> SEQ ID NO 53
<211> LENGTH: 59
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 53

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val
    50                  55

<210> SEQ ID NO 54
<211> LENGTH: 60
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 54

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val Ser
    50                  55                  60

<210> SEQ ID NO 55
<211> LENGTH: 61
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 55

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val Ser Glu
    50                  55                  60

<210> SEQ ID NO 56
<211> LENGTH: 62
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 56

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val Ser Glu Trp
    50                  55                  60

<210> SEQ ID NO 57
<211> LENGTH: 63
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 57

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val Ser Glu Trp Ile
    50                  55                  60

<210> SEQ ID NO 58
<211> LENGTH: 64
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 58

Glu Trp Gln Thr Asp Asn Cys Glu Thr Cys Thr Cys Tyr Glu Thr Glu
1               5                   10                  15

Ile Ser Cys Cys Thr Leu Val Ser Thr Pro Val Gly Tyr Asp Lys Asp
            20                  25                  30

Asn Cys Gln Arg Ile Phe Lys Lys Glu Asp Cys Lys Tyr Ile Val Val
        35                  40                  45

Glu Lys Lys Asp Pro Lys Lys Thr Cys Ser Val Ser Glu Trp Ile Ile
    50                  55                  60

<210> SEQ ID NO 59
<211> LENGTH: 16
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 59

Ser Glu Trp Gln Thr Asp Asn Cys Glu Thr Cys Thr Cys Tyr Glu Thr
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 60

Asn Ser Glu Trp Gln Thr Asp Asn Cys Glu Thr Cys Thr Cys Tyr Glu
1               5                   10                  15

Thr

<210> SEQ ID NO 61
<211> LENGTH: 18
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 61

Ile Asn Ser Glu Trp Gln Thr Asp Asn Cys Glu Thr Cys Thr Cys Tyr
1               5                   10                  15

Glu Thr

<210> SEQ ID NO 62
<211> LENGTH: 19
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 62

```
Pro Ile Asn Ser Glu Trp Gln Thr Asp Asn Cys Glu Thr Cys Thr Cys
1               5                   10                  15

Tyr Glu Thr
```

<210> SEQ ID NO 63
<211> LENGTH: 20
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 63

```
His Pro Ile Asn Ser Glu Trp Gln Thr Asp Asn Cys Glu Thr Cys Thr
1               5                   10                  15

Cys Tyr Glu Thr
                20
```

<210> SEQ ID NO 64
<211> LENGTH: 21
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 64

```
Lys His Pro Ile Asn Ser Glu Trp Gln Thr Asp Asn Cys Glu Thr Cys
1               5                   10                  15

Thr Cys Tyr Glu Thr
                20
```

<210> SEQ ID NO 65
<211> LENGTH: 22
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 65

```
Asn Lys His Pro Ile Asn Ser Glu Trp Gln Thr Asp Asn Cys Glu Thr
1               5                   10                  15

Cys Thr Cys Tyr Glu Thr
                20
```

<210> SEQ ID NO 66
<211> LENGTH: 23
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 66

```
Gly Asn Lys His Pro Ile Asn Ser Glu Trp Gln Thr Asp Asn Cys Glu
1               5                   10                  15

Thr Cys Thr Cys Tyr Glu Thr
                20
```

<210> SEQ ID NO 67
<211> LENGTH: 24
<212> TYPE: PRT
<213> ORGANISM: Artificial Sequence
<220> FEATURE:

```
<223> OTHER INFORMATION: Polypeptide derived from rHuPSP94 sequence
      (polypeptide analog)

<400> SEQUENCE: 67

Lys Gly Asn Lys His Pro Ile Asn Ser Glu Trp Gln Thr Asp Asn Cys
1               5                   10                  15

Glu Thr Cys Thr Cys Tyr Glu Thr
            20

<210> SEQ ID NO 68
<211> LENGTH: 25
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 68

Leu Lys Gly Asn Lys His Pro Ile Asn Ser Glu Trp Gln Thr Asp Asn
1               5                   10                  15

Cys Glu Thr Cys Thr Cys Tyr Glu Thr
            20                  25

<210> SEQ ID NO 69
<211> LENGTH: 26
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 69

Asp Leu Lys Gly Asn Lys His Pro Ile Asn Ser Glu Trp Gln Thr Asp
1               5                   10                  15

Asn Cys Glu Thr Cys Thr Cys Tyr Glu Thr
            20                  25

<210> SEQ ID NO 70
<211> LENGTH: 27
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 70

Met Asp Leu Lys Gly Asn Lys His Pro Ile Asn Ser Glu Trp Gln Thr
1               5                   10                  15

Asp Asn Cys Glu Thr Cys Thr Cys Tyr Glu Thr
            20                  25

<210> SEQ ID NO 71
<211> LENGTH: 28
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 71

Cys Met Asp Leu Lys Gly Asn Lys His Pro Ile Asn Ser Glu Trp Gln
1               5                   10                  15

Thr Asp Asn Cys Glu Thr Cys Thr Cys Tyr Glu Thr
            20                  25
```

<210> SEQ ID NO 72
<211> LENGTH: 29
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 72

Lys Cys Met Asp Leu Lys Gly Asn Lys His Pro Ile Asn Ser Glu Trp
1               5                   10                  15

Gln Thr Asp Asn Cys Glu Thr Cys Thr Cys Tyr Glu Thr
            20                  25

<210> SEQ ID NO 73
<211> LENGTH: 30
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 73

Arg Lys Cys Met Asp Leu Lys Gly Asn Lys His Pro Ile Asn Ser Glu
1               5                   10                  15

Trp Gln Thr Asp Asn Cys Glu Thr Cys Thr Cys Tyr Glu Thr
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 74

Thr Arg Lys Cys Met Asp Leu Lys Gly Asn Lys His Pro Ile Asn Ser
1               5                   10                  15

Glu Trp Gln Thr Asp Asn Cys Glu Thr Cys Thr Cys Tyr Glu Thr
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 75

Ser Thr Arg Lys Cys Met Asp Leu Lys Gly Asn Lys His Pro Ile Asn
1               5                   10                  15

Ser Glu Trp Gln Thr Asp Asn Cys Glu Thr Cys Thr Cys Tyr Glu Thr
            20                  25                  30

<210> SEQ ID NO 76
<211> LENGTH: 33
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 76

```
Asp Ser Thr Arg Lys Cys Met Asp Leu Lys Gly Asn Lys His Pro Ile
1               5                   10                  15

Asn Ser Glu Trp Gln Thr Asp Asn Cys Glu Thr Cys Tyr Glu
            20                  25                  30

Thr

<210> SEQ ID NO 77
<211> LENGTH: 34
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 77

Gly Asp Ser Thr Arg Lys Cys Met Asp Leu Lys Gly Asn Lys His Pro
1               5                   10                  15

Ile Asn Ser Glu Trp Gln Thr Asp Asn Cys Glu Thr Cys Tyr
            20                  25                  30

Glu Thr

<210> SEQ ID NO 78
<211> LENGTH: 35
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 78

Pro Gly Asp Ser Thr Arg Lys Cys Met Asp Leu Lys Gly Asn Lys His
1               5                   10                  15

Pro Ile Asn Ser Glu Trp Gln Thr Asp Asn Cys Glu Thr Cys Thr Cys
            20                  25                  30

Tyr Glu Thr
        35

<210> SEQ ID NO 79
<211> LENGTH: 36
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 79

Val Pro Gly Asp Ser Thr Arg Lys Cys Met Asp Leu Lys Gly Asn Lys
1               5                   10                  15

His Pro Ile Asn Ser Glu Trp Gln Thr Asp Asn Cys Glu Thr Cys Thr
            20                  25                  30

Cys Tyr Glu Thr
        35

<210> SEQ ID NO 80
<211> LENGTH: 37
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 80

Gly Val Pro Gly Asp Ser Thr Arg Lys Cys Met Asp Leu Lys Gly Asn
```

```
                1               5                  10                 15
Lys His Pro Ile Asn Ser Glu Trp Gln Thr Asp Asn Cys Glu Thr Cys
                20                 25                 30

Thr Cys Tyr Glu Thr
        35

<210> SEQ ID NO 81
<211> LENGTH: 38
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 81

Glu Gly Val Pro Gly Asp Ser Thr Arg Lys Cys Met Asp Leu Lys Gly
1               5                   10                  15

Asn Lys His Pro Ile Asn Ser Glu Trp Gln Thr Asp Asn Cys Glu Thr
                20                  25                  30

Cys Thr Cys Tyr Glu Thr
        35

<210> SEQ ID NO 82
<211> LENGTH: 39
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 82

Asn Glu Gly Val Pro Gly Asp Ser Thr Arg Lys Cys Met Asp Leu Lys
1               5                   10                  15

Gly Asn Lys His Pro Ile Asn Ser Glu Trp Gln Thr Asp Asn Cys Glu
                20                  25                  30

Thr Cys Thr Cys Tyr Glu Thr
        35

<210> SEQ ID NO 83
<211> LENGTH: 40
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 83

Pro Asn Glu Gly Val Pro Gly Asp Ser Thr Arg Lys Cys Met Asp Leu
1               5                   10                  15

Lys Gly Asn Lys His Pro Ile Asn Ser Glu Trp Gln Thr Asp Asn Cys
                20                  25                  30

Glu Thr Cys Thr Cys Tyr Glu Thr
        35                  40

<210> SEQ ID NO 84
<211> LENGTH: 41
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 84
```

Ile Pro Asn Glu Gly Val Pro Gly Asp Ser Thr Arg Lys Cys Met Asp
1               5                   10                  15

Leu Lys Gly Asn Lys His Pro Ile Asn Ser Glu Trp Gln Thr Asp Asn
            20                  25                  30

Cys Glu Thr Cys Thr Cys Tyr Glu Thr
            35                  40

<210> SEQ ID NO 85
<211> LENGTH: 42
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 85

Phe Ile Pro Asn Glu Gly Val Pro Gly Asp Ser Thr Arg Lys Cys Met
1               5                   10                  15

Asp Leu Lys Gly Asn Lys His Pro Ile Asn Ser Glu Trp Gln Thr Asp
            20                  25                  30

Asn Cys Glu Thr Cys Thr Cys Tyr Glu Thr
            35                  40

<210> SEQ ID NO 86
<211> LENGTH: 43
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 86

Tyr Phe Ile Pro Asn Glu Gly Val Pro Gly Asp Ser Thr Arg Lys Cys
1               5                   10                  15

Met Asp Leu Lys Gly Asn Lys His Pro Ile Asn Ser Glu Trp Gln Thr
            20                  25                  30

Asp Asn Cys Glu Thr Cys Thr Cys Tyr Glu Thr
            35                  40

<210> SEQ ID NO 87
<211> LENGTH: 44
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 87

Cys Tyr Phe Ile Pro Asn Glu Gly Val Pro Gly Asp Ser Thr Arg Lys
1               5                   10                  15

Cys Met Asp Leu Lys Gly Asn Lys His Pro Ile Asn Ser Glu Trp Gln
            20                  25                  30

Thr Asp Asn Cys Glu Thr Cys Thr Cys Tyr Glu Thr
            35                  40

<210> SEQ ID NO 88
<211> LENGTH: 45
<212> TYPE: PRT
<213> ORGANISM: Artificial Sequence
<220> FEATURE:
<223> OTHER INFORMATION: Polypeptide derived from rHuPSP94 sequence
      (polypeptide analog)

<400> SEQUENCE: 88

```
Ser Cys Tyr Phe Ile Pro Asn Glu Gly Val Pro Gly Asp Ser Thr Arg
1               5                   10                  15

Lys Cys Met Asp Leu Lys Gly Asn Lys His Pro Ile Asn Ser Glu Trp
                20                  25                  30

Gln Thr Asp Asn Cys Glu Thr Cys Thr Cys Tyr Glu Thr
                35                  40                  45
```

<210> SEQ ID NO 89
<211> LENGTH: 15
<212> TYPE: PRT
<213> ORGANISM: Artificial Sequence
<220> FEATURE:
<223> OTHER INFORMATION: Polypeptide derived from PCK3145 sequence
      (polypeptide analog)
<221> NAME/KEY: MISC_FEATURE
<222> LOCATION: (1)..(1)
<223> OTHER INFORMATION: Xaa may be glutamic acid, asparagine or
      aspartic acid.
<221> NAME/KEY: MISC_FEATURE
<222> LOCATION: (4)..(4)
<223> OTHER INFORMATION: Xaa may be threonine or serine.
<221> NAME/KEY: MISC_FEATURE
<222> LOCATION: (6)..(6)
<223> OTHER INFORMATION: Xaa may be glutamic acid, asparagine, or
      aspartic acid.
<221> NAME/KEY: MISC_FEATURE
<222> LOCATION: (8)..(8)
<223> OTHER INFORMATION: Xaa may be glutamic acid, asparagine, or
      aspartic acid.
<221> NAME/KEY: MISC_FEATURE
<222> LOCATION: (9)..(9)
<223> OTHER INFORMATION: Xaa may be threonine or serine.
<221> NAME/KEY: MISC_FEATURE
<222> LOCATION: (11)..(11)
<223> OTHER INFORMATION: Xaa may be threonine or serine.
<221> NAME/KEY: MISC_FEATURE
<222> LOCATION: (13)..(13)
<223> OTHER INFORMATION: Xaa may be tyrosine or phenylalanine.
<221> NAME/KEY: MISC_FEATURE
<222> LOCATION: (14)..(14)
<223> OTHER INFORMATION: Xaa may be glutamic acid, asparagine, or
      aspartic acid.
<221> NAME/KEY: MISC_FEATURE
<222> LOCATION: (15)..(15)
<223> OTHER INFORMATION: Xaa may be threonine or serine.

<400> SEQUENCE: 89

```
Xaa Trp Gln Xaa Asp Xaa Cys Xaa Xaa Cys Xaa Cys Xaa Xaa Xaa
1               5                   10                  15
```

<210> SEQ ID NO 90
<211> LENGTH: 30
<212> TYPE: PRT
<213> ORGANISM: Artificial Sequence
<220> FEATURE:
<223> OTHER INFORMATION: Polypeptide derived from PCK3145 sequence
      (polypeptide analog)

<400> SEQUENCE: 90

```
Glu Trp Gln Thr Asp Asn Cys Glu Thr Cys Thr Cys Tyr Glu Thr Glu
1               5                   10                  15

Trp Gln Thr Asp Asn Cys Glu Thr Cys Thr Cys Tyr Glu Thr
                20                  25                  30
```

<210> SEQ ID NO 91
<211> LENGTH: 45
<212> TYPE: PRT
<213> ORGANISM: Artificial Sequence
<220> FEATURE:
<223> OTHER INFORMATION: Polypeptide derived from PCK3145 sequence -continued (polypeptide analog)

<400> SEQUENCE: 91

Glu Trp Gln Thr Asp Asn Cys Glu Thr Cys Thr Cys Tyr Glu Thr Glu
1               5                   10                  15

Trp Gln Thr Asp Asn Cys Glu Thr Cys Thr Cys Tyr Glu Thr Glu Trp
            20                  25                  30

Gln Thr Asp Asn Cys Glu Thr Cys Thr Cys Tyr Glu Thr
        35                  40                  45

<210> SEQ ID NO 92
<211> LENGTH: 60
<212> TYPE: PRT
<213> ORGANISM: Artificial Sequence
<220> FEATURE:
<223> OTHER INFORMATION: Polypeptide derived from PCK3145 sequence
      (polypeptide analog)

<400> SEQUENCE: 92

Glu Trp Gln Thr Asp Asn Cys Glu Thr Cys Thr Cys Tyr Glu Thr Glu
1               5                   10                  15

Trp Gln Thr Asp Asn Cys Glu Thr Cys Thr Cys Tyr Glu Thr Glu Trp
            20                  25                  30

Gln Thr Asp Asn Cys Glu Thr Cys Thr Cys Tyr Glu Thr Glu Trp Gln
        35                  40                  45

Thr Asp Asn Cys Glu Thr Cys Thr Cys Tyr Glu Thr
    50                  55                  60